(12) United States Patent
Rozenberg et al.

(10) Patent No.: US 10,561,527 B2
(45) Date of Patent: *Feb. 18, 2020

(54) METHODS AND DEVICES FOR NON-INVASIVE CEREBRAL AND SYSTEMIC COOLING ALTERNATING LIQUID MIST/GAS FOR INDUCTION AND GAS FOR MAINTENANCE

(71) Applicant: BrainCool AB, Lund (SE)

(72) Inventors: Allan Rozenberg, San Diego, CA (US); Denise Barbut, New York, NY (US); John K Hoffman, Poway, CA (US); Thomas H Shaffer, Chadds Ford, PA (US)

(73) Assignee: BrainCool AB, Lund (SE)

( * ) Notice: Subject to any disclaimer, the term of this patent is extended or adjusted under 35 U.S.C. 154(b) by 837 days.

This patent is subject to a terminal disclaimer.

(21) Appl. No.: 15/171,858

(22) Filed: Jun. 2, 2016

(65) Prior Publication Data

US 2017/0027745 A1 Feb. 2, 2017

Related U.S. Application Data

(63) Continuation of application No. 13/423,561, filed on Mar. 19, 2012, now Pat. No. 9,358,150, which is a
(Continued)

(51) Int. Cl.
*A61F 7/12* (2006.01)
*A61M 15/08* (2006.01)
(Continued)

(52) U.S. Cl.
CPC ............... *A61F 7/12* (2013.01); *A61F 7/123* (2013.01); *A61K 9/007* (2013.01); *A61K 31/02* (2013.01);
(Continued)

(58) Field of Classification Search
CPC ....... A61F 7/12; A61F 7/123; A61F 2007/126
See application file for complete search history.

(56) References Cited

U.S. PATENT DOCUMENTS

| 3,516,407 A | 6/1970 | Ruggero |
| 3,766,924 A | 10/1973 | Pidgeon |

(Continued)

FOREIGN PATENT DOCUMENTS

| DE | 19952440 | 5/2001 |
| EP | 0692273 A1 | 1/1996 |

(Continued)

OTHER PUBLICATIONS

Bluestone et al., "Intranasal Freezing for Severe Epistaxis," *International Surgery* Jan. 1970; 53(1):11-15.
(Continued)

*Primary Examiner* — Kaitlyn E Smith
(74) *Attorney, Agent, or Firm* — Capitol City TechLaw

(57) ABSTRACT

Devices for cerebral and systemic cooling via a patient's nasopharyngeal cavity are described. Cooling assemblies include at least one elongate tubular member having first and second lumens, a source of liquid coolant, a gas source communicating with the first lumen, and a switch for alternately connecting the liquid coolant source to the second lumen. The first lumen transports a compressed gas and the second lumen transports a volatile liquid. The pressurized fluid may be a perfluorocarbon. The perfluorocarbon may be perfluorohexane, perfluoropentane, or 2-methyl-perfluoropentane. The gas may be air, oxygen, or a combination.

8 Claims, 53 Drawing Sheets

Related U.S. Application Data continuation-in-part of application No. 13/315,141, filed on Dec. 8, 2011, now Pat. No. 8,313,520, which is a continuation of application No. 12/825,248, filed on Jun. 28, 2010, now Pat. No. 8,075,605, which is a continuation of application No. 11/881,105, filed on Jul. 24, 2007, now abandoned, which is a continuation of application No. 11/603,846, filed on Nov. 22, 2006, now Pat. No. 7,837,722, which is a continuation-in-part of application No. 11/432,285, filed on May 10, 2006, now Pat. No. 7,824,436.

(60) Provisional application No. 60/737,025, filed on Nov. 15, 2005, provisional application No. 60/717,590, filed on Sep. 16, 2005, provisional application No. 60/681,068, filed on May 13, 2005.

(51) Int. Cl.

| | | |
|---|---|---|
| *A61M 25/00* | (2006.01) | |
| *A61K 31/02* | (2006.01) | |
| *A61M 16/04* | (2006.01) | |
| *A61K 9/00* | (2006.01) | |
| *A61K 47/06* | (2006.01) | |
| *A61M 25/10* | (2013.01) | |
| *A61M 31/00* | (2006.01) | |
| *A61F 7/00* | (2006.01) | |

(52) U.S. Cl.
CPC .......... *A61K 47/06* (2013.01); *A61M 15/08* (2013.01); *A61M 16/0409* (2014.02); *A61M 16/0486* (2014.02); *A61M 25/003* (2013.01); *A61M 25/007* (2013.01); *A61M 25/0032* (2013.01); *A61M 25/0068* (2013.01); *A61F 2007/0006* (2013.01); *A61F 2007/0065* (2013.01); *A61M 16/04* (2013.01); *A61M 25/1011* (2013.01); *A61M 31/00* (2013.01); *A61M 2025/0034* (2013.01); *A61M 2025/0036* (2013.01); *A61M 2025/0073* (2013.01)

(56) References Cited

U.S. PATENT DOCUMENTS

| | | | |
|---|---|---|---|
| 4,095,593 A | 6/1978 | Webbon | |
| 4,138,743 A | 2/1979 | Elkins | |
| 4,765,338 A | 8/1988 | Turner et al. | |
| 4,773,410 A * | 9/1988 | Blackmer | A61D 7/04 128/203.26 |
| 4,819,619 A | 4/1989 | Augustine et al. | |
| 4,821,715 A | 4/1989 | Downing | |
| 4,895,562 A | 1/1990 | Lopez | |
| 5,158,536 A * | 10/1992 | Sekins | A61M 16/0486 604/20 |
| D354,376 S | 1/1995 | Kun | |
| 5,540,225 A * | 7/1996 | Schutt | A61K 9/0026 128/207.15 |
| 5,568,884 A | 10/1996 | Bruna | |
| 5,624,392 A | 4/1997 | Saab | |
| 5,702,362 A | 12/1997 | Herold et al. | |
| 5,792,100 A | 8/1998 | Shantha | |
| 5,899,878 A | 5/1999 | Glassman | |
| 5,927,273 A | 7/1999 | Federowicz | |
| RE36,460 E | 12/1999 | Klatz | |
| 6,030,412 A | 2/2000 | Klatz | |
| 6,090,132 A | 7/2000 | Fox | |
| 6,142,147 A * | 11/2000 | Head | A61M 16/12 128/203.12 |
| 6,149,624 A | 11/2000 | McShane | |
| 6,156,057 A | 12/2000 | Fox | |
| 6,166,092 A | 12/2000 | Sekins | |
| 6,178,562 B1 | 1/2001 | Elkins | |
| 6,248,126 B1 | 6/2001 | Lesser et al. | |
| 6,303,156 B1 | 10/2001 | Ferrigno | |
| 6,352,550 B1 | 3/2002 | Gildersleeve | |
| 6,386,202 B1 | 5/2002 | Frazee | |
| 6,394,093 B1 * | 5/2002 | Lethi | A61M 16/0461 128/207.13 |
| 6,398,774 B1 | 6/2002 | Penner et al. | |
| 6,537,246 B1 | 3/2003 | Unger et al. | |
| 6,548,049 B1 | 4/2003 | Cutie et al. | |
| 6,647,930 B2 | 11/2003 | Nurmi | |
| 6,695,872 B2 | 2/2004 | Elkins | |
| 6,736,837 B2 | 4/2004 | Fox | |
| 6,730,115 B1 | 5/2004 | Heaton | |
| 6,749,597 B2 | 6/2004 | Frank | |
| 6,929,003 B2 | 8/2005 | Blacker | |
| 6,959,708 B1 | 11/2005 | Rasor et al. | |
| 6,983,749 B2 | 1/2006 | Kumar | |
| 7,077,825 B1 | 7/2006 | Stull | |
| 7,189,253 B2 | 3/2007 | Lunderqvist et al. | |
| 7,201,163 B2 * | 4/2007 | Jiang | A61M 16/1075 128/200.14 |
| 7,824,436 B2 | 11/2010 | Barbut | |
| 8,100,123 B2 * | 1/2012 | Belson | A61F 7/0085 128/204.15 |
| 8,157,767 B2 * | 4/2012 | Rozenberg | A61M 16/0486 604/98.01 |
| 8,281,786 B2 * | 10/2012 | Belson | A61F 7/0085 128/204.15 |
| 8,308,787 B2 | 11/2012 | Kreck | |
| 8,402,968 B2 * | 3/2013 | Belson | A61F 7/0085 128/204.15 |
| 8,512,280 B2 * | 8/2013 | Rozenberg | A61M 16/0486 604/94.01 |
| 9,004,066 B2 * | 4/2015 | Belson | A61F 7/0085 128/204.15 |
| 9,265,922 B2 * | 2/2016 | Barbut | A61M 31/00 |
| 9,757,272 B2 * | 9/2017 | Belson | A61F 7/0085 |
| 9,775,741 B2 * | 10/2017 | Barbut | A61F 7/12 |
| 10,076,441 B2 * | 9/2018 | Rozenberg | A61M 16/0486 |
| 2001/0008652 A1 | 7/2001 | Hamada et al. | |
| 2001/0016764 A1 | 8/2001 | Dobak | |
| 2002/0023640 A1 | 2/2002 | Nightengale | |
| 2002/0040924 A1 | 4/2002 | Fox | |
| 2002/0055746 A1 | 5/2002 | Burke et al. | |
| 2002/0077593 A1 * | 6/2002 | Perkins | A61M 1/0058 604/96.01 |
| 2002/0091426 A1 | 7/2002 | Fox | |
| 2002/0138121 A1 | 9/2002 | Fox | |
| 2002/0161349 A1 | 10/2002 | Allers | |
| 2003/0131844 A1 * | 7/2003 | Kumar | A61K 33/00 128/200.24 |
| 2003/0136402 A1 | 7/2003 | Jiang et al. | |
| 2003/0149613 A1 | 8/2003 | Johnson | |
| 2003/0181416 A1 | 9/2003 | Comper | |
| 2003/0196929 A1 | 10/2003 | Gopinathan | |
| 2004/0049154 A1 | 3/2004 | Larnard | |
| 2004/0167594 A1 | 8/2004 | Elkins | |
| 2004/0210236 A1 | 10/2004 | Allers | |
| 2004/0215163 A1 | 10/2004 | Walker | |
| 2004/0248846 A1 | 12/2004 | Quay et al. | |
| 2005/0152844 A1 | 7/2005 | Barbut et al. | |
| 2005/0154430 A1 | 7/2005 | Barbut et al. | |
| 2005/0209662 A1 | 9/2005 | Lunderqvist et al. | |
| 2006/0052854 A1 | 3/2006 | Allers | |
| 2006/0276552 A1 * | 12/2006 | Barbut | A61F 7/12 514/743 |
| 2007/0123813 A1 * | 5/2007 | Barbut | A61F 7/12 604/19 |
| 2007/0129665 A1 | 6/2007 | Dickens et al. | |
| 2007/0225783 A1 | 9/2007 | Koby et al. | |
| 2008/0004613 A1 * | 1/2008 | Barbut | A61F 7/12 606/21 |
| 2008/0086186 A1 | 4/2008 | Takeda et al. | |
| 2008/0215002 A1 | 9/2008 | Rozenberg | |
| 2008/0249188 A1 * | 10/2008 | Barbut | A61F 7/12 514/759 |
| 2008/0262377 A1 * | 10/2008 | Belson | A61F 7/0085 600/549 |

(56) References Cited

U.S. PATENT DOCUMENTS

| | | | |
|---|---|---|---|
| 2009/0107491 A1* | 4/2009 | Belson | A61F 7/0085 |
| | | | 128/200.14 |
| 2009/0165786 A1* | 7/2009 | Barbut | A61F 7/10 |
| | | | 128/203.12 |
| 2009/0234325 A1* | 9/2009 | Rozenberg | A61F 7/123 |
| | | | 604/514 |
| 2010/0174278 A1 | 7/2010 | Barbut | |
| 2010/0211140 A1 | 8/2010 | Barbut | |
| 2010/0312315 A1 | 12/2010 | Etwil | |
| 2010/0324483 A1* | 12/2010 | Rozenberg | A61M 16/209 |
| | | | 604/98.01 |
| 2010/0324635 A1 | 12/2010 | Kreck | |
| 2011/0028938 A1 | 2/2011 | Barbut et al. | |
| 2011/0226241 A1* | 9/2011 | Stenzler | A61M 16/024 |
| | | | 128/203.12 |
| 2013/0030411 A1 | 1/2013 | Kreck et al. | |
| 2013/0116761 A1 | 5/2013 | Kreck | |
| 2013/0331915 A1* | 12/2013 | Rozenberg | A61F 7/123 |
| | | | 607/105 |
| 2014/0060534 A1* | 3/2014 | Belson | A61F 7/0085 |
| | | | 128/203.15 |

FOREIGN PATENT DOCUMENTS

| | | |
|---|---|---|
| EP | 1888156 | 2/2008 |
| JP | 2005287548 A | 10/2005 |
| WO | WO 98/23217 | 6/1998 |
| WO | WO 01/93922 | 12/2001 |
| WO | WO 03/066137 | 8/2003 |
| WO | WO 2005/070144 | 8/2005 |
| WO | WO 2005/087156 | 9/2005 |
| WO | WO 2006/124702 | 11/2006 |
| WO | WO 2008/063179 | 5/2008 |
| WO | WO 2010/054249 | 5/2010 |
| WO | WO 2010/065616 A1 | 6/2010 |

OTHER PUBLICATIONS

Brain, "Cryosurgery in Benign Condition of the Nose and Throat," *Proc. Roy. Soc. Med.* Jan. 1974; 67(1):72-76.

Hagioka et al., "Nasopharyngeal Cooling Selectively and Rapidly Decreases Brain Temperature and Attenuates Neuronal Damage, Even If Initiated at the Onset of Cardiopulmonary Resuscitation in Rats," *Crit Care Med* 003, vol. 31, No, 10, pp. 2502-2508 (2003).

Harris et al., "Rapid (0.5° C./min) minimally invasive induction of hypothermia using cold perfluorochemical lung lavage in dogs", *Resuscitation* 50 (2001), pp. 189-204.

Mariak et al., "Direct Cooling of the Human Brain by Heat Loss From the Upper Respiratory Tract," *J. App. Physiol.* 87(5): 1609-1613 (1999).

Mellergard, "Changes in Human Intracerebral Temperature in Response to Difference Methods of Brain Cooling," *Neurosurgery*, vol. 31, No. 4, Oct. 1992.

Maloney et al., "Selective Brain Cooling: Role of Angularis Oculi Vein and Nasal Thermoreception," *Am. J. Physiol. Regul. Comp. Physiol.* 273: 1108-1116 (1997).

Natale et al., "Protection From Cerebral Ischemia by Brain Cooling Without Reduced Lactate Accumulation in Dogs," *Stroke*, vol. 20, No. 6, Jun. 1989, pp. 770-777.

Wolfson, M.R. et al., "Intranasal Perfluorochemical spray for Preferential Brain Cooling in Sheep," *Neurocrit Care* 8(3):437-447 (Jun. 2008).

\* cited by examiner

| Q O₂ = 40 L/min | | |
|---|---|---|
| Q liq (mL/min) | Temperature | Observations |
| 10 | 23 | No |
| 20.1 | 13.2 | No |
| 30.8 | 7.2 | No |
| 40.3 | 6.5 | No |
| 50.7 | 7.5 | Yes - slight |
| 60.5 | 8.9 | Yes - stream |
| 70.1 | 10.1 | Yes - stream |
| 80.4 | 10.7 | Yes - spray |
| 90.1 | 11.1 | Yes - spray |
| 100 | 11.5 | Yes - spray |

| Q O₂ = 30 L/min | | |
|---|---|---|
| Q liq (mL/min) | Temperature | Observations |
| 10.1 | 23 | No |
| 20.4 | 16.7 | No |
| 30.3 | 12.7 | No |
| 40.1 | 9.5 | Yes - slight |
| 50.7 | 9.9 | Yes - slight |
| 59.8 | 11.1 | Yes - spray |
| 70.4 | 11.7 | Yes - spray |
| 80.4 | 12.6 | Yes - spray |
| 90 | 12.6 | Yes - spray |
| 100.1 | 13.3 | Yes - spray |

| Q O₂ = 50 L/min | | |
|---|---|---|
| Q liq (mL/min) | Temperature | Observations |
| 10 | 22.2 | No - air |
| 20.8 | 13.2 | No - air |
| 30.5 | 5.3 | No - air |
| 40.6 | 4.9 | No - air |
| 50.2 | 6.6 | No - air |
| 60.9 | 7.7 | Yes- drops |
| 69.6 | 8.4 | Yes - drops/trickle |
| 80.3 | 9.5 | Yes - spray |
| 91.1 | 9.8 | Yes - spray |
| 100.9 | 10.2 | Yes - spray |

FIG. 9

Nasal PFC Spray Cooling Summary

| Run # | PFC | PFC Flow (mL/min) | O2 Flow (L/min) | Bias Flow (L/min) | Cooling Rate (°C/hr) Head–F | Head–V | Head–S | Vasc | Rectal | Notes | V/Q |
|---|---|---|---|---|---|---|---|---|---|---|---|
| 11a | PP1 | 40 | 16 | 8 | 30 | 31 | --- | 10.6 | 2.7 | Head warmed to VASC at 6 minutes | 400 |
| 11b | PP1 | 25 | 18 | 8 | 26 | 26 | --- | 5 | 2.1 | Head warmed to VASC at 12 minutes | 720 |
| 12a | PP2 | 35 | 18 | 8 | 30 | 20 | 12.6 | 3 | 2.8 | Body temp was 1C warmer than first run | 514 |
| 12b | PP2 | 32 | 18 | 8 | 8.6 | 10 | 8.2 | 7.3 | 4.4 | Nasal Prongs w/o CPAP – Head warmed after 12 min | 563 |
| 13a | PP2 | 35 | 20 | 0 | 15.2 | 12.4 | 7.4 | 2.6 | 1.4 | | 571 |
| 13b | PP2 | 26 | 18 | 8 | 20 | 15 | 8 | 2.4 | 2.5 | Cooling slowed after 6 minutes | 692 |
| 14a | PP1 | 19 | 10 | 20 | 17 | 1.3 | 1.4 | 0.6 | 1.3 | Head F warmed after 5 minutes | 526 |
| 14b | PP1 | 47 | 10 | 20 | 3.9 | 3.3 | 3.3 | 1.3 | 1.2 | No rewarming | 213 |
| 14c | PP1 | 39 | 20 | 9 | 5.9 | 5.2 | 6.2 | 1.7 | 1.8 | | 513 |
| 15 | PP1 | 26 | 25 | 20 | | | | | | | 962 |
| 16 | PP1 | 32.8 | 20 | 10 | | | | | | TGI flow decreased after gas on, O₂ changed when PFC added | 610 |

FIG. 37

METHODS AND DEVICES FOR NON-INVASIVE CEREBRAL AND SYSTEMIC COOLING ALTERNATING LIQUID MIST/GAS FOR INDUCTION AND GAS FOR MAINTENANCE

This is a continuation of U.S. application Ser. No. 13/423,561, filed Mar. 19, 2012, which is a continuation-in-part of U.S. application Ser. No. 13/315,141, filed Dec. 8, 2011, now U.S. Pat. No. 8,313,520, which is a continuation of U.S. application Ser. No. 12/825,248, filed Jun. 28, 2010, now U.S. Pat. No. 8,075,605, which is a continuation of U.S. application Ser. No. 11/881,105, filed Jul. 24, 2007, now abandoned, which is a continuation of U.S. application Ser. No. 11/603,846, filed Nov. 22, 2006, now U.S. Pat. No. 7,837,722, which is a continuation-in-part of U.S. application Ser. No. 11/432,285, filed May 10, 2006, now U.S. Pat. No. 7,824,436, which claims the benefit of the following provisional applications: U.S. provisional patent application Ser. No. 60/681,068, entitled "Methods and Devices for Non-Invasive Cerebral and Systemic Cooling," filed May 13, 2005; U.S. provisional patent application Ser. No. 60/717,590, entitled "Methods and Devices for Non-Invasive Cerebral and Systemic Cooling," filed Sep. 16, 2005; and U.S. provisional patent application Ser. No. 60/737,025, entitled "Methods and Devices for Non-Invasive Cerebral and Systemic Cooling," filed Nov. 15, 2005, all of which are expressly incorporated herein by reference in their entirety for all purposes.

FIELD OF THE INVENTION

The invention relates to cerebral and systemic cooling via the nasal cavity, oral cavity, and other parts of the body, and more particularly to methods and devices for cerebral and systemic cooling using liquids or liquid mists with boiling points above body temperature and dry gases and for delivering the liquid mists and/or dry gases to the nasopharyngeal cavity.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Within minutes of circulatory failure, tissues become ischemic, particularly in the heart and brain.

The most common form of shock is cardiogenic shock, which results from severe depression of cardiac performance. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, acutely acquired ventricular septal defects can also cause cardiogenic shock by reducing cardiac output. Additional causes of cardiogenic shock include cardiac arrhythmia, such as ventricular fibrillation. Wish sudden cessation of blood flow to the brain, complete loss of consciousness is a sine qua non in cardiac arrest. Cardiac arrest often progresses to death within minutes if active interventions, e.g., cardiopulmonary resuscitation (CPR), defibrillation, use of inotropic agents and vasoconstrictors such as dopamine, dobutamine, or epinephrine, are not undertakers promptly. The most common cause of death during hospitalization after resuscitated cardiac arrests is related to the severity of ischemic injury to the central nervous system, e.g., anoxic encephalopathy. The ability to resuscitate patients of cardiac arrest is related to the time from onset to institution of resuscitative efforts, the mechanism, and the clinical status of the patient prior to the arrest.

Focal cerebral ischemia refers to cessation or reduction of blood flow within the cerebral vasculature resulting in stroke, a syndrome characterized by the acute onset of a neurological deficit that persists for at least 24 hours, reflecting local involvement of the central nervous system. Approximately 80% of the stroke population is hemispheric ischemic strokes, caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. Hemorrhagic stroke accounts for the remaining 20% of the annual stroke population. Hemorrhagic stroke often occurs due to rupture of an aneurysm or arteriovenous malformation bleeding into the brain tissue, resulting in cerebral infarction. Other causes of focal cerebral ischemia include vasospasm due to subarachnoid hemorrhage from head trauma or iatrogenic intervention.

Current treatment for acute stroke and head injury is mainly supportive. A thrombolytic agent, e.g., tissue plasminogen activator (t-PA), can be administered to non-hemorrhagic stroke patients. Treatment with systemic t-PA is associated with increased risk of intracerebral hemorrhage and other hemorrhagic complications. Aside from the administration of thrombolytic agents and heparin, there are no therapeutic options currently on the market for patients suffering from occlusion focal cerebral ischemia. Vasospasm may be partially responsive to vasodilating agents. The newly developing field of neurovascular surgery, which involves placing minimally invasive devices within the carotid arteries to physically remove the offending lesion, may provide a therapeutic option for these patients in the future, although this kind of manipulation may lead to vasospasm itself.

In both stroke and cardiogenic shock, patients develop neurological deficits due to reduction in cerebral blood flow. Thus treatments should include measures to maintain viability of neural tissue, thereby increasing the length of time available for interventional treatment and minimizing brain damage while waiting for resolution of the ischemia. New devices and methods are thus needed to minimize neurologic deficits in treating patients with either stroke or cardiogenic shock caused by reduced cerebral perfusion.

Research has shown that cooling the brain may prevent the damage caused by reduced cerebral perfusion. Initially research focused on selective cerebral cooling via external cooling methods. Studies have also been performed that suggest that the cooling of the upper airway can directly influence human brain temperature, see for example *Direct cooling of the human brain by heat loss from the upper respiratory tract*, Zenon Mariak, et al. 8750-7587 *The America Physiological Society* 1999, incorporated by reference herein in its entirety. Furthermore, because the distance between the roof of the nose and the floor of the anterior cranial fossa is usually only a fraction of a millimeter, the nasal cavity might be a site where respiratory evaporative heat loss or convection can significantly affect adjacent brain temperatures, especially because most of the warming of inhaled air occurs in the uppermost segment of the airways. Thus, it would be advantageous to develop a device and method for achieving cerebral cooling via the nasal and/or oral cavities of a patient.

SUMMARY OF THE INVENTION

The invention relates to methods, devices, and compositions for cerebral cooling, preferably via the nasal and/or oral cavities. The cooling occurs by direct heat transfer through the nasopharynx as well as by hematogenous cooling through the carotids as they pass by the oropharynx and through the Circle of Willis, which lies millimeters away from the pharynx. The direct cooling will be obtained through evaporative heat loss of a nebulized liquid in the nasal cavity, oral cavity, and/or throat. Additionally, cooling may occur through convection in the nasal cavity. Such cerebral cooling may help to minimize neurologic deficits in treating patients with either stroke or cardiogenic shock caused by reduced cerebral perfusion or in the treatment of migraines. In the following description, where a cooling assembly, device, or method is described for insertion into a nostril of a patient, a second cooling assembly or device can optionally also be inserted into the other nostril to maximize cooling. Among the many important advantages of the present invention is patient safety by comparison with transpulmonary and intravascular cooling methods and devices.

In one embodiment, the invention provides a method for cerebral cooling. An elongate member can be inserted into a nasal cavity of a patient through the patient's nostril. The elongate member has a proximal end, a distal end, a first lumen extending therebetween, and it plurality of ports in fluid communication with the first lumen. This device can be used to alternate between delivery of a wet gas (nebulized liquid coolant and a substantially dry gas) and dry gas (substantially dry gas substantially free of liquid) for nasal cooling. After inserting the device, a nebulized liquid coolant and a substantially dry gas are then delivered in combination onto a surface of the patient's nasal cavity through the plurality of ports in the elongate member for a period of between about 10 minutes to 9 hours. A substantially dry gas substantially free of liquid is then delivered onto a surface of the patient's nasal cavity through the plurality of ports in the elongate member for a period of between about 10 minutes to 240 hours.

During delivery of wet gas, the liquid coolant is nebulized at the plurality of ports within the nasal cavity and the delivery of the substantially dry gas in combination with the nebulized liquid coolant enhances evaporation of the liquid coolant from the nasal cavity to reduce the cerebral temperature of the patient. In some embodiments, the evaporation of the liquid coolant in the nasal cavity, which is enhanced by the substantially dry gas, results in reduction of the cerebral temperature of the patient by between about 0.1 to 5.0° C./hr. In some embodiments, the step of delivering the substantially dry gas substantially free of a liquid is administered first to reduce the patient's cerebral temperature and the step of delivering a nebulized liquid coolant and a substantially dry gas in combination initiated subsequently to further reduce the patient's cerebral temperature to between about 18 to 36° C. The method may further include repeating the step of delivering a substantially dry gas substantially free of a liquid onto the surface of the patient's nasal cavity through the plurality of ports in the elongate member for a period of between about 10 minutes to 10 days to prevent rewarming of the cerebral temperature of the patient. For example, in some embodiments, repeating the step of delivering a substantially dry gas substantially free of a liquid onto the surface of the patient's nasal cavity may be initiated when the patient's brain has been cooled to a temperature of about 18 to 36° C. The method may further comprise repeating the step of delivering a nebulized liquid coolant and a substantially dry gas in combination onto a surface of the patient's nasal cavity for a period of between about 10 minutes to 9 hours to maintain a cerebral temperature of between about 18 to 36° C.

In alternative embodiments, the method may be used for about 6 hours while the patient is transitioning from nasal cooling to systemic cooling, such as surface cooling or intravascular cooling. In some embodiments, the gas may be dry air or one of its components. Alternatively, the gas may be oxygen, a noble gas, or an anesthetic agent. In some embodiments, the gas may be delivered at a one of between about 20 to 100 L/min. In some embodiments, the liquid coolant may be a perfluorocarbon. Additionally, the perfluorocarbon may have a boiling point above 37° C., alternatively between about 0° C. and about 160° C., alternatively between about 25° C. and about 140° C.

In another embodiment, the invention provides an alternative method for cerebral cooling. An elongate member can be inserted into a nasal cavity of a patient through a patient's nostril. The elongate member may have a proximal end, a distal end, a first lumen extending therebetween, and a plurality of posts in fluid communication with the first lumen. A nebulized liquid coolant and a substantially dry gas are can be delivered in combination onto a surface of the patient's nasal cavity through the plurality of ports in the elongate member for a period of between about 10 minutes to 9 hours. The liquid coolant is nebulized at the plurality of ports within the nasal cavity and the gas enhances evaporation of the liquid coolant from the nasal cavity to further reduce the cerebral temperature of the pattern. A substantially dry gas substantially free of liquid can be delivered onto a surface of the patient's nasal cavity through the plurality of ports in the elongate member for a period of between about 10 minutes to 10 days. The patient's temperature can be measured and the delivery of the nebulized liquid coolant can be adjusted in response to the patient's temperature. In some embodiments, the patient's temperature may be measured by measuring one of the patient's cerebral temperature, esophageal temperature, tympanic temperature, body temperature, bladder temperature, blood temperature, or rectal temperature. The step of measuring the patient's temperature may further comprise continuously monitoring the patient's core temperature.

In some embodiments, the delivery of the nebulized liquid coolant can be stopped in response to the patient's temperature. Delivery of the nebulized liquid coolant in combination with the substantially dry gas can then be repeated for a period of between about 10 minutes to 9 hours to prevent rewarming of the cerebral temperature of the patient. For example, some embodiments, further comprise the step of setting a target temperature for the core temperature of no lower than 30° C., and then delivering the nebulized liquid coolant and a substantially dry gas in combination onto the surface of the patient's nasal cavity until the core temperature reaches the target temperature. For example, an operator may set the target core temperature within the range of about 30 to 37° C. In some embodiments, the step of delivering a substantially dry gas substantially free of a liquid onto a surface of the patient's nasal cavity can then be automatically repeated when the patient's core temperature reaches the target temperature. In some embodiments, the step of delivering a nebulized liquid coolant and a substantially dry gas in combination onto a surface of the patient's nasal cavity can be automatically repeated when the patient's core temperature rises more than 0.1° C. above the target temperature. Alternatively, the step of adjusting delivery of the nebulized liquid coolant can comprise repeating delivery of the nebulized liquid coolant and a substantially dry gas in combination onto a surface of the patient's nasal cavity when the patient's core temperature reaches substantially greater than the target temperature. In an alternative embodiment, a target temperature for the pattern's cerebral temperature can be set within a range of about 18-36° C., and the step of delivering the nebulized liquid coolant and a substantially dry gas in combination may further comprise intermittently delivering a nebulized liquid coolant and substantially dry gas in combination onto the surface of the patient's nasal cavity to maintain the patient's cerebral temperature within ±0.5° C. of the target temperature.

In some embodiments, the step of delivering the substantially dry gas substantially free of a liquid is administered first to reduce the patient's cerebral temperature and the step of delivering a nebulized liquid coolant and a substantially dry gas in combination can then be initiated subsequently to further reduce the patient's cerebral temperature to a temperature of between about 30 to 36° C. The step of delivering a substantially dry gas substantially free of a liquid onto a surface of the patient's nasal cavity may then be repeated for a period of between about 10 minutes to 10 days to maintain a cerebral temperature of between about 18 to 36° C.

In another embodiment, a medical device for cerebral cooling is provided. The medical device comprises an elongate tubular member capable of delivering a gas only or a gas in combination with a liquid coolant to a patient's nasal cavity, a liquid coolant source, a compressed gas source, and a switch for alternately connecting the liquid coolant source. The elongate tubular member has proximal and distal ends and an outer wall having a plurality of delivery ports. First and second lumens extend from a proximal region of the elongate tubular member to the delivery ports and are in fluid communication with the delivery ports. The gas source is in fluid communication with the first lumen and the switch alternately connects the liquid coolant source to the second lumen so that the first lumen transports a compressed gas to the delivery ports and the second lumen transports a liquid coolant to the delivery ports. In some embodiments, a plurality of mixing channels extend between the plurality of delivery ports and the first lumen and a plurality of connecting tubes extend between the mixing channels and the second lumens. The first and second lumens are arranged such that in use the liquid coolant an compressed gas are separately transported from the proximal end of the elongate tubular member to the plurality of delivery ports on the outer wall.

In an alternative embodiment, the invention provides a method for cerebral cooling. An elongate member can be inserted into a nasal cavity of a patient through the patient's nostril. The elongate member may have a proximal end, a distal end, a first lumen extending therebetween, and a plurality of ports in fluid communication with the first lumen. A substantially dry gas is then delivered onto a surface of the patient's nasal cavity through the plurality of ports in the elongate member at a flow rate of between about 20 to 100 L/min. In some embodiments, the method may occur for about 6 hours when the patient is transitioning from nasal cooling to surface or intravascular cooling.

The volume of liquid delivered may range from about 0.1 to about 20 liters, alternatively about 1 to about 20 liters, alternatively about 1 to about 15 liters, alternatively about 1 to about 10 liters, alternatively about 1 to about 8 liters, alternatively about 2 to 6 liters. Unevaporated liquid may also be suctioned or otherwise removed from the patient's nasal pharynx. A cooling helmet may also be used to help lower the cerebral temperature of the patient. Furthermore, a warming blanket may be used to maintain the systemic temperature of the patient, or prevent the systemic temperature from decreasing as much as the cerebral temperature. A vasodilator may also be delivered to the patient's nasal cavity to enhance vascular cooling capacity. Additionally or alternatively, a humidifier, such as isotonic saline or water, may also be delivered into the patient's nasal cavity. Additional air or oxygen may be delivered to the patient to enhance the evaporative process through a mask placed over the nose of the patient, such as a CPAP nasal mask.

The patient's cerebral, systemic, and nasal temperatures may also be monitored during this method. The nebulized spray may be delivered at a flow rate sufficient to achieve a gradient of not greater than about 0.5° C. between the outer surface of the brain and the inner core of the brain. The nebulized spray may also be delivered at a flow rate sufficient to achieve a gradient of at least about 1.0° C. between the cerebral temperature and the systemic temperature. The nebulized spray may also be delivered at a flow rate sufficient to achieve cerebral cooling at a rate greater than about 1.0° C. in hour. The nebulized spray may also be delivered at a flow rate sufficient to achieve a temperature in the nasal cavity of about 4.0° C. or less.

In an alternative embodiment according to this invention, a nasal catheter may be used to deliver a spray of liquid to the nasal cavity of a patient. The nasal catheter may be placed in the nares of the patient's nose and may be angled to direct the spray outlet at the desired structures of the nose, for example, the nasal conchae. In addition, the distal end of the nasal catheter and may be designed to cause the spray to spread in a pattern which will allow the gas and liquid mixture to contact as much of the desired tissue as possible. Spreading the spray will also minimize the potential of medical trauma that could result form a high velocity stream of liquid directed at the tissue of the nasal cavity. In addition, the distal end of the catheter may be 'tipped', i.e., sealed of in a rounded fashion to provide a smooth surface to avoid damaging the sensitive nasal tissues.

A number of methods for spreading the spray pattern are contemplated. For example, the spray pattern may be formed by creating one or more holes along opposite sides of the catheter tip, which would create a broad, flat spray perpendicular to the axis of the catheter. This pattern may be further altered by changing the size, location and number of holes in the catheter. In addition, this patient may further include a hole in the tip of the catheter to produce some additional flow in the axial direction. An alternative spray pattern may be formed by making a slit in the tip of the catheter to produce a fan shaped spray centered on the axial direction of the catheter. This pattern maybe further altered by varying the width of the slit and the length the slit extends down the sides of the catheter. In addition, multiple, intersecting slits may be made in the catheter tip. Another alternative spray pattern may be formed by making a straight or carved cut along opposite sides of the catheter wall. The skived cut may extend front and include a portion of the tip. This configuration will produce a wide 'fan' shaped spray covering a broad angle from the perpendicular to the axial direction of the catheter. In addition, any of the above described patterns could be combined to create additional spray patterns for the nasal catheter.

In some embodiments, the patient's nasal cavity may be pre-sprayed with an anesthetic, such as lidocaine or neurotensin, to anesthetize the trigeminal nerve endings prior to initiating cooling in order to prevent any sensation of the cooling which could be interpreted by the patient as pain.

The compositions of the invention include liquids having a boiling point of 38-300° C., more preferably a boiling point of 38-200° C., more preferably a boiling point of 60-150° C., more preferably a boiling point of 70-125° C., more preferably a boiling point of 75-110° C., more preferably a boiling point of 60-70° C. Compounds having suitable characteristics for use herein include hydrocarbons, fluorocarbons, perfluorocarbons, and perfluorohydrocarbons. Saline is another example of a substance having suitable characteristics for use herein. As used in this specification, the terms "fluorocarbon,", "perfluorocarbon," and "perfluorohydrocarbon" are synonymous. In addition to containing carbon and fluorine, these compounds may also contain other atoms. In one embodiment, the compounds could contain a heteroatom, such as nitrogen, oxygen, or sulfur, or a halogen, such as bromine or chlorine. These compounds may be linear, branched, or cyclic, saturated or unsaturated, or any combination thereof.

In another embodiment, the compounds are highly fluorinated compounds, which are compounds containing at least three fluorine atoms. These highly fluorinated compounds may also contain other atoms besides carbon and fluorine. These other atoms include, but are not limited to, hydrogen; heteroatoms such as oxygen, nitrogen, and sulfur; and halogens such as bromine or chlorine. In one embodiment, the number of the atoms that are not carbon or fluorine comprise a minority of the total number of atoms in the compound. These highly fluorinated compounds may be linear, branched, or cyclic, saturated or unsaturated, or any combination thereof. Examples of these compounds include, but are not limited to, $C_4F_9Br$ (b.p. 43° C.), $CF_3CF(CF_3)CF=CF_2$ (b.p. 51° C.), or $CF_3CF(CF_3)CH=CH_2$.

In another embodiment, the compounds are hydrofluorocarbons, which are compounds where the number of hydrogen atoms exceeds the number of fluorine atoms. These hydrofluorocarbons may also contain other atoms besides hydrogen, carbon, and fluorine. These other atoms include, but are not limited to, heteroatoms such as oxygen, nitrogen, and sulfur and halogens such as chlorine and bromine. For example, hydrofluorocarbons include, but are not limited to, hydrochlorofluorocarbons, more specifically, hydrochlorofluoroalkanes. In one embodiment, the number of the atoms other than carbon and fluorine comprise a minority of the total number of atoms in the compound. These hydrofluorocarbons may be linear, branched, or cyclic, saturated or unsaturated, or any combination thereof.

A mixture of two or more highly fluorinated compounds hydrofluorocarbons, light fluorocarbons, hydrocarbons, fluorocarbons, perfluorocarbons, perfluorohydrocarbons, or any of the above-mentioned compounds may also be used. The mixture may contain any of the previously mentioned compounds in different phases (e.g., one gas, one liquid). The mixture has a boiling point above 37° C., even though any individual component of the mixture may have a boiling point below 37° C.

Light fluorocarbons are fluorocarbons that have a boiling point below 37° C. These light fluorocarbons may also contain other atoms besides carbon, and fluorine. These other atoms include, but are not limited to, hydrogen; heteroatoms such as oxygen, nitrogen, and sulfur: and halogens such as chlorine and bromine. For example, light fluorocarbons include, bat are not limited to perfluorobutane and perfluoropentane. In one embodiment, the number of the atoms other than carbon and fluorine comprise a minority of the total number of atoms in the compound. These light fluorocarbons may be linear, branched, or cyclic, saturated or unsaturated, or any combination thereof.

Nitric oxide or adrenergic agents, such as adrenaline (epinephrine) or albuterol, may be added in minute doses to the compositions described in any of the previously described embodiments. The NO or other agent is inhaled and acts as a potent nasal vasodilator, which improves the rate of action of the cooling mist and counteracts nasal vasoconstriction caused by administering cold substances to the nasal cavity. The NO may be included in an amount of about 2 to about 80 parts per million, in other cases in an amount of about 3 to about 20 parts per million, in other cases in an amount of about 4 to about 10 parts per million, in other cases in an amount of about 5 to about 8 parts per million, in other cases in an amount of about 5 parts per million.

In other methods, administration of cold mists will occur in cycles with intervening cycles of administering another gas, preferably a cold dry gas such as dry air or dry heliox, e.g., a mixture of helium and oxygen. With continuous administration of perfluorocarbon mist, the gaseous phase in the nasal cavity may become saturated with gaseous PFC, thereby slowing the rate of evaporative heat loss. In order to accelerate the rate of evaporative heat loss, it may be desired to periodically purge the nasal cavity of perfluorocarbon. This can be done by cycling administration of cold mists with administering another gas, preferably a dry gas such as dry air or dry heliox.

Where cycling is desired, it is recommended that the cycles occur for about 3 seconds or more, in other cases for about 30 seconds or more, in other cases for about one minute of more, in other cases for about two minutes or more, in other cases for about five minutes or more, in other cases for about ten minutes or more, in other cases for about 30 minutes or more. The intervening cycle of dry gas may last for an equal period (e.g., about 3 seconds of cold mist followed by about 3 seconds of dry gas, about 30 seconds of cold mist followed by about 30 seconds of dry gas, about one minute of cold mist followed by about one minute of dry gas, about two minutes of cold mist followed by about two minutes of dry gas, about five minutes of cold mist followed by about five minutes of dry gas, about ten minutes of cold mist followed by about ten minutes of dry gas, about 30 minutes of cold mist followed by about 30 minutes of dry gas, or for a shorter or longer period (about ten minutes of cold mist followed by about two minutes of dry gas).

BRIEF DESCRIPTION OF THE DRAWINGS

FIG. 2A an embodiment of a device having multiple ports for separately transporting a gas and a liquid to the nasopharyngeal cavity and a switch for selectively connecting the liquid source to the device according to the present invention for non-invasive cerebral and systemic cooling

FIG. 9 is a table of parameters and results for cerebral cooling trials performed wherein the compressed gas flow rate was maintained while the liquid flow rates were varied.

FIG. 37 is a table of experimental date from cerebral cooling trials performed wherein the cooling liquid used and the flow rate were varied.

DETAILED DESCRIPTION

Evaporative Cooling in the Nasal Cavity

Targeted cerebral cooling via cooling of the nasal and or oral cavities is possible because of the both direct heat transfer due to the proximity of the brain and hematogenous cooling through the carotids s they pass by the oropharynx and through the Circle of Willis, which lies millimeter away from the pharynx. The direct cooling is obtained through evaporative heat loss in the nasal cavity. The evaporative heat loss in the nasal cavity further results in convective cooling of the brain and eventually core body temperature.

Evaporative heat loss in the nasal cavity can be achieved by spraying high volume air, or any other suitable substantially dry gas, into the patient's nasal cavity to evaporate the naturally occurring fluid in the nasal cavity. Such forced evaporative cooling is minimally invasive and can be done without the need for airway protection in a non-medical or field setting. Alternatively, delivering and evaporating a liquid coolant in the patient's nasal cavity achieves more substantial evaporative heat loss. For example, a liquid coolant can be delivered to the patient's nasal cavity in combination with the substantially dry gas such that the gas enhances the evaporation of the liquid coolant in the patient's nasal cavity resulting in cooling due to the evaporative heat loss of the liquid coolant in the nasal cavity. Such a method will result in much more intense cooling, however, patients may need to be intubated and/or sedated before such "wet" cooling can be initiated.

Figure 1:
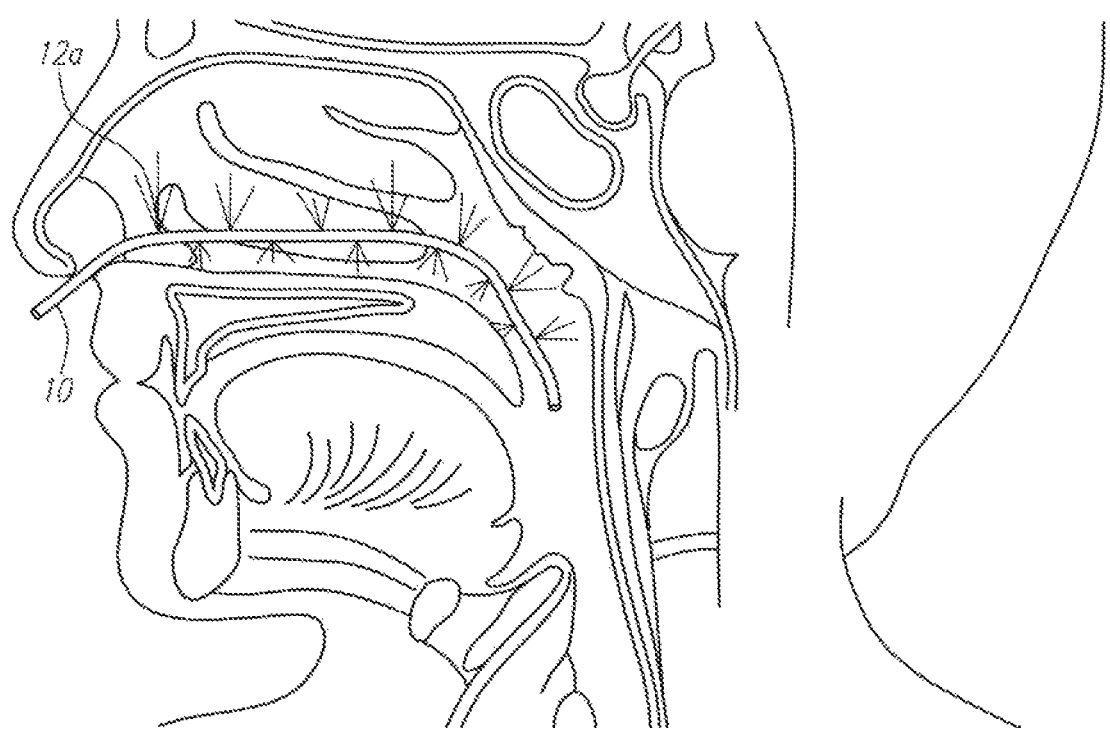
FIG. 1 illustrates an embodiment of a device having multiple ports for delivering a liquid inserted into the nasopharyngeal cavity according to the present invention for non-invasive cerebral and systemic cooling.
Figure 2:
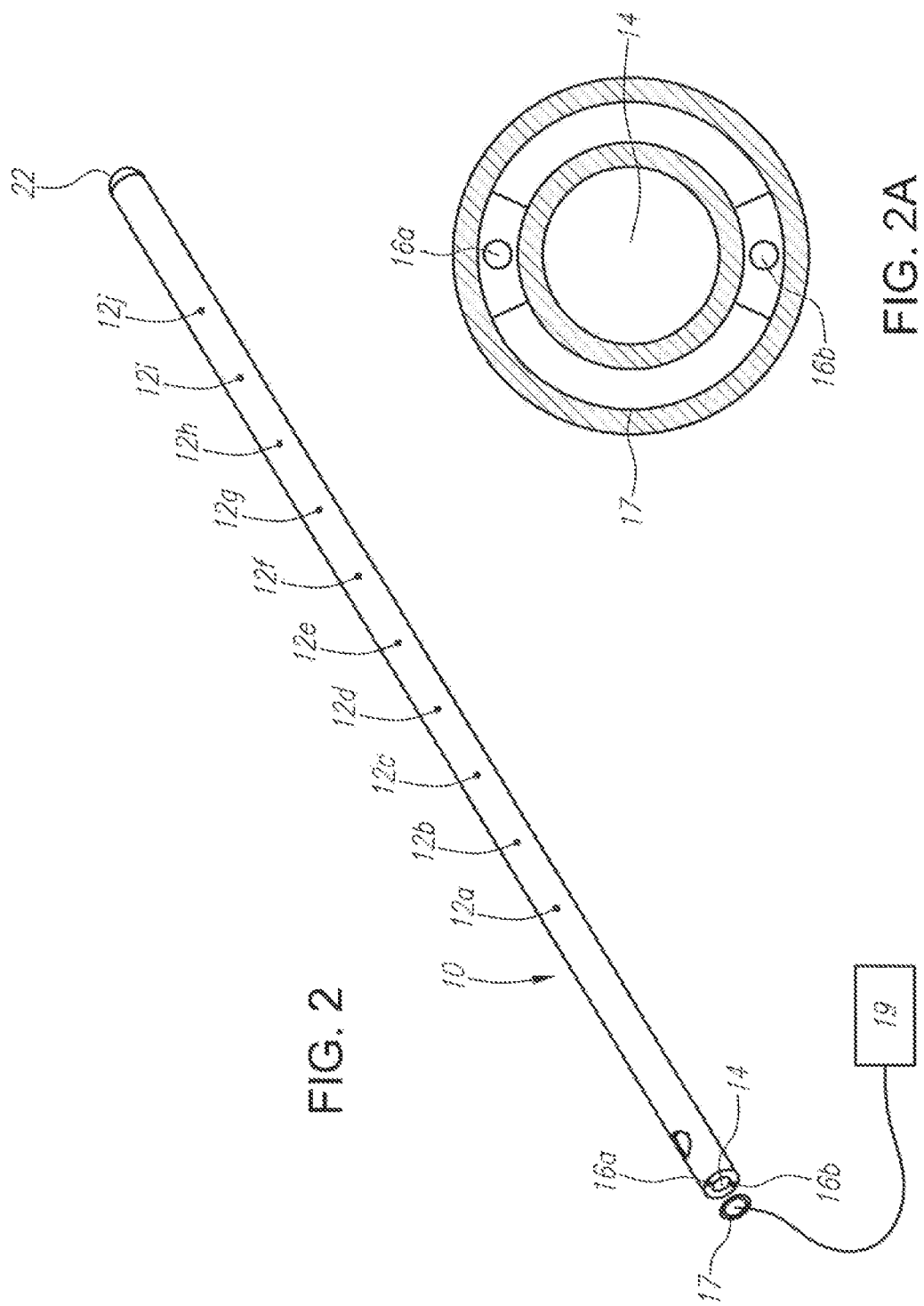
FIG. 2 illustrates an embodiment of a device having multiple ports for delivering a liquid to the nasopharyngeal cavity according to the present invention for non-invasive cerebral and systemic cooling.
Figure 3:
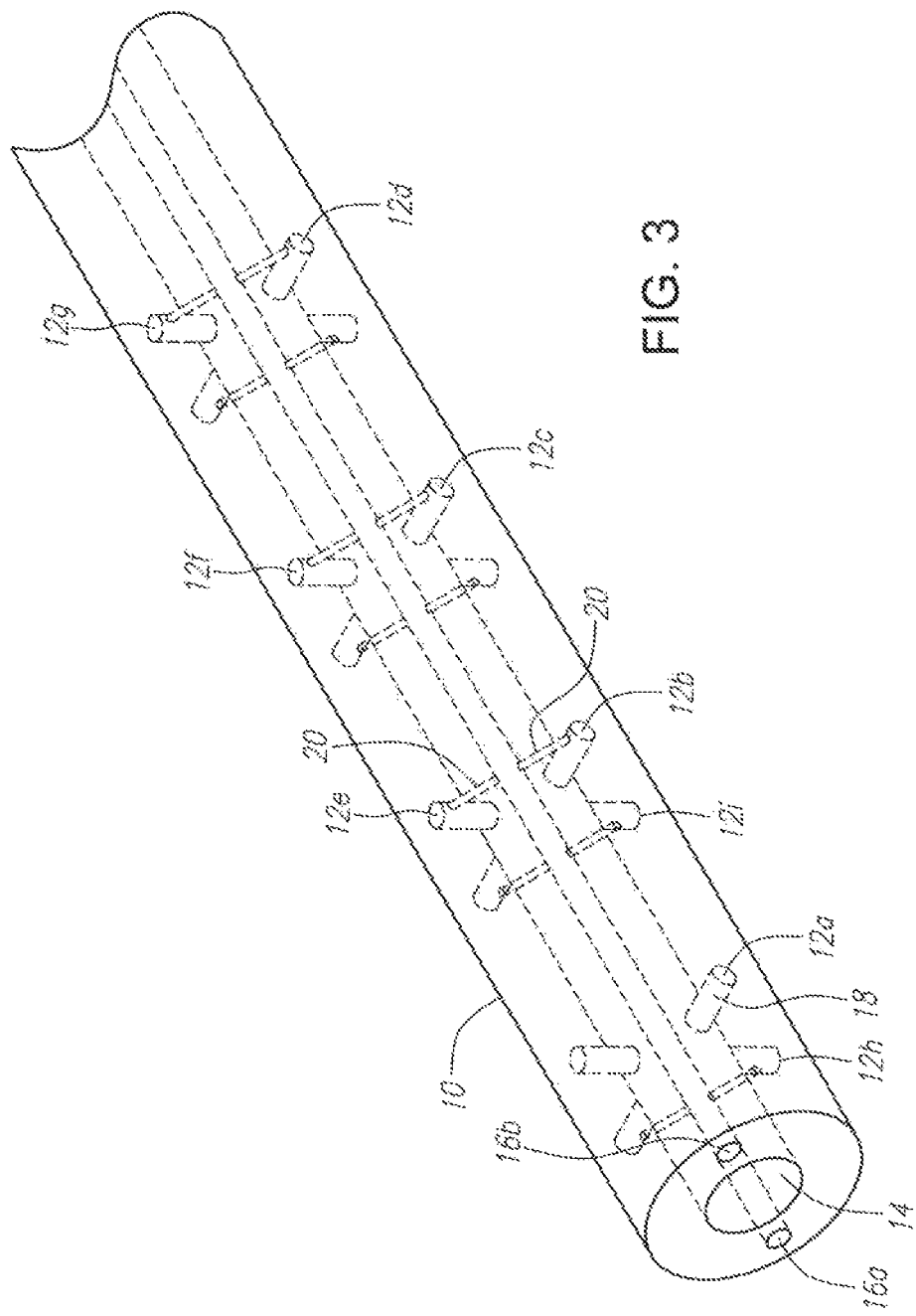
FIG. 3 illustrates an embodiment of a device having multiple ports for delivering a liquid to the nasopharyngeal cavity according to the present invention for non-invasive cerebral and systemic cooling.
Figure 4:
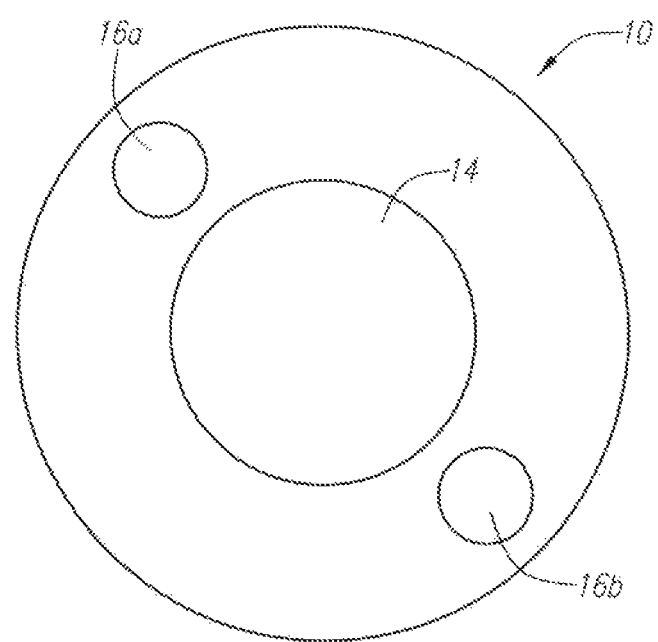
FIG. 4 illustrates a cross-section of a nasal catheter having a plurality of lumens for separately transporting a liquid and a compressed gas according to the present invention.
Figure 5:
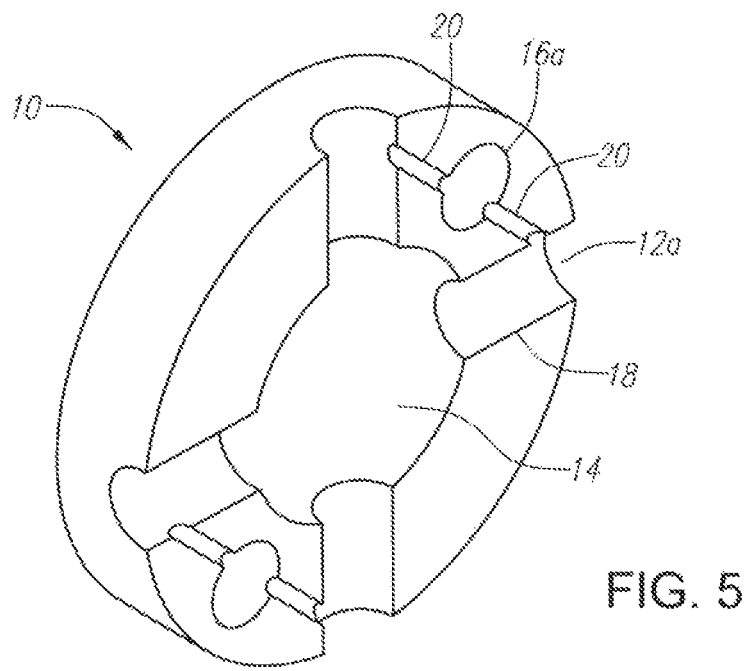
FIG. 5 illustrates a cross-section of a nasal catheter having a plurality of ports for separately nebulizing a liquid and delivering a nebulized liquid spray to the nasal cavity according to the present invention.
Figure 6A:
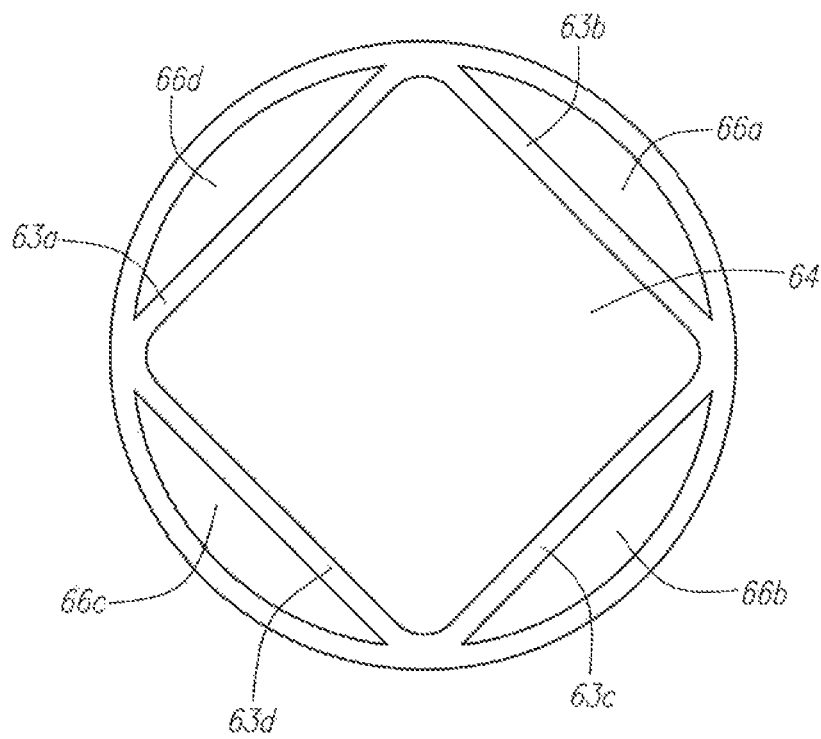
FIG. 6A illustrates a cross-section of an alternative embodiment of nasal catheter having a plurality of lumens for separately transporting a liquid and a compressed gas according to the present invention.
Figure 6B:
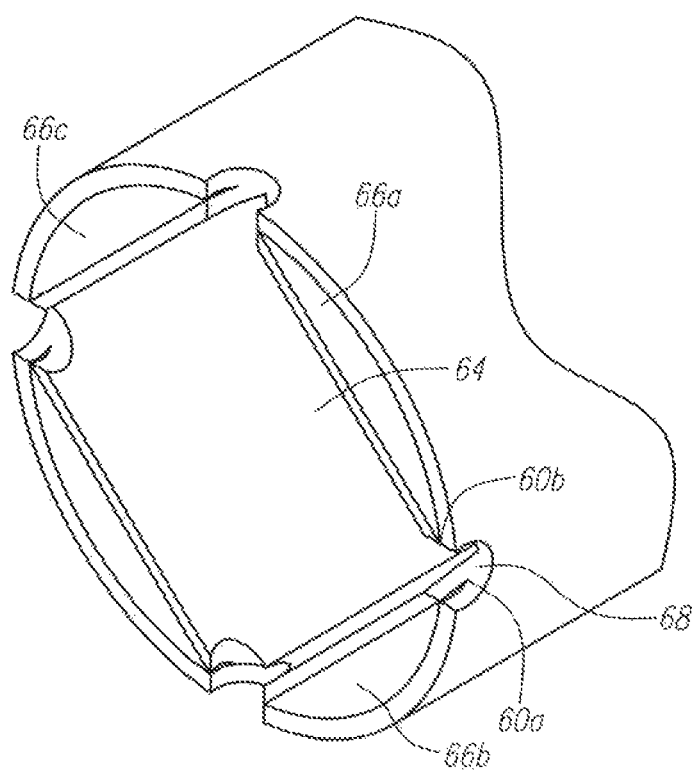
FIG. 6B illustrates a cross-section of an alternative embodiment of a nasal catheter having a plurality of ports for nebulizing a liquid and delivering a nebulized liquid spray to the nasal cavity according to the present invention.

FIGS. 1-3 illustrate nasal catheter 10 with multiple delivery ports 12*a-m* for non-invasive cerebral and systemic cooling of the nasal cavity. Nasal catheter 10 is operably sized to extend through the patient's nasal cavity and into the nasal pharynx and has a plurality of lumens 14 and 16*a-b* extending between the proximal and distal ends of catheter 10 for separately delivering a liquid and a compressed gas. Nasal catheter 10 also has rounded sealed tip 22 on the distal end, which seals the distal end of lumens 14 and 16*a-b* and provides a smooth surface to avoid damaging sensitive tissues. FIGS. 4-7 depict several possible designs for the lumens of nasal catheter 10. FIG. 4 shows catheter 10 with a large, circular central lumen 14 that may be used for transporting the compressed gas through catheter 10 while one or more smaller lumens 16*a-b* may be used for transporting the liquid through catheter 10. In FIGS. 6-8, more complex, geometric extruded tubes are used to simplify the mixing process at each delivery port. In FIGS. 6A-B, square central lumen 64 is provided for transporting the compressed gas through the catheter while the liquid may be transported in four outer sections 66*a-d*. FIGS. 7A-D depict an alternative embodiment where the gas lumen is a central geometric shape 74 and the four outer sections 76*a-d* form the channels for transporting the liquid. In an alternative embodiment, additional lumens (not shown) may be provided, for example, to permit inflation of an expandable member located on the distal end of the catheter or to permit suction of the non-evaporated liquid from the nasal cavity.

As shown in FIG. 3, a plurality of ports 12*a-m* are located along the outer wall of catheter 10. These ports 12*a-m* are spaced apart longitudinally and axially along the outer walls of catheter 10 and are in fluid communication with lumens 14 and 16*a-b* transporting the liquid and compressed gas through catheter 10. For example, there may be about 10-40 delivery ports distributed around the circumference of the catheter and spaced apart to cover the distance from about 3 cm to about 12 cm along the length of catheter 10. In use, when catheter 10 is placed in the nasal cavity of a patient, this distribution would provide full coverage of the nasal cavity. Furthermore, each delivery port will be designed so that the liquid and gas flowing through the catheter lumens will be combined near the delivery port and the liquid will then be nebulized just prior to entering the nasal cavity. As shown in FIG. 5, each of ports 12*a-m* is formed by drilling mixing channel 18 in the outer wall of nasal catheter 10 connecting to central lumen 14 transporting the compressed gas. In addition, separate liquid connecting tubes 20 are formed in the outer wall of catheter 10 to connect liquid lumens 16*a-b* with each of mixing channels 18 drilled between ports 12*a-b* and compressed gas lumen 14. This provides for the ability to separately nebulize the liquid into a spray at each delivery port. Specifically, mixing channels 18 to provide for gas flow outward from central gas lumen 14 while liquid connecting tubes 20 permit addition of the liquid to the gas stream in channel 18. At this point, the gas is moving at a high velocity and the liquid experiences high shear forces, breaking the liquid stream into small droplets and creating a nebulized liquid for delivery via ports 12*a-b*. The inner diameter of connecting tubes 20 and the shape and size of the ports 12*a-b* are important parameters and may be altered to vary the size of the liquid droplets and to optimize the spray pattern of delivery ports 12*a-b*.

In addition, in some embodiments, as shown in FIG. 2A, a switch 17 may be provided to alternately connect and disconnect the source of liquid coolant to the liquid lumens 16*a,b* so that the same catheter 10 can be used to either deliver the gas alone to the patient's nasal cavity through the ports 12*a-j*, or alternatively, to deliver the gas combination with the nebulized liquid coolant to the patient's nasal cavity through ports 12*a-j*. The switch 17 may be located in the proximal end of the catheter 10, as shown, or alternatively, the switch may be located at any point in the system between the source of liquid coolant and the liquid lumens 16*a-b*. In use, the catheter 10 can be used on a patient in a field or non-medical setting to deliver a substantially dry gas to the patient's nasal cavity to provide cooling due to the evaporative heat loss of naturally occurring fluids in the patient's nasal cavity. A dry gas source is connected to gas lumen 14 of catheter 10 and delivered at a high volume flow rate of between about 20-100 L/min, alternatively between about 40-100 L/min, alternatively between about 50-90 L/min, alternatively between about 60-80 L/min to cause evaporative cooling in the nasal cavity which results in cerebral cooling of between about 0.1 to 1° C./hour. The dry gas source may be compressed or non-compressed. Dry gases, which can be used with this method, include air or any one of its components, oxygen, or a noble gas, such as Helium or Argon. In some embodiments, the dry gas may be an anesthetic agent, such as $N_2O_2$ or Xe, which may have additional neuroprotective properties. The substantially dry gas contains substantially no water vapor, and preferably has a relative humidity of less than about 20%, alternatively 10%, alternatively 5%, 2%, alternatively 1% alternatively 0.5%, alternatively 0.1%.

The dry gas only cooling, i.e. "dry" cooling, may be administered for a period of between about 10 minutes to 240 hours to reduce and/or maintain the patient's cerebral temperature. If it is determined that more intense brain cooling is required, for example once the patient reaches the hospital, switch 17 may be engaged to connect a source of liquid coolant to catheter 10 and begin cooling using a combination of the liquid coolant and the dry gas. The liquid coolant is transported through liquid lumens 16*a,b* of catheter 10 and nebulized at the plurality of delivery ports 12*a-j* by gas delivered through gas lumen 14, as described above, prior to delivery onto the surface of the patients nasal cavity. The dry gas is also used to enhance evaporation of the nebulized liquid coolant in the nasal cavity. In some embodiments, the patient may be intubated prior to initiating delivery of the liquid coolant in order to prevent non-evaporated coolant from reaching the lungs in large quantities. In addition, the patient may also be sedated to facilitate delivery of the liquid coolant.

The combination of the nebulized liquid coolant and dry gas, i.e. "wet" cooling, provides significantly more cooling that gas only cooling due to the evaporative heat loss of the nebulized liquid coolant in the nasal cavity. For example, the cerebral temperature of the patient may be reduced from between about 0.1 to 5.0° C./hour, alternatively from between about 0.5 to 4.0° C./hour, alternatively from between about 1.0-3.5° C./hour. This "wet" cooling is administered for between about 10 min to 9 hours to reduce the patient's cerebral temperature to between about 18 to 36° C. Once the desired brain cooling has been achieved, the "wet" cooling may be continued to maintain the patient's cerebral temperature at the desired temperature. Alternatively, the cooling method may be switched back to the "dry" mode of cooling, i.e. gas only cooling, to maintain the brain at the reduced temperature for a prolonged period of time. For example, once the patient's cerebral temperature is reduced to between about 18 to 36° C., the liquid coolant may be disengaged by using switch 17 to disconnect fluid communication between the liquid coolant source and liquid lumens 16*a,b*. Catheter 10 then reverts to delivering only dry gas through 12*a-j*. It may require far fewer watts of energy to maintain the reduced temperature, and, therefore the evaporative heat loss due to the dry gas evaporating naturally occurring fluids may be sufficient to maintain the reduced brain temperature for a period of between about 10 minutes to 240 hours, or longer if necessary.

If the brain temperature starts rising the "dry" cooling, the liquid coolant may be reengaged to initiate "wet" cooling again for a period of time sufficient to reduce the cerebral temperature back to the desired level. It may be that only a short period of "wet" cooling, such as between about 10-30 min, alternatively between about 5-60 min, is necessary to reduce the temperature back down to the desired level. Accordingly, in some embodiments, the "wet" cooling can be intermittently activated, for example by using switch 17 to reconnect the liquid coolant source to catheter 10, for a short period of lime to maintain the patient's cerebral temperature is the desired reduced temperature for a prolonged period of time, using primarily "dry" cooling, which has the advantage of being much more cost effective. In addition, this method obviates the need to switch to another cooling device or method, such as an external cooling blanket or an intravascular cooling catheter, for maintaining the cooling for a prolonged period of time, as currently done.

In some embodiments, such as depicted in FIG. 2A, a control unit 19 may be provided to allow an operator to activate switch 17 to turn on or on the liquid flow from the liquid coolant source. The control unit 19 may also include software and a processor which allow if to be used in conjunction with one or mote temperature sensors to automatically control the cooling therapy received by the patient based on the feedback regarding the temperature of the patient and a pre-determined desired temperature or temperature range set by the operator. In use, as shown in FIG. 50, at step 1000, "dry" cooling only of the patient's nasal cavity is initiated as described above, to initially begin cerebral cooling, for example in a non-medical setting. Once the patient is brought into the hospital, a determination is made as to whether the patient needs more intense brain cooling. For example, as depicted in step 1002, the patient's temperature may be measured to make the determination regarding whether additional cooling is needed, alternatively, other factors may be used to assess whether additional cooling is needed. The patients temperature may be measured by measuring one or more of the patient's cerebral esophageal, tympanic, body, bladder, blood or rectal temperature.

At step 1004, "wet" cooling is initiated to provide additional cerebral cooling. The "wet" cooling may be continued for between about 10 minutes to 9 hours. At step 1006, an operator inputs the target temperature into the control system. The operator may set a target temperature range for either the core or cerebral temperature, For example, in some embodiments, the target temperature range could be within a range of about 30 to 37° C. for the core temperature, such as a range of between about 30-32° C., alternatively a range of between about 32-34° C., alternatively a range of between about 34-36° C., alternatively a range of between about 31-34° C., alternatively a range of between about 32-36° C., alternatively a range of between about 34-37° C., alternatively a range of between about 32-37° C. At step 1008, the patient's temperature is measured again. In some embodiments, the control unit 19 may be connected to a means for measuring the temperature, such as a thermometer, sensor or temperature sensors known in the art, such that the control unit automatically controls measuring the temperature. Alternatively, the control unit 19 may give an warning or indication that the temperature needs to be measured. At step 1010, the operator compares the measured temperature to the target temperature range. At step 1012, if the temperature is above the desired range, no action is taken and the "wet" cooling is continued until the temperature is again measured and is found to be within the target temperature range. Once the temperature is within the target range, at step 1014, the switch 17 is activated to disconnect communication with the liquid source and at step 1010, cooling reverts back to "dry" cooling using only the substantially dry gas. At step 1018, at an interval set by the operator, the patient's temperature is measured. At step 1020 the measured temperature is analyzed against the target range set by the operator in step 1000. If the temperature is still within the target range, at step 1026, the "dry" cooling is continued until the next interval for measuring the patients temperature. If the patient's temperature has risen above the target temperature, at step 1022, switch 17 is activated to reconnect the liquid source to the catheter 10 and at step 1024, "wet" cooling is reinitiated to reduce the patient's temperature back into the target temperance range. The "wet" cooling is continued until the next interval for measuring the patient's temperature at step 1008. If the patient's temperature is back within the target range at step 1010, the "wet" cooling will be discontinued at step 1014 and "dry" cooling only will be continued at step 1016. If the patient's temperature has not been lowered back into the target range at step 1010, the "wet" cooling will be continued until the next interval for measuring the patient's temperature. The patient's temperature can be maintained within the target range in this manner for a period of to about 10 days, or longer if necessary.

In alternative embodiments, other ranges or limits for the patient's temperature could be used with a different set of instructions for controlling the amount of and type of cooling delivered. For example, instead of setting a target range for the cerebral or core temperature, the control system could be programmed such that the operator sets a target temperature for the cerebral temperature between 18-36° C., alternatively 19-36° C., alternatively 20-36° C., alternatively 23-36° C., alternatively 25-36° C., alternatively 27-36° C., alternatively 30-36° C., alternatively 34-36° C., alternatively 32-36° C., alternatively 32-34° C., depending upon the patient's condition and includes instructions to maintain the patient's cerebral temperature within ±0.5° C. of the target temperature, alternatively ±0.1° C. of the target temperature, ±1° C. of the target temperature, ±1.5° C. of the target temperature, ±2° C. of the target temperature, ±3° C. of the target temperature. In another alternative embodiment, the target temperature could be a minimum temperature for the core temperature and the control system could include instructions to maintain wet cooling until the core temperature reaches the minimum allowed temperature at which time either dry cooling only or no cooling would be initiated.

Figure 7A:
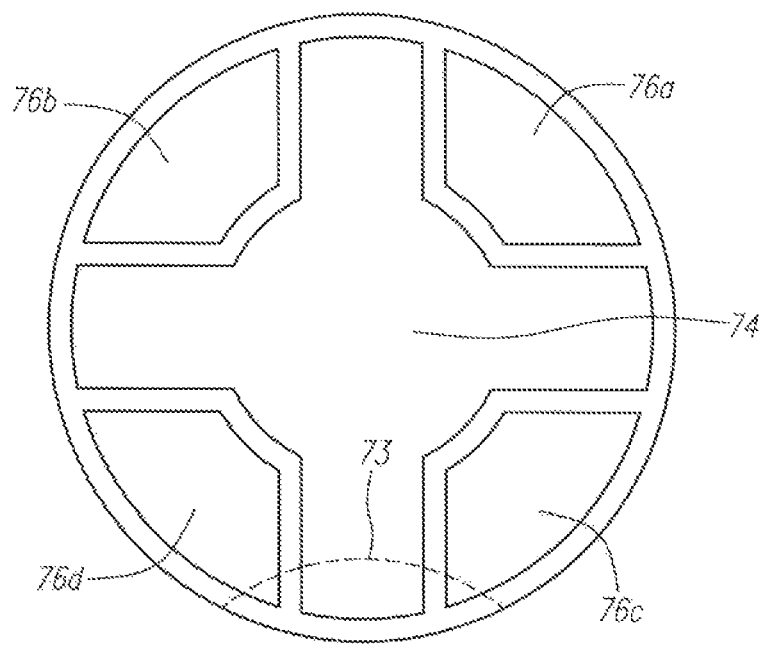
FIG. 7A illustrates a cross-section of an alternative embodiment of nasal catheter having a plurality of lumens for separately transporting a liquid and a compressed gas according to the present invention.
Figure 7B:
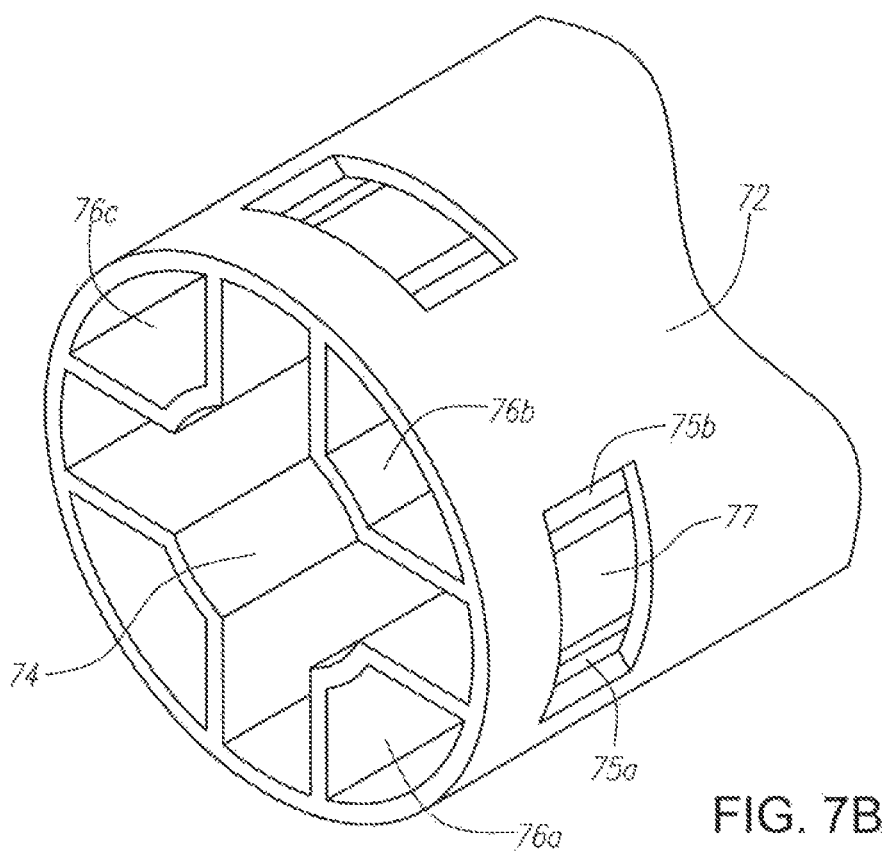
FIG. 7B illustrates a cross-section of an alternative embodiment of a nasal catheter having a plurality of ports for nebulizing a liquid and delivering a nebulized liquid spray to the nasal cavity according to the present invention.
Figure 7C:
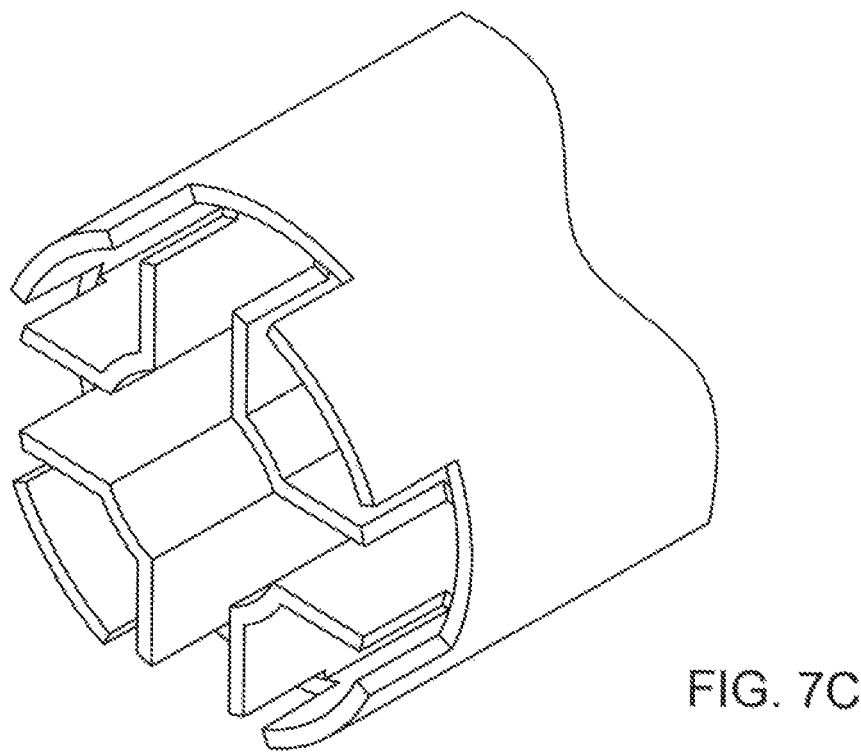
FIG. 7C illustrates a cross-section of an alternative embodiment of a nasal catheter having a plurality of ports for nebulizing a liquid and delivering a nebulized liquid spray to the nasal cavity according to the present invention.
Figure 7D:
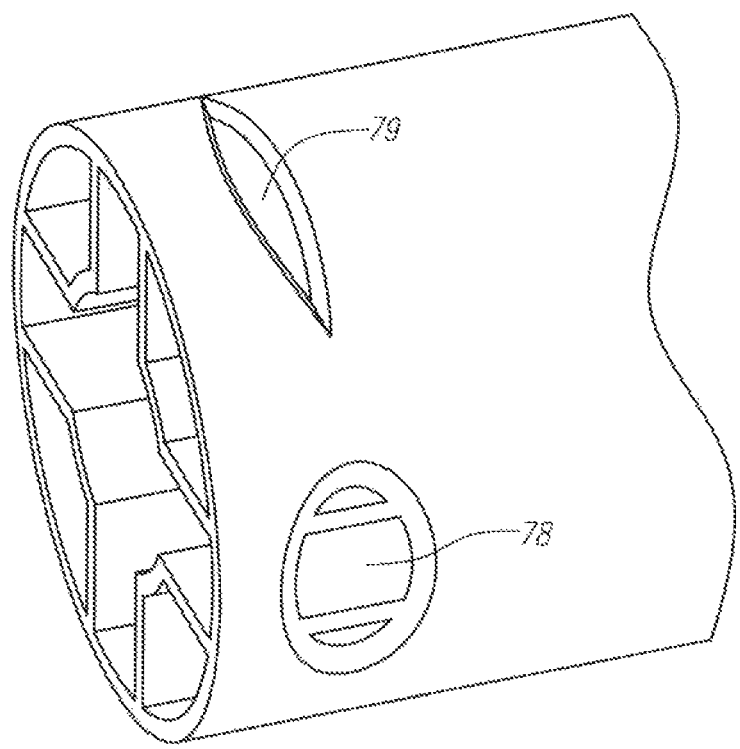
FIG. 7D illustrates a cross-section of an alternative embodiment of a nasal catheter having a plurality of ports for nebulizing a liquid and delivering a nebulized liquid spray to the nasal cavity according to the present invention.
Figure 8:
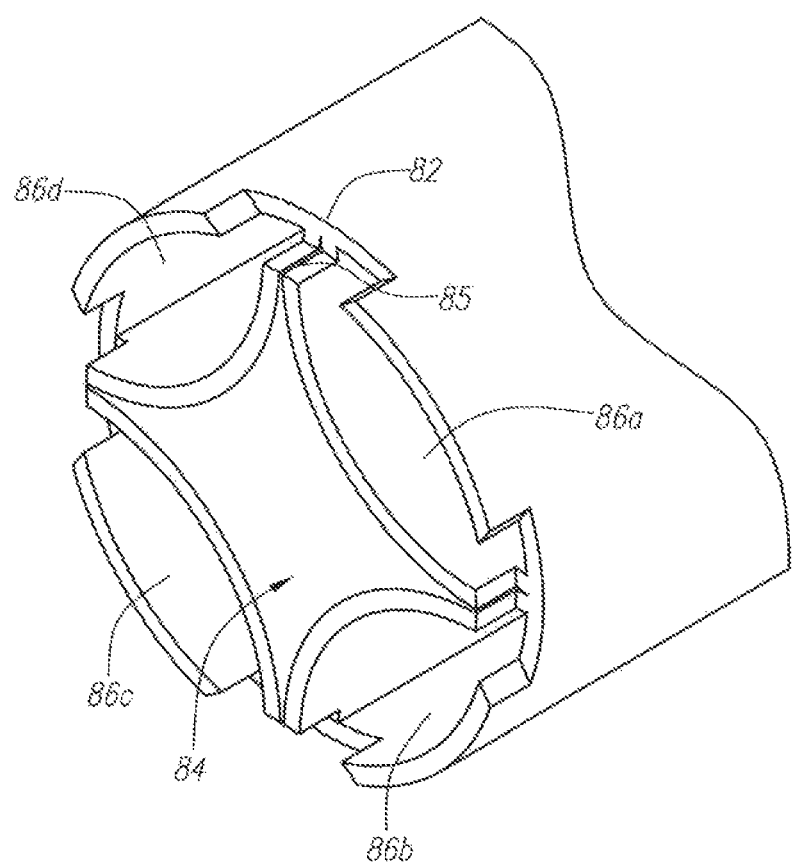
FIG. 8 illustrates a cross-section of an alternative embodiment of nasal catheter having a plurality of lumens for separately transporting a liquid and a compressed gas according to the present invention.
Figure 10:
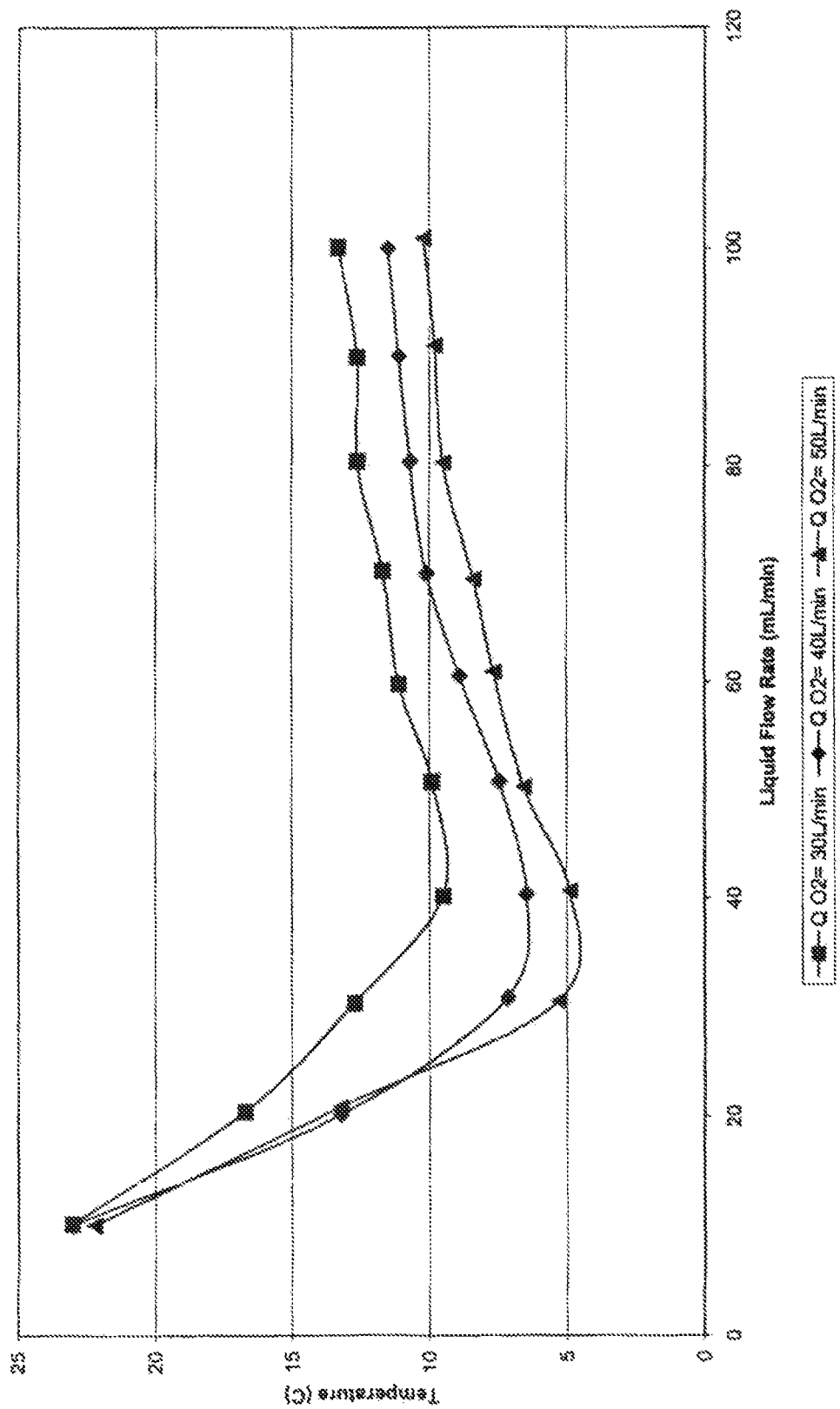
FIG. 10 is a graph of the nasal temperatures against liquid flow rate for the different compressed gas flow rates listed in FIG. 9.
Figure 11:
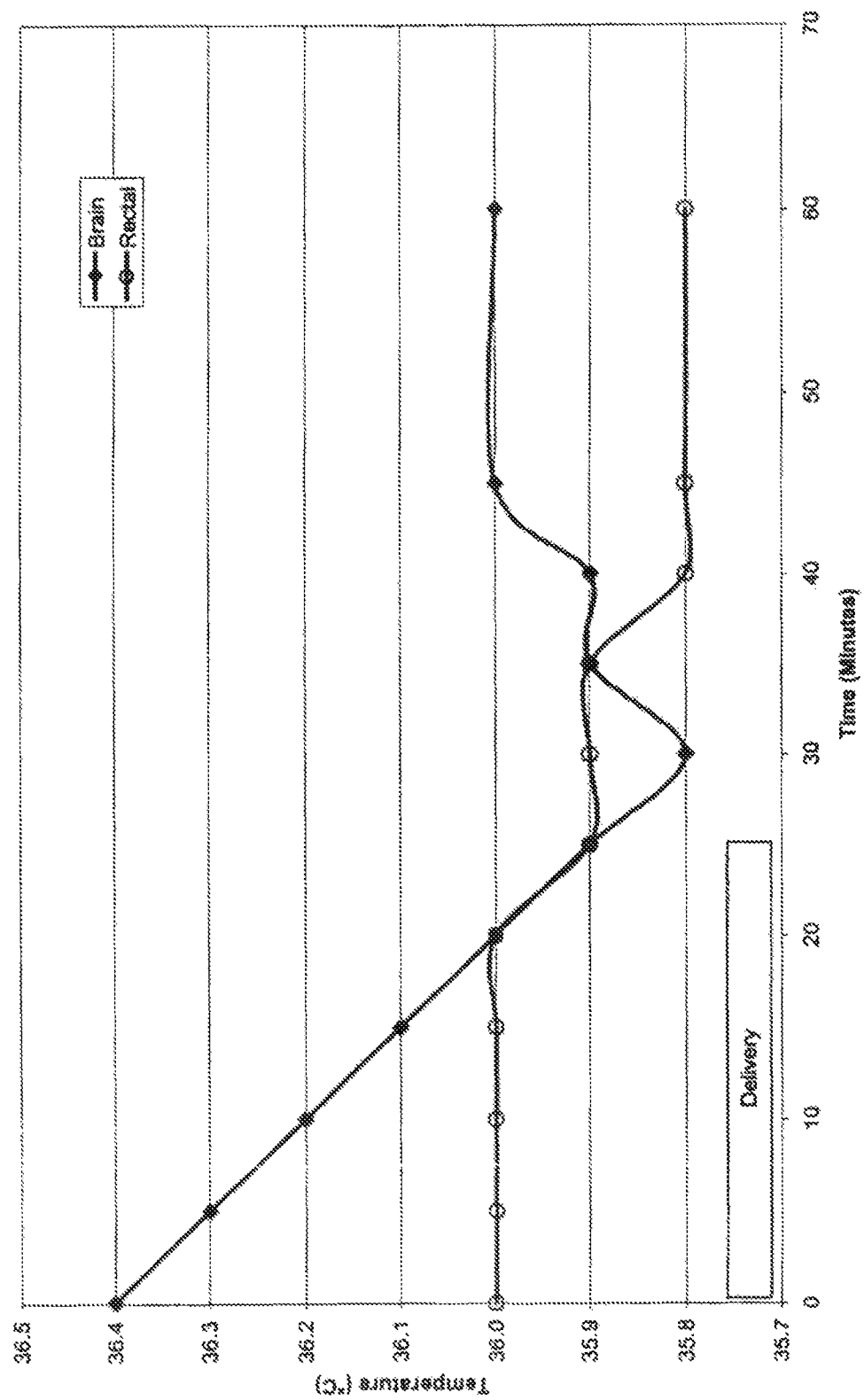
FIG. 11 is graph illustrating the gradient between cerebral and systemic cooling achieved using a method according to the present invention in a human.
Figure 12:
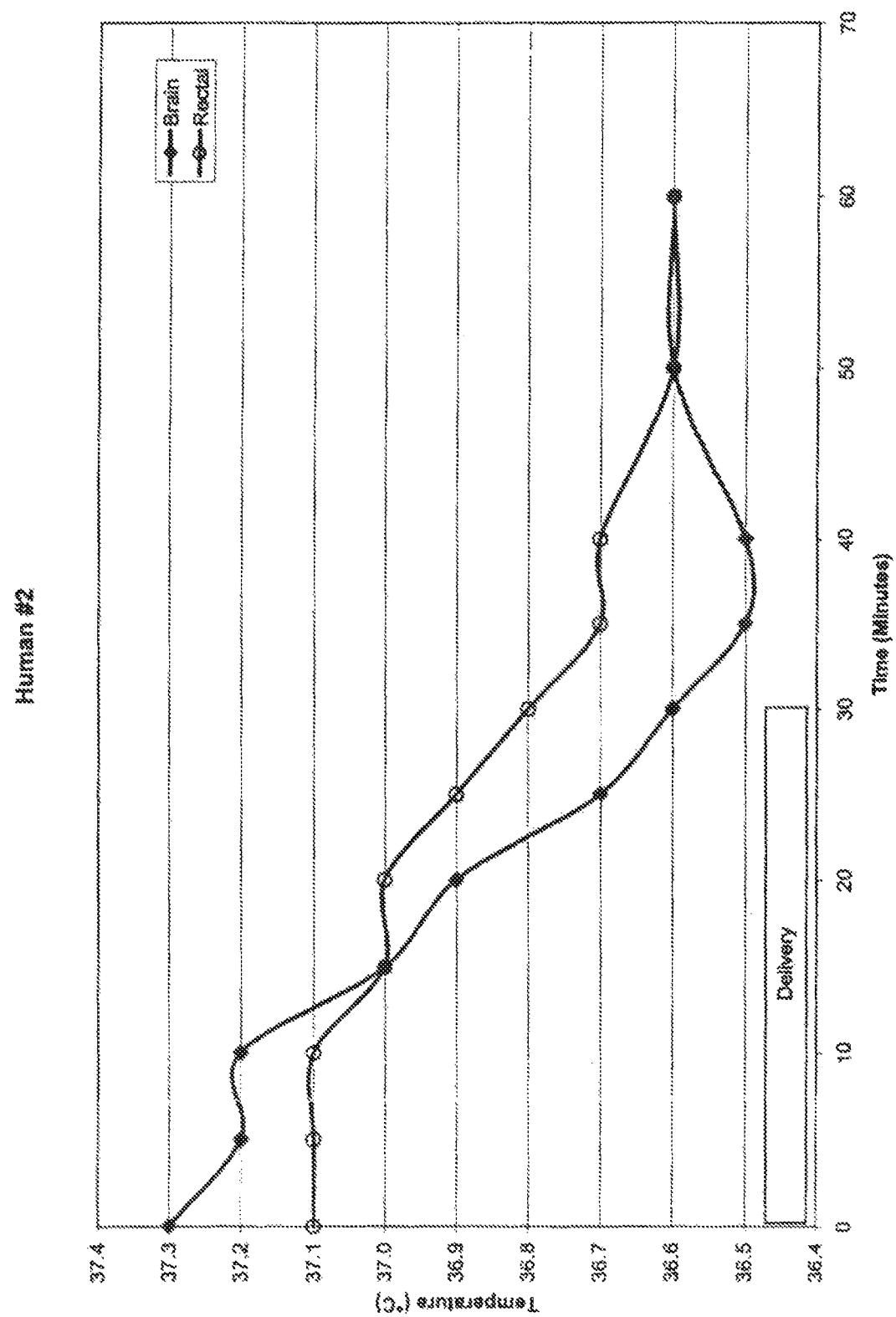
FIG. 12 is a graph illustrating the gradient between cerebral and systemic cooling achieved using a method according to the present invention in a human.
Figure 13:
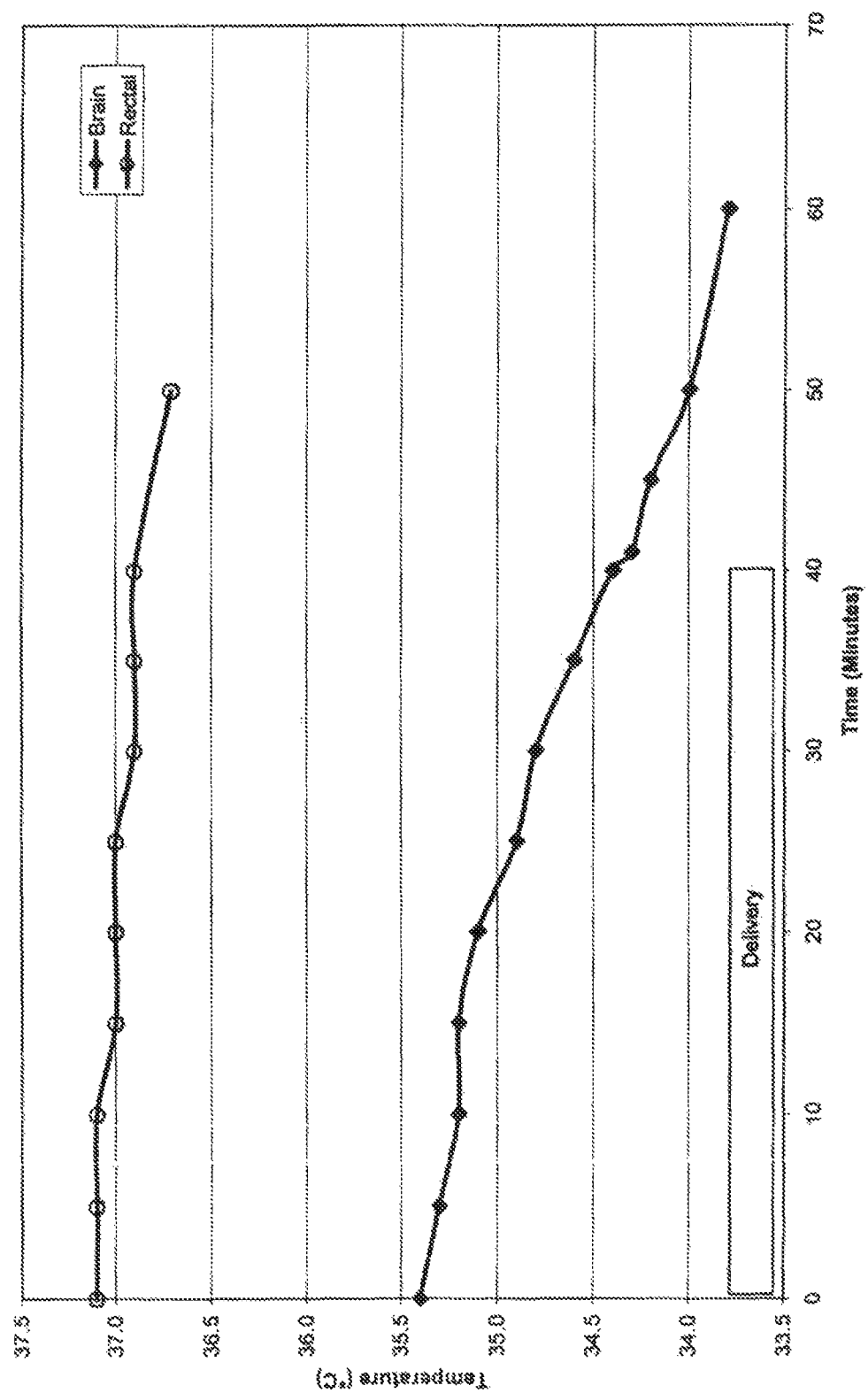
FIG. 13 is a graph illustrating the gradient between cerebral and systemic cooling achieved using a method according to the present invention in a human.
Figure 14:
FIG. 14 is a graph illustrating the gradient between cerebral and systemic cooling achieved using a method according to the present invention in a human.
Figure 15:
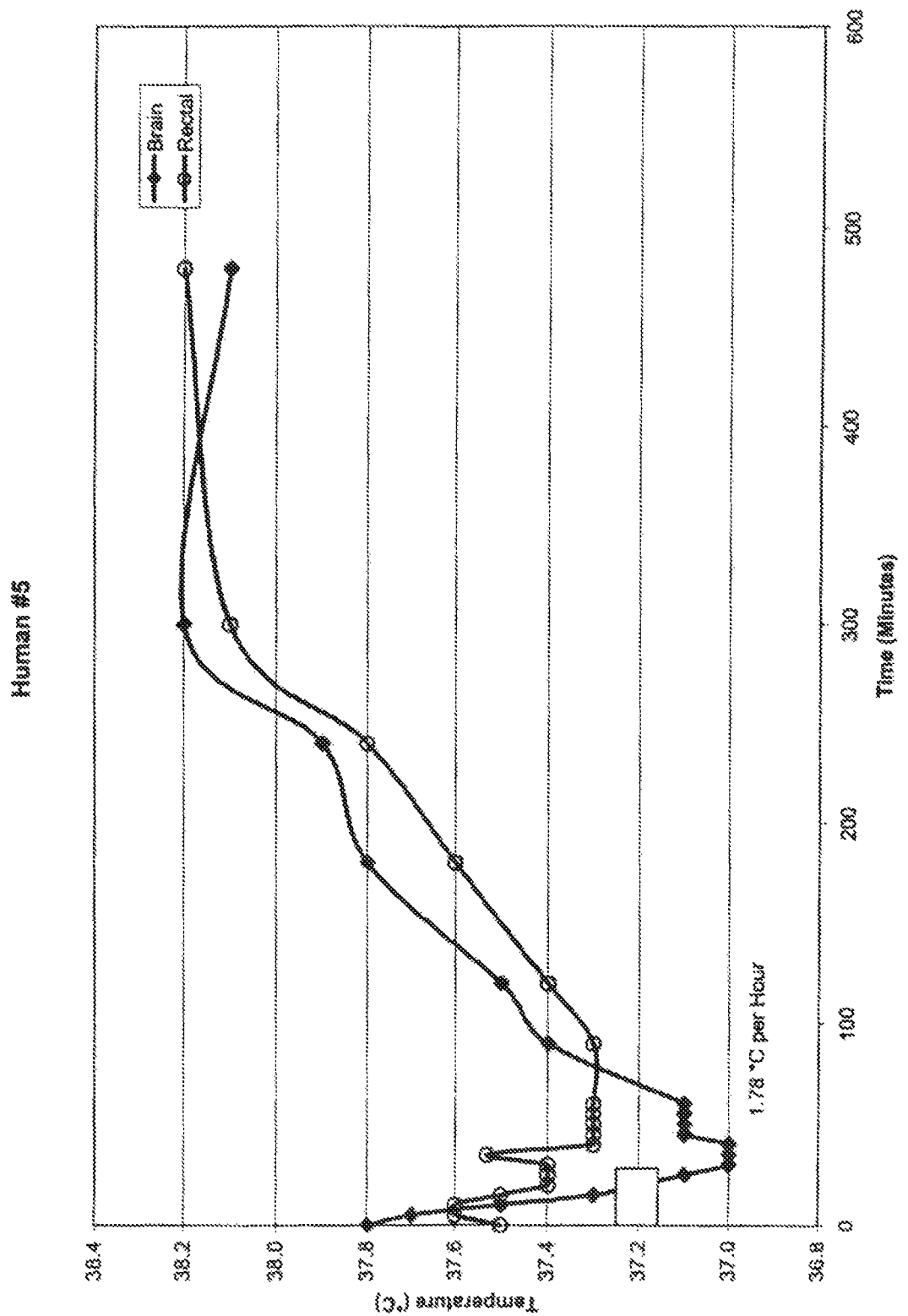
FIG. 15 is a graph illustrating the gradient between cerebral and systemic cooling achieved using a method according to the present invention in a human.
Figure 16:
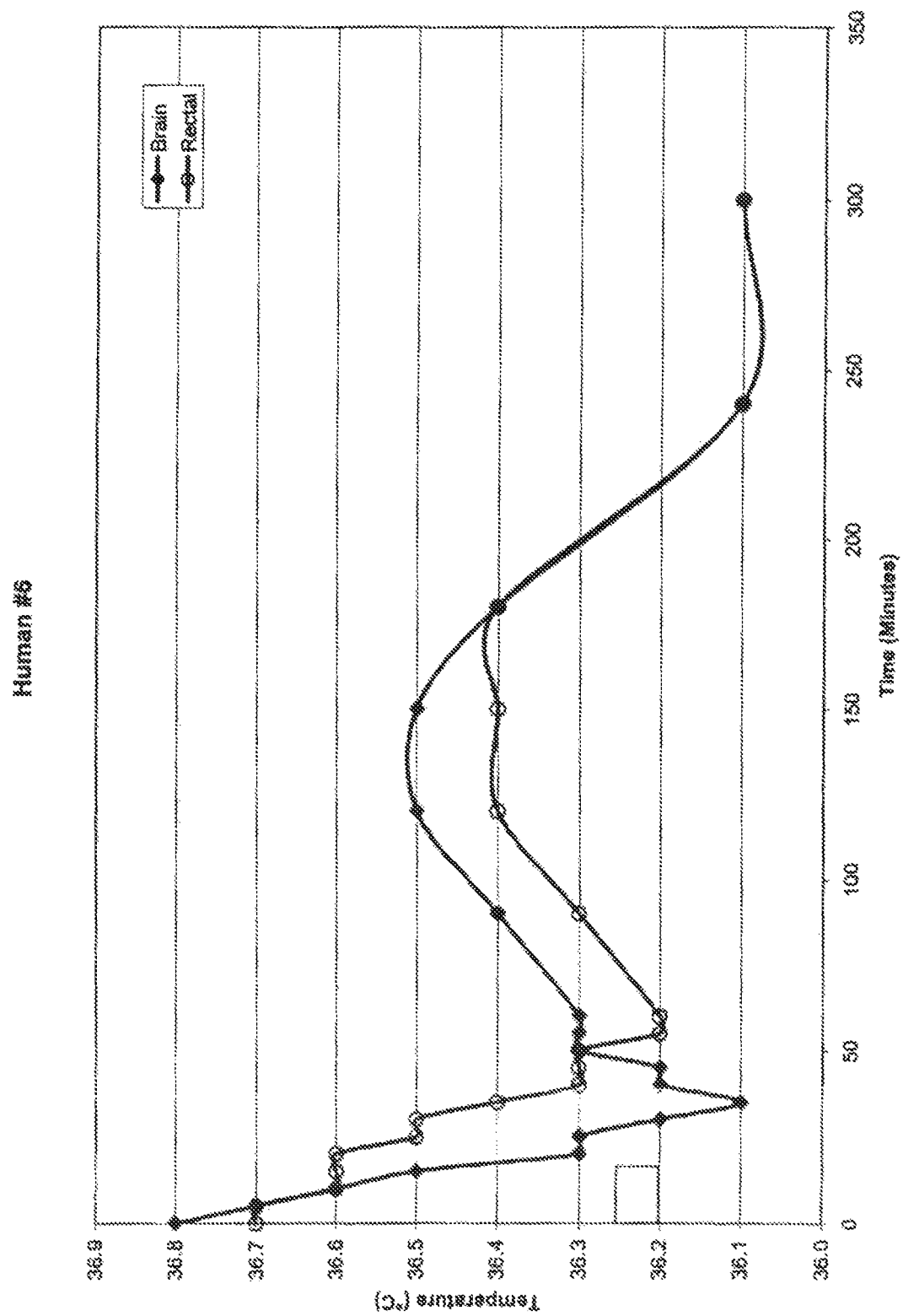
FIG. 16 is a graph illustrating the gradient between cerebral and systemic cooling achieved using a method according to the present invention in a human.
Figure 17:
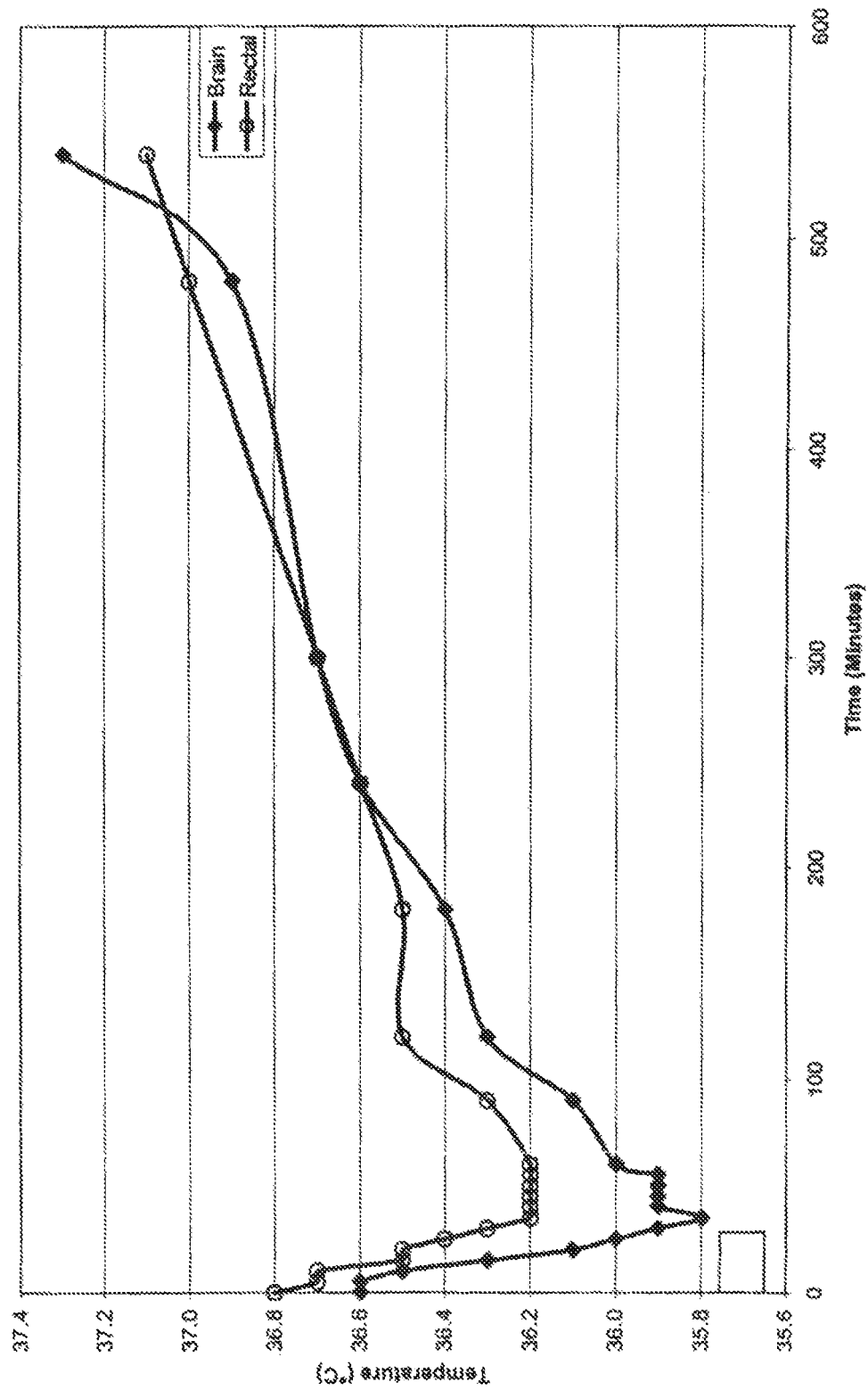
FIG. 17 is a graph illustrating the gradient between cerebral and systemic cooling achieved using a method according to the present invention in a human.

FIGS. 6A-B and 7A-D depict alternative configurations for the liquid and gas channels within the nasal catheter and delivery ports on the outer walls of the catheter that may provide for easier mixing of the liquid and compressed gas at the delivery port. In FIGS. 6A-B, the nasal catheter is formed of a length of extruded tubing with interior side walls 63*a-d* creating a central square lumen 64 in which the compressed gas may be transported and four separate outer channels 66*a-d* in which the liquid may be transported. Here, when mixing channel 68 is drilled through the outer wall of the catheter at one of the corners where two of side walls 63*a-b* of the central lumen 64 connect with the outer wall of the catheter, openings 60*a* and 60*b* are created in each of the adjacent interior channels 66*a-b* through which liquid can enter the gas stream flowing through mixing channel 68. This design simplifies the construction of the device by eliminating the need for a separate connecting tube to connect the liquid lumens with the mixing channel. Moreover, the size of mixing channels 60*a-b* may be altered to provide for a desired liquid flow rate by adjusting the diameter of mixing channel 68. FIGS. 7A-D depict an alternative embodiment of a nasal catheter with a shaped central lumen 74 for transporting the compressed gas surrounded by four outer channels 76*a-d* for transporting the liquid. Delivery ports 72 are created by making skyved cuts 73 in the outer wall of the catheter, which creates aperture 77 from the gas lumen 74 and openings 75*a-b* into the outer channels 76*a-d* transporting the liquid from which the liquid can enter into the gas stream. As depicted in FIG. 7B-D, the skyved cuts may be rectangular 73, circular 78, or V-shaped 79, and may be of varying sizes to affect both the velocity of the nebulized liquid, flow rate, and size of the spray particles.

In another alternative embodiment, depicted in FIG. 8, central lumen 84 may be used to transport the liquid, while four outer channels 86*a-d* are used to transport the compressed gas. Delivery port 82 is created by making a skyved cut in the outer wall of the catheter at the junction of the central lumen 84 and two adjacent liquid channels 84*a-d*. The skyved cut provides an aperture through which the compressed gas from outer gas channels 86*a-d* can escape and also creates central slit 85 in fluid communication with central lumen 84 for introducing the liquid from central lumen 84 into the gas stream. In addition to reducing the manufacturing complexity by eliminating the need for a separate channel between the liquid and gas lumens, this may be advantageous for providing a wider dispersion of flow from each delivery port 82.

The liquids used with this catheter include liquids having a boiling point of about 38-300° C., more preferably a boiling point of about 38-200° C., more preferably a boiling point of about 60-150° C., more preferably a boiling point of about 70-125° C., more preferably a boiling point of about 75-110° C., more preferably a boiling pint of about 60-70° C. Compounds having suitable characteristics for use herein include hydrocarbons, fluorocarbons, perfluorocarbons, and perfluorohydrocarbons. Saline is another example of a substance having suitable characteristics for use herein. As used in this specification, the terms "fluorocarbon," "perfluorocarbon," and "perfluorohydrocarbon" are synonymous. In addition to containing carbon and fluorine, these compounds may also contain other atoms. In one embodiment, the compounds could contain a heteroatom, such as nitrogen, oxygen, sulfur, or a halogen, such as bromine or chlorine. These compounds may be linear, branched, or cyclic, saturated or unsaturated, or any combinations thereof. Exemplary perfluorocarbons include perfluoropropane, perfluorobutane, perfluoropentane, 2-methyl-perfluoropentane, perfluorohexane, perfluoroheptane, and perfluorooctane.

The liquids delivered through the catheter (single or multi-lumen) may also comprise a humidifier. Alternatively, the humidifier may be delivered separately through the catheter or using an alternative delivery device. When used in conjunction with the cooling liquid, the humidifier would have to be cooled or else it would counteract the cooling effect of the other liquid. Where the humidifier was used independently for humidification, it could also be warmed. The humidifiers may be delivered through the same ports in the catheter as the cooling liquid. Alternatively, a different lumen and/or port in the catheter may be used to deliver the humidifier. The purpose of the humidification is to prevent the sensation of dryness, the crusting and trauma that could result from the dryness, the nasal congestion and mucous production that could result from dryness imparted by the high gas flow rates or from the evaporation of the liquid (e.g., PFC). The congestion and mucous production reduce the effectiveness of the cooling by limiting the cavity in which the evaporation occurs and by directly blocking holes in the catheter. This phenomenon may account for rapid initial cooling rates observed, followed by slower cooling rates beyond the first 20 to 30 minutes.

The humidifier may be, but is not limited to isotonic saline, or water. Where water is used as the humidifier, the quantity needed to be added for full saturation is about 41 micrograms/L or gas. Alternative nasal inhalers, such as but not limited to, ephedrine, pseudoephedrine (e.g., Afrin), antihistamines, ipratropium (e.g., Altrovent), and anticholinergics, may also be used to saturate the air in the nasal cavity.

The gases used with the catheter include any gas capable of evaporating the liquid. The gas can include, but is not limited to, nitrogen, air, oxygen, argon, or mixtures thereof.

In use, as seen in FIG. 1, this catheter is intended to be placed through the patient's nostrils and extend through the narices of the nose to the nasopharyngeal region of the nasal cavity. The length of catheter 10, which extends to the nasal pharyngeal region of the nasal cavity and multiple ports 12a-m located longitudinally and axially along the outer wall of the catheter enable catheter 10 to disperse the liquid spray perpendicular to the longitudinal axis of catheter 10 and over the entire nasal cavity region. This is in contrast to simply directing the spray through a single spray nozzle at a catheter tip, which would have the spray limited to a particular area along the longitudinal axis of catheter. This distinction is critical in that dispersing the spray over a larger region permits greater cooling though evaporative heat loss.

In addition, the ability to nebulize the liquid at each delivery port ensures that the distribution of varying sizes of liquid particles will be uniform throughout the nasal cavity. Specifically, when a liquid is nebulized, a spray with liquid particles of various sizes is created. If the liquid was nebulized at the proximal end of the nasal catheter or outside of the catheter and then transported as a nebulized liquid spray through the catheter lumen to the multiple delivery ports, the smaller liquid particles would flow through the proximal delivery ports while the larger liquid particles would be carried to the distal end of the tube be hue being delivered to the nasal cavity via one of site delivery ports near the distal end of the nasal catheter. This would result in an uneven distribution of the liquid particles within the nasal cavity. Conversely, when the liquid is transported through site nasal catheter and nebulized separately at each delivery port just prior us delivery, the site distribution of liquid particles distributed at any given point in the nasal cavity is uniform. This is critical because an even distribution of the varying sized liquid particles provides for better evaporation of the liquid spray, which results in better cooling through evaporative heat loss and is more tolerable to the patient. Furthermore, since the liquid begins to evaporate immediately upon contact with the gas, mixing at the point of use in the patient will ensure efficient use of all available cooling.

The liquid flow rate is also a critical factor for cerebral cooling. FIG. 10 depicts the amount of nasal cooling per different liquid flow rates. The gradient between the cerebral and systemic cooling that forms over time is desirable in order to minimize damage to other organs and hypothermia during the cerebral cooling. In order to create a gradient between the cerebral and systemic temperature, the cerebral cooling must be induced rapidly, for example at a rate of at least about 1° C. in hour, alternatively at least about 1.5° C. in hour, alternatively at least about 2° C. in hour, alternatively at least about 3° C. in hour, alternatively at least about 4° C. in hour, alternatively at least about 5° C. in hour between the cerebral temperature and the systemic temperature. This sudden initial exposure to cold induces a vasoconstriction response in the carotid arteries causing the carotid arteries to constrict, which helps isolate the cerebral vasculature and prevent warmer blood from the heart traveling to the brain and the cooler blood in the brain from traveling to and thereby cooling the rest of the body. This initial vasoconstriction response thus further aids the cooling process by preventing warmer blood front traveling to the head. In addition, the initial cooling lowers the metabolic demand of the head, thus the carotid artery can further constrict and further isolate the head. After the initial induction, in order to maintain sufficient cooling, the spray may be delivered at a lower flow rate. The lower flow rate may result in a gradient between the cerebral and systemic temperature of at least about 0.1° C., alternatively at least about 0.2° C., alternatively at least about 0.3° C., alternatively at least about 0.4° C., alternatively at least about 0.5° C., alternatively at least 0.6° C., alternatively at least about 1.0° C., alternatively at least about 1.5° C., alternatively at least about 2.0° C., alternatively at least about 2.5° C., alternatively at least about 3.0° C., alternatively at least about 3.5° C., alternatively at least about 4.0° C., alternatively at least about 4.5° C., alternatively at least about 5.0° C.

In addition to the liquid flow rate, it has also been shown that the ratio of gas flow rate to liquid flow rate is a critical factor affecting the cerebral cooling within the nasal cavity. Initially, it was thought that increasing the liquid flow rate would increase cooling. The cooling rate, however, only increases if the gas flow is concurrently increased to evaporate the nebulized liquid. This is necessary because the cooling within the nasal cavity is achieved through evaporative heat loss as nebulized liquid evaporate. If the nasal cavity becomes saturated with the evaporated liquid, however, then the evaporation rate decreases and consequently, the cooling rate decreases. Thus, the rate of evaporation is dependant on the concentration of the liquid within the nasal cavity as well as the flow rate of the liquid. Therefore, increasing the liquid flow rate to the nasal cavity only increases the cooling rate if the gas flow rate is also increased to evaporate off the nebulized liquid. The ratio for the liquid delivery rate:gas delivery rate to optimize the evaporation and maintain a constant rate of evaporation preferably ranges from 1:25 mL-1:5000 mL, more preferably from 1:500 mL-1:2000 mL, more preferably from 1:700 mL-1:1500 mL. FIGS. 9-10 depict the varying cooling in an artificial nasal cavity at three different gas flow rates (40 L/min, 30 L/min, and 50 L/min) as the liquid flow rate is varied. The goal is to have 100% evaporation (i.e., "spray"). It is desirable to have the maximum amount of cooling with the least amount of liquid used. Therefore, the gas flow rate should be at least about 30 L/min, alternatively at least about 40 L/min, alternatively at least about 50 L/min. The liquid flow rate should be at least about 40 L/min, alternatively at least about 50 mL/min, alternatively at least about 60 mL/min, alternatively at least about 70 mL/min, alternatively at least about 80 mL/min, alternatively at least about 90 mL/min, alternatively at least about 100 mL/min.

The flow rate of the gas and liquid can be altered during the process according to the amount of cooling achieved. Feedback can be provided in the form of nose temperature, body temperature, brain temperature, rectal temperature, etc. For example, an alarm could be triggered when the body temperature falls below 35° C. and delivery of the fluids and gas could be stopped. Additionally, or in the alternative, feedback in the form of the brain temperature could be provided such that the rate of delivery of the fluids and gases increases if the cooling rate of the brain is less than about 5° C. in one hour, alternatively less than about 4° C. in one hour, alternatively less than about 3° C. in one hour, alternatively less than about 2° C. in one hour, alternatively less than about 1° C. in one hour.

Cooling Calculations

The following calculations estimate the maximum cooling that can be obtained using a unit does of 2 liters of perfluorohexane. The cooling effect of PFH is related to two aspects of thermodynamics: (1) heat capacity of the liquid, as it is warmed from its temperature at application to that of the body and (2) heat of vaporization as it changes from the liquid to the gas state. The relevant properties of perfluorohexane are as follows:

ρ, Density: 1.68 grams/ml
c, Specific Heat: 1.09 kJ/kg° C.=0.26 cal/g° C.
h, Latent Heat: 85.5 kJ/kg=20.4 cal/g The calculation for heat transfer due to warming the liquid is:

$$Q=c*m*(T2-T1) \text{ or } Q=cm\Delta T \quad \text{Equation 1:}$$

where m=the mass of the liquid administered
T1 is the temperature of the liquid at administration
T2 is the temperature to which the liquid is warmed In the patient case, the heat removed is calculated using the following assumptions: (1) a unit does quantity of 2 liters is used; (2) the PFC is administered at 0° C.; and (3) the PFC is warmed completely to body temperature of 37° C.

$$Q=2000 \text{ ml}*1.68 \text{ g/ml}*0.26 \text{ cal/g}° \text{ C.}*(37° \text{ C.}-0° \text{ C.})=32,300 \text{ calories}$$

The calculation for heat transfer due to evaporation of the liquid is:

$$Q=h*m \quad \text{Equation 2:}$$

Therefore, assuming a dose of 2 liters, $$Q=2000 \text{ ml}*1.68 \text{ g/ml}*20.5 \text{ cal/g}=68,900 \text{ calories}$$

For a 2 liter quantity of liquid, the maximum heat removal=100,000 calories or 100 Kcal. The amount of cooling to the body can be calculated using the following assumptions: (1) patient weight of 70 Kg, (2) specific heat of patient=0.83 cal/g° C., (3) heat generated by metabolism or other sources is negligible, and (4) other heat added or removed from the patient is negligible. After rearranging Equation 1 ($\Delta T=Q/(c*m)$), the net change in temperature of the whole body of the patient can be calculated as follows:

$$\Delta T=100 \text{ kcal}/(0.83 \text{ cal/g}° \text{ C.}*70 \text{ kg})=1.72° \text{ C.}$$

Therefore, the maximum whole body cooling that could occur from a 2 liter dose is approximately 1.7° C. This should result in a body temperature no lower than 35° C., which should not cause any cold related complications.

The sensitivity, i.e., the resultant temperature change experienced by the patient, will depend on the size of the patient. For a very small patient of 40 Kg (88 pounds), the resultant temperature change is $\Delta T=100$ kcal/(0.83 cal/g° C.*40 kg)=2.1° C. For a very large patient of 100 Kg, the resultant temperature change is $\Delta T=100$ kcal/(0.83 cal/g° C.*100 kg)=0.83° C.

By applying the cooling spray to the nasal cavity, there will be more cooling in the head than the remainder of the body. Calculations can be done to determine how cold the head might become if all the cooling is focused solely in the head. The amount of cooling to the head can be calculated using the following assumptions: (1) mass of head=5 kg, (2) specific heat of head=0.83 (same as rest of body), and (3) heat transfer from body (warming from cerebral blood flow) is negligible.

$$\Delta T=q/(s*m)=100 \text{ kcal}/(0.83 \text{ cal/g}° \text{ C.}*5 \text{ kg})=24 \text{ Degrees C.}$$

This corresponds to a potential minimum head temperature of 13° C.

The above calculations assume that every bit of the liquid is warmed fully to body temperature and evaporates completely. It is likely that in a clinical setting, there will be incomplete warming and evaporation. Specifically, some of the gas and vapor leaving the body will not be at 37° C., and some of the liquid will trickle out of the patient without contributing to heat transfer. These effects will tend to reduce the cooling from the calculated values.

The head cooling calculation assumes that absolutely no heat will be added to the head from the body. This is, however, a poor assumption. The cerebral blood flow is on the order of 1 L per minute, and assuming that this blood is cooled by only 2 degrees while in the head, the calculation becomes as follows:

$$\text{Net heat removal}=100 \text{ Kcal}-1000 \text{ ml/min}*30 \text{ min}*0.83 \text{ cal/g}° \text{ C.}*2° \text{ C.}=50 \text{ Kcal}$$

Therefore, the cooling in the head is reduced by at least half of the previously calculated value to 12° C., for a minimum possible 25° C. head temperature.

Experimental Data

In use, the nasal catheter of the present invention was inserted through the nose into the nasal cavity. Temperature was measure at baseline (3 times over 10 minutes) and at every minute or continuously at the ventricle or epidural space, where available, and bladder or rectum during the procedure. A suction catheter was positioned in the patient's mouth to prevent pharyngeal liquid from entering the esophagus and a nasogastric (NG) tube was placed in the patient's stomach to suction any liquid PFC or PFC vapor. NG suction was continuous. Nasal cooling was administered via a nasal catheter with one oxygen/PFC mixer and fan spray nozzle per naris. Nasal prongs were positioned in the narices and secured to the nose by tape. After measurement of the baseline temperatures, cooling was initiated. Temperature was monitored until it returned to the baseline value. A portion of the PFC was recovered from the oral suction catheter placed in the back of the patient's throat. This recovered PFC can be reused and recycled. The following parameters were used for the human studies.

Oxygen was delivered at about 20 L/min throughout the delivery period, alternatively at about 30 L/min throughout the delivery period, alternatively at about 40 L/min throughout the delivery period, depending on the patient.

The PFC (e.g., perfluorohexane) was delivered at a rate of about 15 mL/min, alternatively at about 25 mL/min, alternatively at about 35 mL/min, alternatively at about 45 mL/min, alternatively at about 50 mL/min, alternatively at about 55 mL/min, alternatively at about 65 mL/min, alternatively at about 75 mL/min, alternatively at about 80 mL/min, alternatively at about 85 mL/min, alternatively at about 95 mL/min, alternatively at about 100 mL/min, depending on the patient. The liquid flow rate was sometimes started at a lower flow rate (e.g., about 15 mL/min or about 25 mL/min) and increased to a faster flow rate (e.g., about 45 mL/min, about 50 mL/min, or about 100 mL/min). Alternatively, the liquid flow rate was started at a faster flow rate (e.g., about 50 mL/min) and gradually reduced to a slower flow rate (e.g., about 25 mL/min). A total of amount of about 1.0 L of PFC was delivered, alternatively about 1.5 L, alternatively about 2.0 L, depending on the patient.

The delivery period was approximately 20 minutes, alternatively approximately 25 minutes, alternatively approximately 30 minutes, alternatively approximately 35 minutes, alternatively approximately 40 minutes, alternatively approximately 45 minutes.

In one method, oxygen is delivered at about 40 L/min and PFC is delivered at about 80 mL/min throughout the delivery period. A total of about 2 L of PFC is delivered. The delivery period is approximately 20 to 25 minutes.

Figure 18:
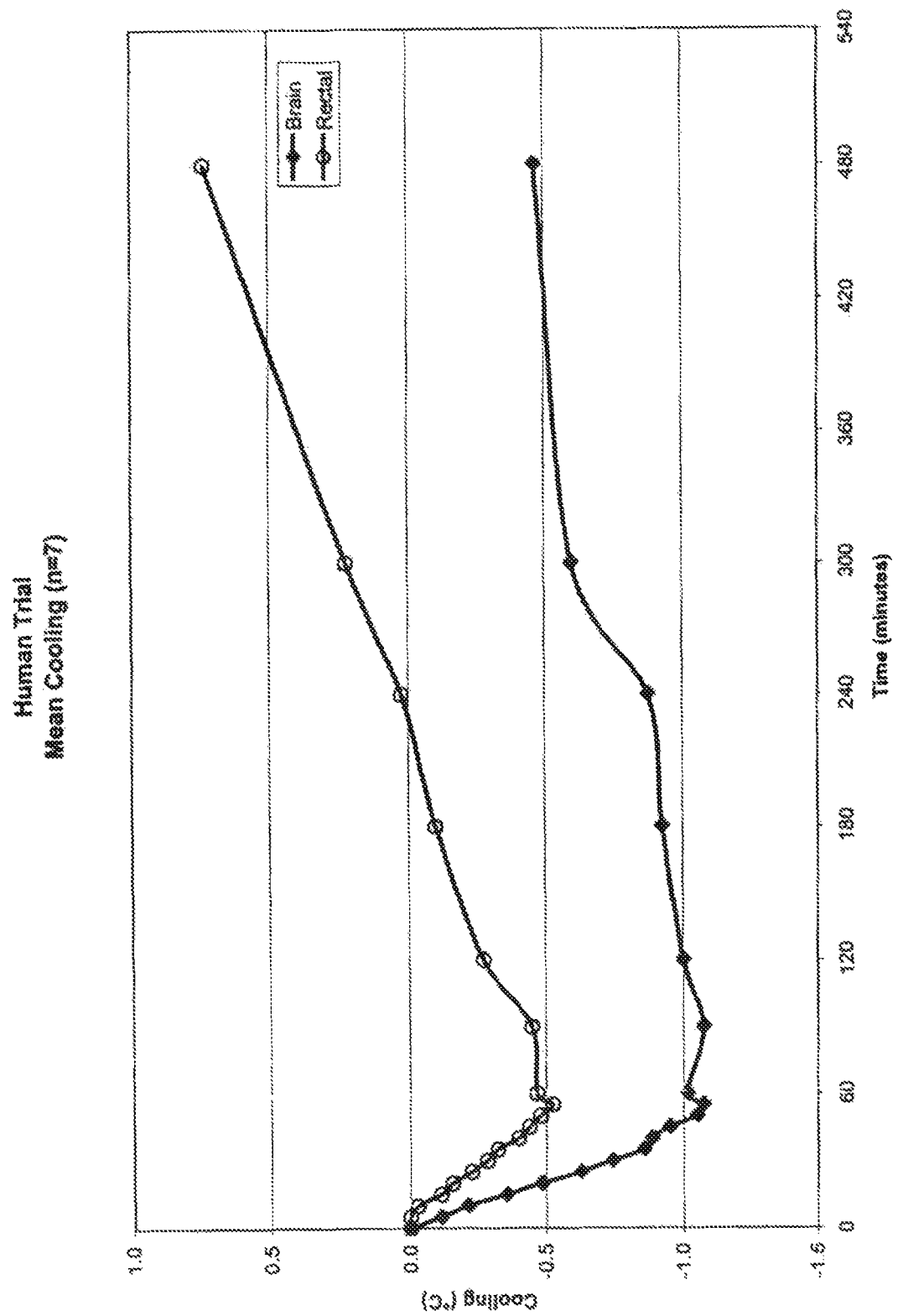
FIG. 18 is a graph illustrating the gradient between mean cerebral and mean systemic cooling achieved using a method according to the present invention.
Figure 19:
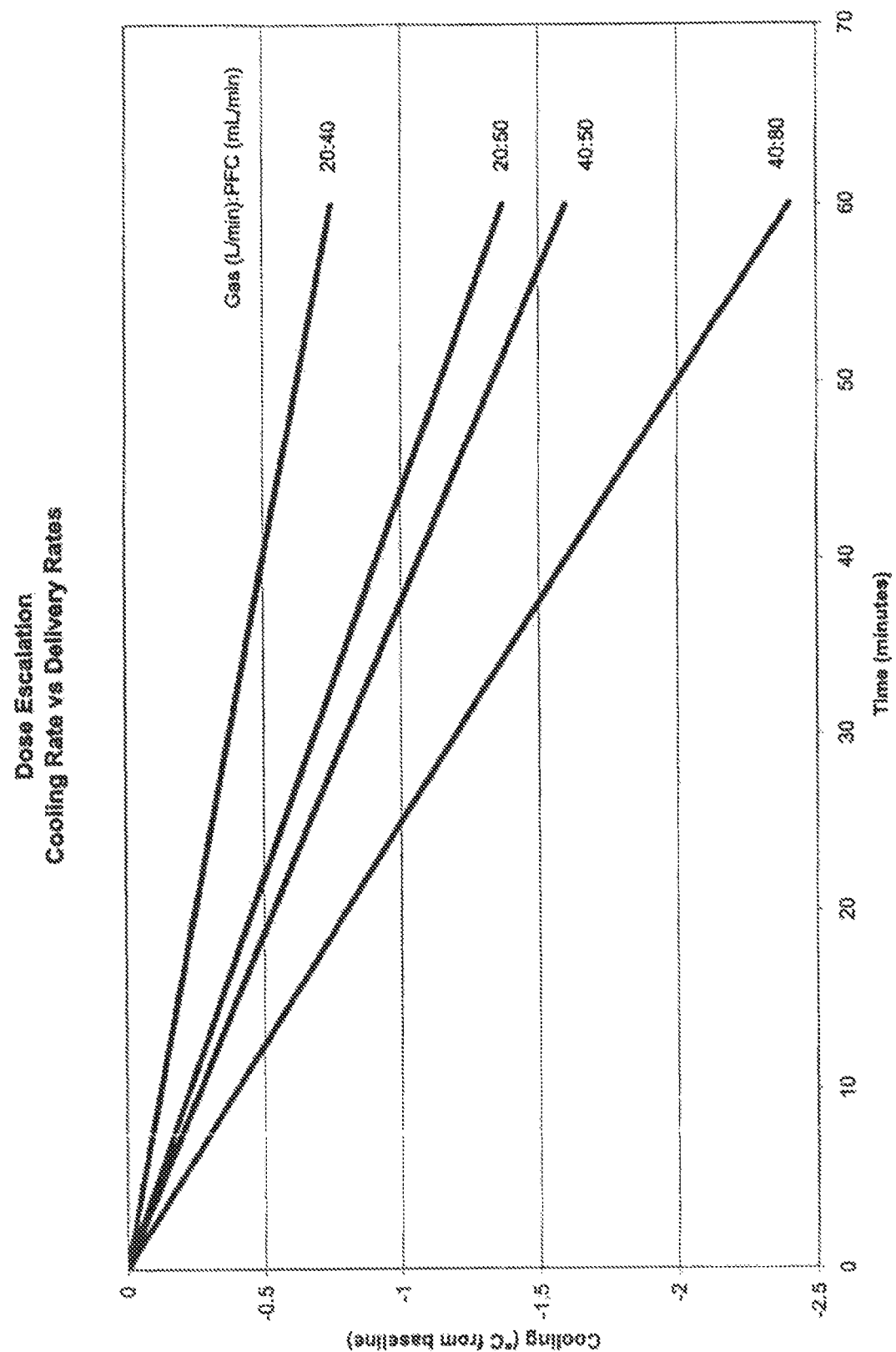
FIG. 19 is a graph illustrating the cooling rates achieved using a method according to the present invention for various delivery rates.

FIGS. 11-17 illustrate the gradient between the cerebral and systemic temperatures achieved using the methods described above. The rectangles at the bottom of the graphs indicate the delivery periods for that particular therapy. FIG. 18 illustrates the mean cerebral and systemic cooling achieved from the experiments illustrated in FIGS. 11-17. FIG. 19 illustrates the cooling temperatures achieved using various delivery rates. As apparent from the figures, selective cooling of the brain is achieved and maintained over time, even after delivery of the cooling agents has stopped. Typically, a gradient between cerebral and systemic temperature of at least about 0.5° C. can be achieved, alternatively about 1.0° C. can be achieved, alternatively about 1.5° C. can be achieved, alternatively about 2.0° C. can be achieved, alternatively about 2.5° C. can be achieved.

Figure 20:
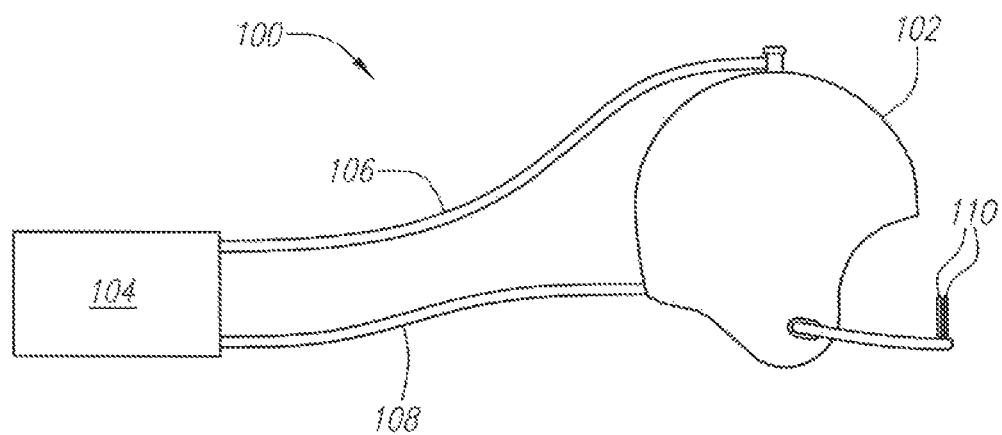
FIG. 20 illustrates an embodiment of a device having a cooling helmet or cap with attached nasal prongs according to the present invention for non-invasive cerebral and systemic cooling.

The catheter of the present invention can also be used in combination with other cooling or heating devices. For example, the catheter may be used in combination with a helmet or cooling cap for synergistic cooling as seen in, for example, U.S. Pat. No. 6,962,600, which is hereby expressly incorporated by reference in its entirety. As seen in FIG. 20, a cooling system 100 comprising a cooling helmet or cap 102 with the nasal catheters or prongs 110 of the present invention attached directly to the cooling helmet or cap. Alternatively, the nasal catheters or prongs may not be attached to the cooling cap or helmet, and still be used in conjunction with the cooling cap or helmet for synergistic cooling (not shown). The cooling system 100 includes a recirculating liquid refrigerant container 104 with an input line 106 and an output line 108 running from the container 104 to the cooling helmet or cap 102. Alternatively, the helmet may only have an input line where cooling is accomplished through evaporation of the liquid refrigerant within the walls of the cooling helmet or cap (not shown). Additionally, the nasal catheters may be used in combination with a warming blanket to enhance the gradient between the cerebral temperature and the systemic temperature where systemic cooling is inadequate to bring down the brain temperature. In one embodiment, a heat pump could be used in conjunction with a cooling helmet or cap and a warming blanket. The heat pump could take heat from the liquid being circulated to the cooling helmet or cap and pump the heat into the warming blanket. The heat pump could use a refrigerant or thermoelectric cycle.

Figure 21:
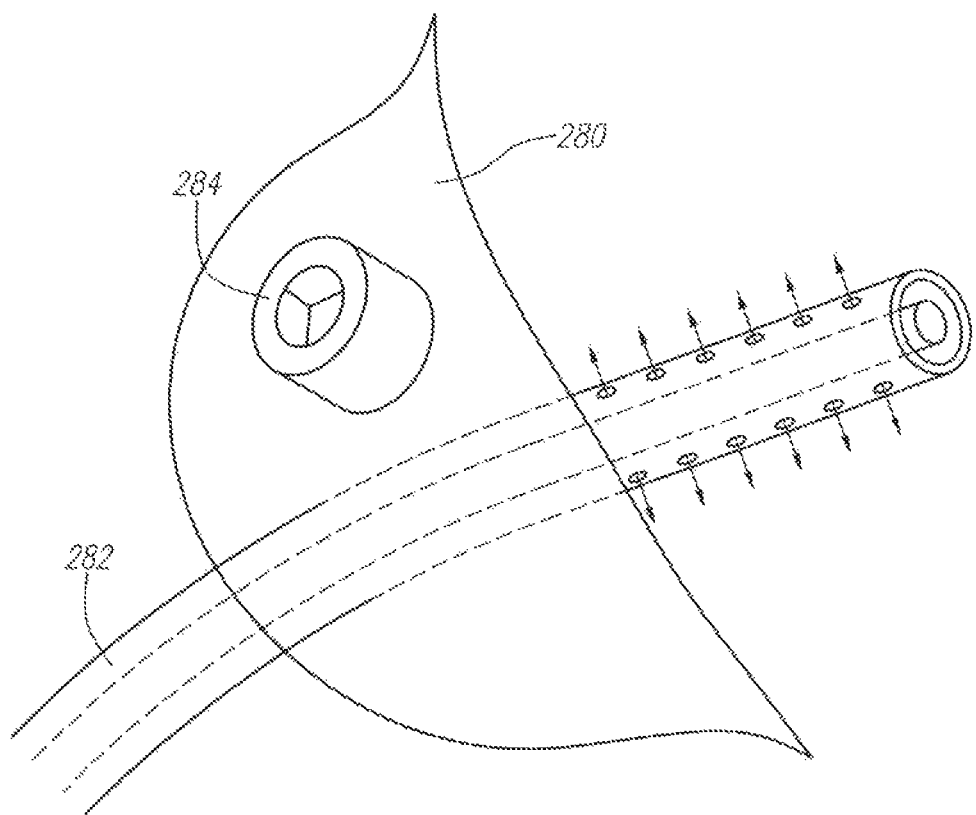
FIG. 21 illustrates as embodiment of a device having a mask with a nasal catheter inserted therethrough.

In another alternative embodiment, a mask can be used in conjunction with the catheter (single or multi-lumen) to increase the amount of air/oxygen/gas delivered to the nasal cavity. This would result in an increase in the rate of liquid evaporation, and therefore the rate of cooling, without increasing the intranasal pressure. As see in FIG. 21, mask 280, such as a continuous positive airway pressure (CPAP) nasal mask, can have catheter 282 fitted therethrough. The positive pressure is given through mask 280. The pressures given through the mask may be about 0 to about 200 cm $H_2O$, alternatively about 0 to about 150 cm $H_2O$, alternatively about 0 to about 100 cm $H_2O$, alternatively about 0 to about 75 cm $H_2O$, alternatively about 0 to about 60 cm $H_2O$, alternatively about 0 to about 50 cm $H_2O$, alternatively about 0 to about 40 cm $H_2O$. Valve 284, preferably a one-way valve, at the said of mask 280 can open at a given pressure, thereby releasing excess gas into the atmosphere. Valve 284 acts as a safeguard against high intranasal pressures that could conceivably lead to gas entrapment in the tissue or entry into the venous vasculature, resulting in a pulmonary embolism. Valve 284 may open when the pressure inside the mask reaches about 55 cm $H_2O$, alternatively about 60 cm $H_2O$, alternatively about 65 cm $H_2O$. In use, mask 280 is placed over the nose and nasal catheter 282 is inserted into the nasal cavity, as described previously. Air and gas are expired through the mouth, as in standard CPAP treatment.

The catheters of the present invention can also be used as drug delivery catheters for delivery of nebulized drugs to the nasal cavity. It is further contemplated that these drugs may be delivered unaccompanied or may be delivered in addition to a cooling agent to facilitate cerebral cooling. As discussed previously, the ability to nebulize the liquid at each delivery port ensures that the distribution of varying sizes of liquid particles will be uniform throughout the nasal cavity, which provides for better evaporation of the liquid spray. The drug delivery catheter may include, but is not limited to, at least 20 delivery ports, alternatively at least 30 delivery ports, alternatively at least 40 delivery ports, alternatively at least 50 delivery ports, alternatively at least 60 delivery ports. Use of such a drug delivery catheter with nebulizing delivery ports may provide more accurate dosing than existing nasal delivery systems, which suffer from problems of liquid dripping down the patient's throat.

The drug could be provided in a liquid suspension or a mixture. The liquid suspension could utilize various liquid carriers, depending on the drug. Liquid carriers include, but are not limited to, water, saline, PFC, and combinations thereof. Use of saline as a carrier has an advantage in that may drugs are already sold with saline as the carrier. Additionally, there are no suspension problems. Use of a PFC as a carrier has an advantage in that, because the PFC would evaporate, the drug would not be diluted.

Drugs that may be delivered using an intranasal delivery catheter include, but are not limited to, neuroprotective agents and malignant hyperthermia, insulin, β-blockers, β-agonists, antihistamines, contraceptives, anesthetics, painkillers, antibiotics, steroids, aspirin, sumatriptan, Viagra, nitroglycerin, hormones, neurodrugs, anti-convulsants, prozac, anti-epileptics, analgesics, NMDA antagonists, narcan, noxone, naltrexone, anxiolytics, and muscle relaxants.

Other Nasal Catheter Designs

Figure 36:
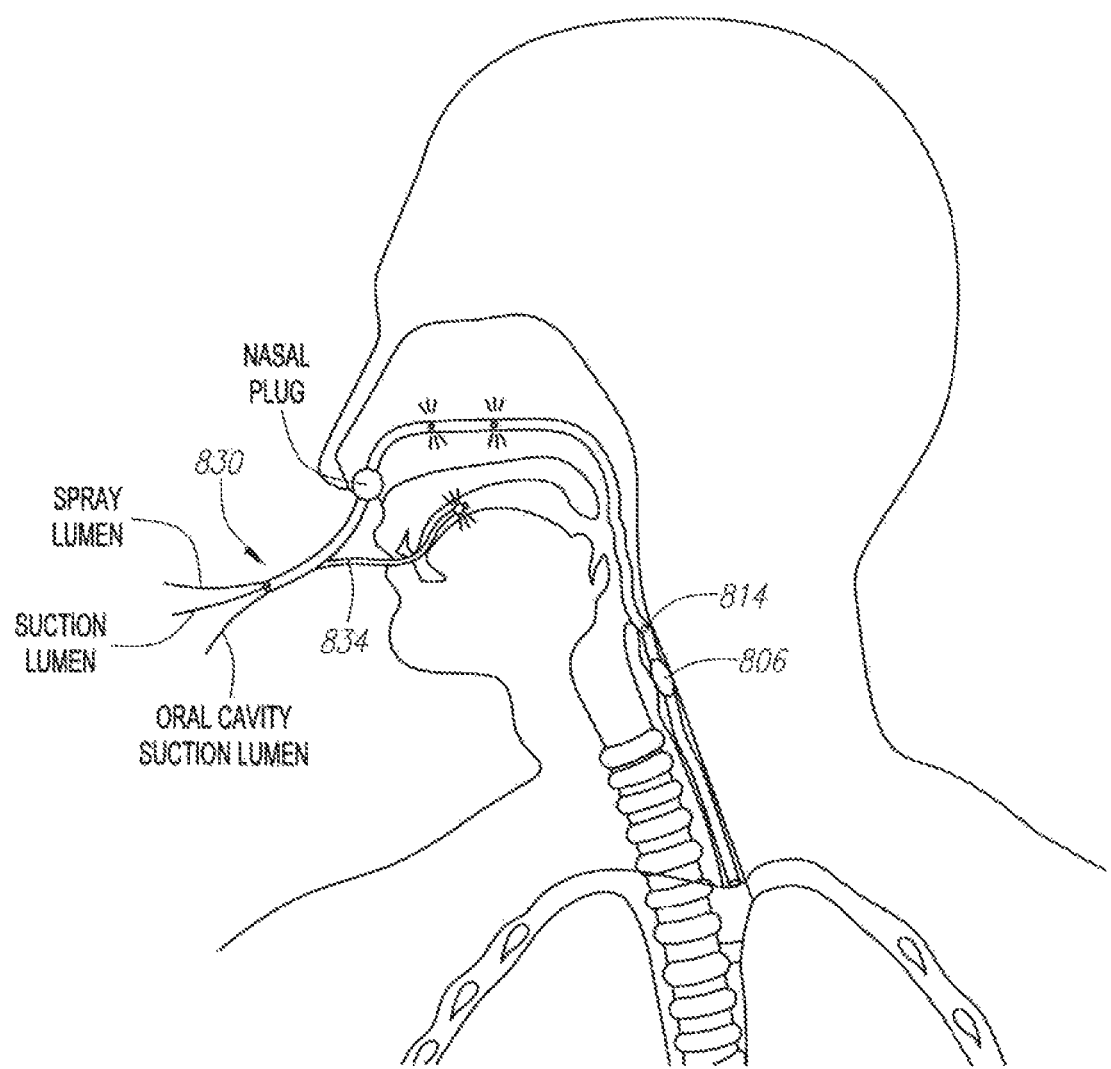
FIG. 36 illustrates an embodiment of a device for delivering a liquid to the nasal and oral cavity according to the present invention

In art alternative embodiment as seen in FIGS. 32A-B and 33-36, specialized nasal catheter 800 is described for the application of a nebulized liquid, preferably a perfluorocarbon (PFC), for cerebral and systemic cooling. This embodiment comprises a multi-lumen elongate member 802 with a length operable to extend a patient's esophagus to be inserted through the nose, and into the esophagus 804. Here, balloon 806 is located near the distal end. This may be used to occlude the esophagus 804. Catheter 800 includes at least a first, second, and third lumen. First lumen 810 of the elongate member may then be used for suctioning vapor and or liquid from the stomach. Second lumen 812 may be exposed proximal to balloon through port 814, to allow suctioning vapor or liquid which enters the upper esophagus. Third lumen 816, which is in fluid communication with multiple ports along catheter 800, may be used as a spray lumen. Fourth lumen is a balloon inflation lumen and is in fluid communication with a chamber defined by balloon 806. In operation, catheter 800 is placed and balloon 806 inflated to occlude the respective passage, i.e., the esophagus. Gastric suction through lumen 810 can be applied per clinical practice. Air (or oxygen) is introduced to the patient through the spray lumen 816 and multiple ports 820 positioned in the nasal cavity. A PFC liquid is added to spray lumen 816; this will produce a fog of droplets in the nasal cavity. Much of the PFC liquid will impact and coalesce on the walls of the nasal cavity and associated passages. This will then drain down to the throat, the majority of which will enter the esophagus where it can be suctioned through the proximal suction port and reused. Some of the PFC may enter the lungs either directly as liquid or as droplets carried on the inhaled breath In addition, as seen in FIGS. 33-36, plug or balloon 822 may be located at the entrance to the nasal cavity to prevent any retrograde flow out of the nose. In an alternate embodiment, the elongate member may be bifurcated outside the nose, with an additional prong and balloon (not shown) for the other nostril. Furthermore, as seen in FIG. 36, catheter 830 may be bifurcated near the proximal end into two tubular members 832 and 834 for delivery of liquid and/or oxygen to the nasal and oral cavities, respectively. With respect to the oral cavity, a second elongate member could be slideably inserted into tubular member 834 for delivering liquid and/or oxygen to the oral cavity. Alternatively, the elongate tubular member inserted into the oral cavity may be independent of the nasal catheter (not shown).

The advantages of this invention include: relative ease of placement; available port provides same function as nasogastric tube; similarity to standard nasogastric tubes in design and use; ease of breathing, speaking, etc., through mouth for the patient; liquid flow rate is not dependant on ventilation and can be set by clinician; high turnover flow through cooling enabled; utilization of well perfused anatomical features; perfluorocarbon is well tolerated in lungs; perfluorocarbon in the stomach is also tolerated, and can be easily suctioned with the gastric portion of the catheter.

The compositions of the invention include liquids having a boiling point of about 38-300° C., more preferably a boiling point of about 38-200° C., more preferably a boiling point of about 60-150° C., more preferably a boiling point of about 70-125° C., more preferably a boiling point of about 75-110° C., more preferably a boiling point of about 60-70° C. Compounds having suitable characteristics for use herein include hydrocarbons, fluorocarbons, perfluorocarbons, and perfluorohydrocarbons. Saline is another example of a substance having suitable characteristics for use herein. As used in this specification, the terms "fluorocarbon," "perfluorocarbon," and "perfluorohydrocarbon" are synonymous. In addition to containing carbon and fluorine, these compounds may also contain other atoms. In one embodiment, the compounds could contain a heteroatom, such as nitrogen, oxygen, or sulfur, or a halogen, such as bromine or chlorine. These compounds may be linear, branched, or cyclic, saturated or unsaturated, or any combination thereof.

In another embodiment, the compounds are highly fluorinated compounds, which are compounds containing at least three fluorine atoms. These highly fluorinated compounds may also contain other atoms besides carbon and fluorine. These other atoms include, but are not limited to, hydrogen; heteroatoms such as oxygen, nitrogen, and sulfur; and halogens such as bromine or chlorine. In one embodiment, the number of the atoms in the compound. These highly fluorinated compounds may be linear, branched, or cyclic, saturated or unsaturated, or any combination thereof. Examples of these compounds include, but are not limited to, $C_4F_9Br$ (b.p. 43° C.), $CF_3CF(CF_3)CF=CF_2$ (b.p. 51° C.), and $CF_3CF(CF_3)CH=CH_2$.

In another embodiment, the compounds use hydrofluorocarbons, which are compounds where the number of hydrogen atoms exceeds the number of fluorine atoms. These hydrofluorocarbons may also contain other atoms besides hydrogen, carbon, and fluorine. These other atoms include, but are not limited to, heteroatoms such as oxygen, nitrogen, and sulfur and halogens such as chlorine and bromine. For example, hydrofluorocarbons include, but are not limited to, hydrochlorofluorocarbons, more specifically, hydrochlorofluoralkanes. In one embodiment, the number of the atoms other than carbon and fluorine comprise a minority of the total number of atoms in the compound. These hydrofluorocarbons may be linear, branched, or cyclic, saturated or unsaturated, or any combination thereof.

A mixture of two or more highly fluorinated compounds, hydrofluorocarbons, light fluorocarbons, hydrocarbons, fluorocarbons, perfluorocarbons, perfluorohydrocarbons, or any of the above-mentioned compounds may also be used. The mixture may contain any of the previously mentioned compounds in different phases (e.g., one gas, one liquid). The mixture has a boiling point above 37° C., even though any individual component of the mixture may have a boiling point below 37° C.

Light fluorocarbons are fluorocarbons that have a boiling point below 37° C. These light fluorocarbons may also contain other atoms besides carbon, and fluorine. These other atoms include, but are not limited to, hydrogen; heteroatoms such as oxygen, nitrogen, and sulfur; and halogens such as chlorine and bromine. For example, light fluorocarbons include, but are not limited to perfluorobutane and perfluoropentane. In one embodiment, the number of the atoms other than carbon and fluorine comprise a minority of the total number of atoms in the compound. These light fluorocarbons may be linear, branched, or cyclic, saturated or unsaturated, or any combination thereof.

In certain methods, a liquid having a boiling point of 38-300° C., more preferably having a boiling point of 38-200° C. more preferably having a boiling point of 38-150° C., is selected. The liquid is nebulized to form a mist. The droplets preferably range in size from 0.1-100 microns, more preferably 1-5 microns, more preferably 2-4 microns. The mist is optionally cooled below body temperature and delivered to the airway of a patient so that the patient inhales the mist. Inhalation of the mist causes systemic cooling by heat transfer from the lungs to the cooler mist and/or by evaporative heat loss as the mist evaporates.

The administration of the liquid is continued mail the systemic temperature is reduced to 35° C. or below, more preferably to 34° C. or below, more preferably to 33° C. or below. The rate of cooling can be adjusted by varying the temperature of the inhalate, the concentration of the responsible compound or compound mixture, the rate of delivery, the particle size, and the percentage of each compound in the mixture.

Nitric oxide or adrenergic agents, such as adrenaline (epinephrine) or albuterol, may be added in minute doses to the compositions described in any of the previously described embodiments. The NO or other agent is inhaled and acts as a potent nasal vasodilator, which improves the rate of action of she cooling mist and counteracts nasal vasoconstriction caused by administering cold substances to the nasal cavity. The NO may be included in an amount of about 2 m about 80 parts per million, in other cases in an amount of about 3 to about 20 parts per million. In other cases in an amount of about 4 to about 10 parts per million, in other cases in an amount of about 5 to about 8 parts per million, in other cases in an amount of about 5 parts per million.

In other methods, administration of cold mists will occur in cycles with intervening cycles of administering another gas, preferably a cold dry gas such as dry air or dry heliox, e.g., a mixture of helium and oxygen. With continuous administration of perfluorocarbon mist, the gaseous phase in the nasal cavity may become saturated with gaseous PFC, thereby slowing the rate of evaporative heat loss. In order to accelerate the rate of evaporative heat loss, it may be desired to periodically purge nasal cavity of perfluorocarbon. This can be done by cycling administration of cold mists with administering another gas, preferably a dry gas such as dry air or dry heliox.

Where cycling is desired, it is recommended that the cycles occur for about 3 seconds or more, in other cases for about 30 seconds or more, in other cases for about one minute or more, in other cases for about two minutes or more, in other cases for about five minutes or more, in other cases for about ten minutes or more, in other cases for about 30 minutes or more. The intervening cycle of dry gas may last for an equal period (e.g., about 3 seconds of cold mist followed by about 3 seconds of dry gas, about 30 seconds of cold mist followed by about 30 seconds of dry gas, about one minute of cold mist followed by about one minute of dry gas, about two minutes of cold mist followed by about two minutes of dry gas, about five minutes of cold mist followed by about five minutes of dry gas, about ten minutes of cold mist followed by about ten minutes of dry gas, about 30 minutes of cold mist followed by about 30 minutes of dry gas, or for a shorter or longer period (about ten minutes of cold mist followed by about two minutes of dry gas).

In certain methods, a liquid having a boiling point of 38-300° C. is selected. The liquid is nebulized to form a mist. The droplets preferably range in size from 1-5 microns. The mist is delivered to the nasal and or oral cavities of a patient so that the patient, of the mist causes cerebral cooling by heat transfer to the cooler mist and/or by evaporative heat loss. In addition indirect hematogenous cooling occurs through the carotids as they pass by the oropharynx and through the Circle of Willis which lies millimeters away from the pharynx. The administration of the liquid is continued until the cerebral temperature is reduced to 35° C. or below, more preferably to 34° C. or below, more preferably to 33° C. or below. In certain methods, the administration of the liquid may be continued to provide for systemic cooling as well as cerebral cooling. In certain methods, the liquid may be cooled to below body temperature before delivery. The mist droplets may range in size from 1-5 microns.

The table in FIG. 37 lists the parameters and results for cerebral cooling trials where the perfluorocarbon mixture used and the flow rate at which it was provided were varied. The column entitled "PFC" lists the perfluorocarbons used and the column entitled "PFC flow mL/min" lists the flow rate at which the PFC was administered. As seen from the "Cooling Rate" data, the faster the rate of administration of PFC, the greater the cooling. The gas flow rate is listed in the column entitled "$O_2$ Flow L/min;" the greater the gas flow rate, the greater the cooling. In this experiment, the gas joined the liquid in a box and generated a spray. The spray was then delivered to the nasal cavity. Possible nasal trauma limited the speed of delivery; for example, nasal bleeding may be rate limiting. The ration between the gas and the liquid was varied (e.g., 1:1, 1:2, 1:3) with varying effect on cooling rates. The column entitled "BIAS flow" is CPAP (continuous positive airway pressure) air under several atmospheres of pressure to enhance spray entry during inspiration. Cooling was measured in Head-F (frontal lobe of the brain), Head V (ventricle of the brain), Head-S (superficial, cortical, and posterior portions of the brain), Vasc (vascular column), and Rectal (rectal column). Systemic column was measured in the vascular column. From the measurements it appears that Head F cools first and the fastest. Subsequently, the cold diffuses back to the ventricle and then to surface. A gradient is created within the brain and between brain and blood, such that brain cooling is more marked early on (20-30 degrees in one hour) than blood (10 degrees in one hour), systemic cooling, or rectal cooling. This gradient eventually disappears.

Figure 38:
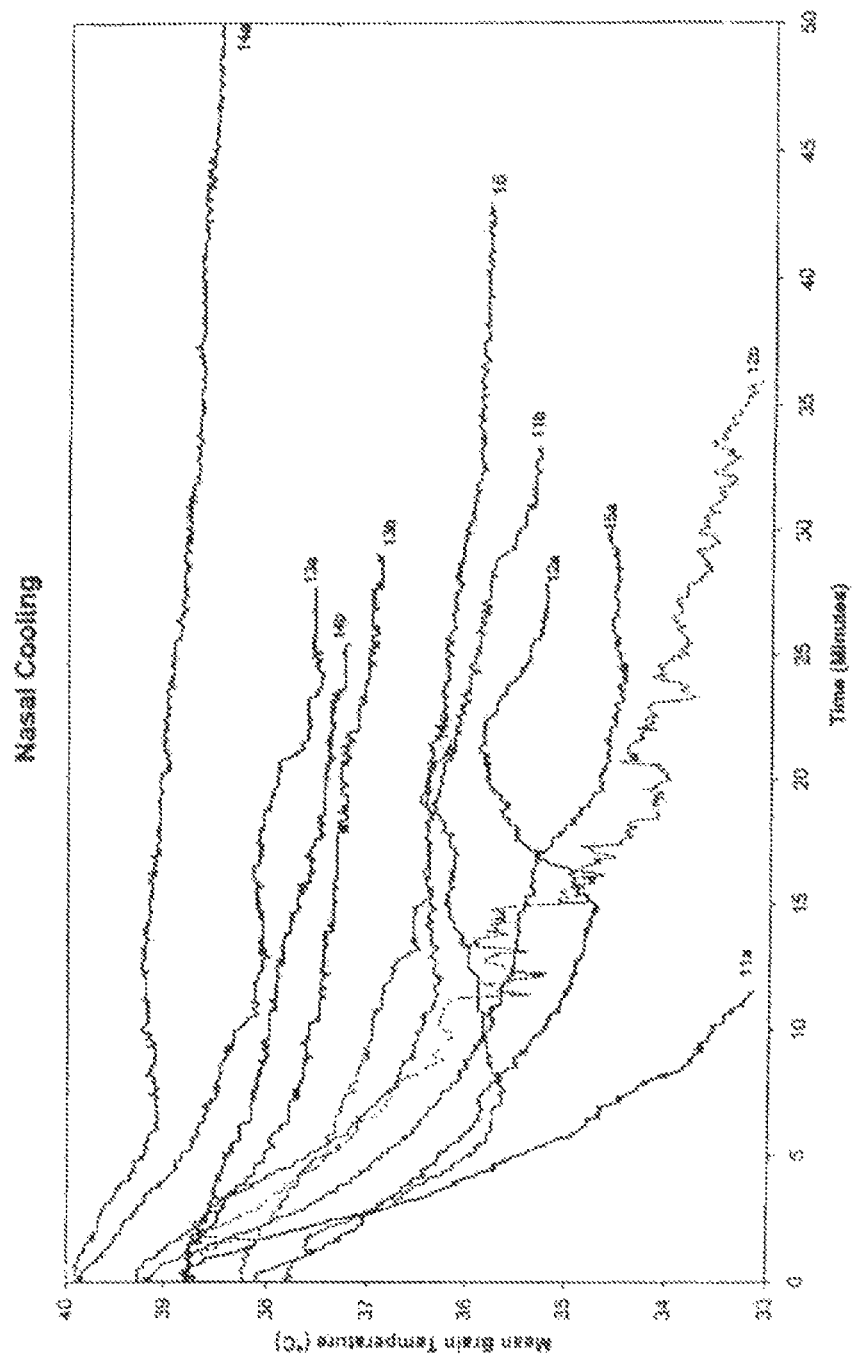
FIG. 38 is a graph of is of brain temperatures against time for different runs listed in FIG. 37.

FIG. 38 shows a plot of brain temperature against time for different runs listed in FIG. 37. Table 1 (below) shows additional experimental data wherein the cooling liquid and the flow rate were varied.

TABLE 1

| TIME | 1:HEAD-F | 1:HEAD-V | HEAD-S | 1:ESOPH | 1:IM | 1:SUBQ | 1:RECTAL |
|---|---|---|---|---|---|---|---|
| 12:26:52 | 37.7 | 38.1 | 38.5 | 36.8 | 38.5 | 36.7 | 38.4 |
| 12:26:56 | 37.7 | 38.1 | 38.5 | 36.7 | 38.5 | 36.7 | 38.4 |
| 12:27:01 | 37.7 | 38.1 | 38.5 | 36.5 | 38.4 | 36.7 | 38.4 |
| 12:27:05 | 37.7 | 38.1 | 38.5 | 35.8 | 38.4 | 36.7 | 38.4 |
| 12:27:09 | 37.7 | 38.1 | 38.5 | 35.2 | 38.4 | 36.7 | 38.3 |
| 12:27:13 | 37.6 | 38.1 | 38.5 | 35 | 38.4 | 36.7 | 38.4 |
| 12:27:17 | 37.6 | 38 | 38.4 | 34.6 | 38.4 | 36.7 | 38.3 |
| 12:27:21 | 37.6 | 37.9 | 38.4 | 34.2 | 38.4 | 36.7 | 38.3 |
| 12:27:26 | 37.5 | 37.8 | 38.4 | 34 | 38.4 | 36.7 | 38.4 |
| 12:27:30 | 37.4 | 37.8 | 38.5 | 33.3 | 38.5 | 36.7 | 38.4 |
| 12:27:34 | 37.3 | 37.7 | 38.5 | 33.1 | 38.4 | 36.7 | 38.3 |
| 12:27:38 | 37.3 | 37.7 | 38.4 | 32.9 | 38.4 | 36.7 | 38.3 |

TABLE 1-continued

| | | | | | | | |
|---|---|---|---|---|---|---|---|
| 12:27:42 | 37.2 | 37.6 | 38.4 | 32.8 | 38.3 | 36.7 | 38.3 |
| 12:27:46 | 37.1 | 37.6 | 38.4 | 32.5 | 38.3 | 36.7 | 38.3 |
| 12:27:50 | 37.1 | 37.5 | 38.3 | 32.5 | 38.4 | 36.7 | 38.4 |
| 12:27:55 | 37 | 37.5 | 38.3 | 32.3 | 38.4 | 36.7 | 38.3 |
| 12:27:59 | 36.9 | 37.4 | 38.3 | 32.2 | 38.4 | 36.7 | 38.3 |
| 12:28:03 | 36.9 | 37.4 | 38.3 | 32.2 | 38.4 | 36.7 | 38.3 |
| 12:28:07 | 36.8 | 37.4 | 38.3 | 32.2 | 38.5 | 36.7 | 38.3 |
| 12:28:11 | 36.7 | 37.3 | 38.3 | 32.1 | 38.4 | 36.7 | 38.4 |
| 12:28:15 | 36.7 | 37.3 | 38.3 | 31.8 | 38.4 | 36.7 | 38.3 |
| 12:28:20 | 36.7 | 37.3 | 38.3 | 31.7 | 38.4 | 36.7 | 38.4 |
| 12:28:24 | 36.6 | 37.2 | 38.3 | 31.6 | 38.4 | 36.8 | 38.4 |
| 12:28:28 | 36.4 | 37.2 | 38.2 | 31.5 | 38.4 | 36.7 | 38.4 |
| 12:28:32 | 36.5 | 37.2 | 38.3 | 31.3 | 38.5 | 36.7 | 38.3 |
| 12:28:36 | 36.5 | 37.1 | 38.2 | 31.2 | 38.4 | 36.7 | 38.4 |
| 12:28:40 | 36.5 | 37.1 | 38.2 | 31.1 | 38.4 | 36.7 | 38.3 |
| 12:28:44 | 36.4 | 37.1 | 38.2 | 31.1 | 38.4 | 36.8 | 38.4 |
| 12:28:49 | 36.3 | 37.1 | 38.2 | 31 | 38.4 | 36.7 | 38.3 |
| 12:28:53 | 36.3 | 37 | 38.1 | 30.9 | 38.4 | 36.7 | 38.3 |
| 12:28:57 | 36.2 | 37 | 38.1 | 30.9 | 38.4 | 36.7 | 38.4 |
| 12:29:01 | 36.2 | 37 | 38.1 | 30.8 | 38.4 | 36.7 | 38.3 |
| 12:29:05 | 36.2 | 37 | 38.1 | 30.7 | 38.4 | 36.7 | 38.3 |
| 12:29:09 | 36.1 | 36.9 | 38.1 | 29.9 | 38.4 | 36.7 | 38.3 |
| 12:29:13 | 36.1 | 36.9 | 38.1 | 29.8 | 38.4 | 36.7 | 38.3 |
| 12:29:18 | 36.1 | 37 | 38.1 | 30 | 38.4 | 36.7 | 38.3 |
| 12:29:22 | 36 | 37 | 38.1 | 30.1 | 38.4 | 36.7 | 38.3 |
| 12:29:26 | 36.1 | 37 | 38.1 | 30.5 | 38.4 | 36.7 | 38.3 |
| 12:29:30 | 36 | 37 | 38 | 30.5 | 38.4 | 36.7 | 38.3 |
| 12:29:34 | 36 | 37 | 38 | 30.6 | 38.5 | 36.7 | 38.3 |
| 12:29:38 | 36 | 36.9 | 38 | 30.6 | 38.4 | 36.7 | 38.3 |
| 12:29:43 | 36 | 36.9 | 38 | 30.6 | 38.4 | 36.7 | 38.3 |
| 12:29:47 | 35.9 | 36.8 | 38 | 30.2 | 38.4 | 36.7 | 38.3 |
| 12:29:51 | 35.9 | 36.8 | 38 | 30.3 | 38.4 | 36.7 | 38.3 |
| 12:29:55 | 35.9 | 36.8 | 38 | 30.2 | 38.4 | 36.7 | 38.3 |
| 12:29:59 | 35.8 | 36.8 | 37.9 | 30.3 | 38.4 | 36.7 | 38.3 |
| 12:30:03 | 35.8 | 36.8 | 38 | 30.3 | 38.4 | 36.7 | 38.3 |
| 12:30:07 | 35.8 | 36.7 | 37.9 | 30.5 | 38.4 | 36.7 | 38.3 |
| 12:30:12 | 35.7 | 36.7 | 37.8 | 30.5 | 38.4 | 36.7 | 38.3 |
| 12:30:16 | 35.7 | 36.7 | 37.9 | 30.6 | 38.5 | 36.7 | 38.3 |
| 12:30:20 | 35.7 | 36.7 | 37.8 | 30.6 | 38.4 | 36.7 | 38.3 |
| 12:30:24 | 35.7 | 36.6 | 37.8 | 30.6 | 38.4 | 36.7 | 38.3 |
| 12:30:28 | 35.6 | 36.6 | 37.8 | 30.5 | 38.4 | 36.7 | 38.3 |
| 12:30:32 | 35.6 | 36.6 | 37.8 | 30.2 | 38.4 | 36.7 | 38.3 |
| 2:30:36 | 35.6 | 36.6 | 37.8 | 30.5 | 38.4 | 36.7 | 38.3 |
| 12:30:41 | 35.6 | 36.6 | 37.7 | 30.5 | 38.4 | 36.7 | 38.3 |
| 12:30:45 | 35.5 | 36.5 | 37.7 | 30.3 | 38.4 | 36.7 | 38.2 |
| 12:30:49 | 35.5 | 36.5 | 37.7 | 30.2 | 38.4 | 36.7 | 38.3 |
| 12:30:53 | 35.5 | 36.5 | 37.7 | 30.2 | 38.4 | 36.7 | 38.3 |
| 12:30:57 | 35.5 | 36.5 | 37.7 | 30.1 | 38.4 | 36.7 | 38.2 |
| 12:31:01 | 35.3 | 36.4 | 37.6 | 30.2 | 38.3 | 36.6 | 38.2 |
| 12:31:06 | 35.3 | 36.4 | 37.6 | 30.1 | 38.4 | 36.7 | 38.2 |
| 12:31:10 | 35.3 | 36.5 | 37.6 | 30.1 | 38.4 | 36.7 | 38.2 |
| 12:31:14 | 35.3 | 36.5 | 37.6 | 30 | 38.4 | 36.6 | 38.2 |
| 12:31:18 | 35.3 | 36.5 | 37.6 | 30.1 | 38.4 | 36.7 | 38.3 |
| 12:31:22 | 35.2 | 36.4 | 37.6 | 30.2 | 38.4 | 36.7 | 38.2 |
| 12:31:26 | 35.2 | 36.4 | 37.6 | 30.2 | 38.4 | 36.7 | 38.2 |
| 12:31:30 | 35.2 | 36.3 | 37.6 | 30.2 | 38.4 | 36.7 | 38.2 |
| 12:31:35 | 35.1 | 36.3 | 37.5 | 30.1 | 38.4 | 36.6 | 38.2 |
| 12:31:39 | 35.1 | 36.3 | 37.5 | 30.1 | 38.3 | 36.6 | 38.2 |
| 12:31:43 | 35.1 | 36.3 | 37.5 | 30.2 | 38.4 | 36.7 | 38.2 |
| 12:31:47 | 35.1 | 36.3 | 37.5 | 30.1 | 38.4 | 36.6 | 38.2 |
| 12:31:51 | 35.1 | 36.3 | 37.5 | 30.1 | 38.3 | 36.7 | 38.2 |
| 12:31:55 | 35.1 | 36.3 | 37.4 | 30.2 | 38.4 | 36.6 | 38.2 |
| 12:31:59 | 35.1 | 36.3 | 37.5 | 30.2 | 38.3 | 36.6 | 38.2 |
| 12:32:04 | 35 | 36.2 | 37.4 | 30.1 | 38.4 | 36.6 | 38.2 |
| 12:32:08 | 35 | 36.2 | 37.4 | 30.1 | 38.4 | 36.6 | 38.2 |
| 12:32:12 | 35 | 36.2 | 37.4 | 30.1 | 38.4 | 36.6 | 38.2 |
| 12:32:16 | 34.9 | 36.2 | 37.4 | 30.1 | 38.4 | 36.6 | 38.2 |
| 12:32:20 | 34.9 | 36.2 | 37.4 | 30.1 | 38.4 | 36.6 | 38.2 |
| 12:32:24 | 34.9 | 36.1 | 37.3 | 30.1 | 38.4 | 36.6 | 38.2 |
| 12:32:29 | 34.8 | 36.1 | 37.3 | 30.1 | 38.4 | 36.6 | 38.2 |
| 12:32:33 | 34.8 | 36.1 | 37.3 | 30 | 38.4 | 36.7 | 38.2 |
| 12:32:37 | 34.8 | 36.1 | 37.3 | 30 | 38.3 | 36.6 | 38.1 |
| 12:32:41 | 34.8 | 36.1 | 37.2 | 29.8 | 38.3 | 36.6 | 38.1 |
| 12:32:45 | 34.8 | 36.1 | 37.2 | 29.8 | 38.3 | 36.6 | 38.2 |
| 12:32:49 | 34.8 | 36 | 37.2 | 29.8 | 38.4 | 36.6 | 38.2 |
| 12:32:53 | 34.7 | 36 | 37.2 | 29.8 | 38.4 | 36.6 | 38.2 |
| 12:32:58 | 34.7 | 36 | 37.2 | 29.8 | 38.3 | 36.6 | 38.2 |
| 12:33:02 | 34.7 | 36 | 37.1 | 29.8 | 38.3 | 36.6 | 38.1 |
| 12:33:06 | 34.7 | 36 | 37.1 | 29.5 | 38.3 | 36.6 | 38.1 |
| 12:33:10 | 34.7 | 36 | 37.1 | 29.5 | 38.3 | 36.6 | 38.1 |

TABLE 1-continued

| | | | | | | | |
|---|---|---|---|---|---|---|---|
| 12:33:14 | 34.7 | 36 | 37.1 | 29.5 | 38.3 | 36.6 | 38.2 |
| 12:33:18 | 34.6 | 35.9 | 37.1 | 29.5 | 38.3 | 36.6 | 38.1 |
| 12:33:23 | 34.6 | 36 | 37.1 | 29.5 | 38.4 | 36.6 | 38.1 |
| 12:33:27 | 34.6 | 36 | 37.1 | 29.5 | 38.4 | 36.6 | 38.1 |
| 12:33:31 | 34.6 | 35.9 | 37.1 | 29.5 | 38.3 | 36.6 | 38.1 |
| 12:33:35 | 34.6 | 35.9 | 37.1 | 29.4 | 38.3 | 36.6 | 38.1 |
| 12:33:39 | 34.6 | 35.9 | 37 | 29.3 | 38.3 | 36.6 | 38.1 |
| 12:33:43 | 34.6 | 36 | 37 | 29.4 | 38.4 | 36.6 | 38.1 |
| 12:33:47 | 34.6 | 36 | 37 | 29.3 | 38.3 | 36.6 | 38.1 |
| 12:33:52 | 34.6 | 36 | 37 | 29.3 | 38.3 | 36.6 | 38.1 |
| 12:33:56 | 34.6 | 36 | 37 | 29.2 | 38.3 | 36.6 | 38.1 |
| 12:34:00 | 34.7 | 36 | 37 | 29.2 | 38.3 | 36.6 | 38.1 |
| 12:34:04 | 34.7 | 36 | 37 | 29.2 | 38.4 | 36.7 | 38.2 |
| 12:34:08 | 34.6 | 36 | 37 | 29.1 | 38.3 | 36.6 | 38.1 |
| 12:34:12 | 34.6 | 36 | 37 | 29.2 | 38.3 | 36.6 | 38.1 |
| 12:34:16 | 34.6 | 36 | 37 | 29.1 | 38.3 | 36.6 | 38.1 |
| 12:34:21 | 34.6 | 36 | 36.9 | 29.1 | 38.3 | 36.6 | 38.1 |
| 12:34:25 | 34.6 | 36 | 36.9 | 29 | 38.3 | 36.6 | 38.1 |
| 12:34:29 | 34.6 | 35.9 | 37 | 29 | 38.4 | 36.6 | 38.1 |
| 12:34:33 | 34.5 | 35.9 | 36.9 | 29 | 38.3 | 36.6 | 38.1 |
| 12:34:37 | 34.5 | 35.9 | 36.9 | 28.9 | 38.3 | 36.6 | 38.1 |
| 12:34:41 | 34.5 | 35.9 | 36.9 | 28.9 | 38.3 | 36.6 | 38.1 |
| 12:34:46 | 34.5 | 35.9 | 36.9 | 28.9 | 38.3 | 36.6 | 38.1 |
| 12:34:50 | 34.5 | 35.8 | 36.8 | 28.8 | 38.3 | 36.6 | 38.1 |
| 12:34:54 | 34.5 | 35.8 | 36.8 | 28.8 | 38.3 | 36.6 | 38.1 |
| 12:34:58 | 34.5 | 35.8 | 36.8 | 29 | 38.3 | 36.6 | 38.1 |
| 12:35:02 | 34.4 | 35.8 | 36.8 | 29.1 | 38.3 | 36.6 | 38.1 |
| 12:35:06 | 34.5 | 35.8 | 36.8 | 29.1 | 38.3 | 36.6 | 38.1 |
| 12:35:11 | 34.4 | 35.7 | 36.8 | 29 | 38.3 | 36.5 | 38.1 |
| 12:35:15 | 34.3 | 35.7 | 36.8 | 29 | 38.3 | 36.6 | 38 |
| 12:35:19 | 34.3 | 35.7 | 36.8 | 29 | 38.3 | 36.6 | 38.1 |
| 12:35:23 | 34.2 | 35.6 | 36.7 | 28.9 | 38.3 | 36.6 | 38 |
| 12:35:27 | 34.2 | 35.6 | 36.7 | 29 | 38.3 | 36.5 | 38 |
| 12:35:31 | 34.2 | 35.6 | 36.7 | 29.1 | 38.3 | 36.5 | 38 |
| 12:35:35 | 34.2 | 35.7 | 36.7 | 29.1 | 38.3 | 36.5 | 38 |
| 12:35:40 | 34.2 | 35.7 | 36.7 | 29.1 | 38.3 | 36.5 | 38.1 |
| 12:35:44 | 34.2 | 35.7 | 36.7 | 29.2 | 38.3 | 36.5 | 38 |
| 12:35:48 | 34.2 | 35.6 | 36.7 | 29.2 | 38.3 | 36.5 | 38 |
| 12:35:52 | 34.2 | 35.6 | 36.6 | 29.2 | 38.3 | 36.5 | 38 |
| 12:35:56 | 34.1 | 35.5 | 36.6 | 29.2 | 38.3 | 36.5 | 38 |
| 12:36:00 | 34.1 | 35.6 | 36.7 | 29.1 | 38.3 | 36.5 | 38 |
| 12:36:04 | 34.1 | 35.5 | 36.6 | 29.2 | 38.3 | 36.5 | 38.1 |
| 12:36:09 | 34.1 | 35.5 | 36.6 | 29.2 | 38.3 | 36.5 | 38 |
| 12:36:13 | 34.1 | 35.5 | 36.6 | 29.2 | 38.3 | 36.5 | 38 |
| 12:36:17 | 34 | 35.5 | 36.6 | 29.2 | 38.3 | 36.5 | 38 |
| 12:36:21 | 34 | 35.5 | 36.6 | 29.2 | 38.3 | 36.5 | 38 |
| 12:36:25 | 34 | 35.5 | 36.6 | 29.3 | 38.3 | 36.5 | 37.9 |
| 12:36:29 | 34 | 35.5 | 36.5 | 28.9 | 38.3 | 36.5 | 38 |
| 12:36:34 | 34 | 35.5 | 36.5 | 29 | 38.3 | 36.5 | 38 |
| 12:36:38 | 34 | 35.5 | 36.5 | 29.1 | 38.3 | 36.5 | 38 |
| 12:36:42 | 33.9 | 35.4 | 36.5 | 29.1 | 38.3 | 36.5 | 38 |
| 12:36:46 | 33.9 | 35.4 | 36.5 | 29.2 | 38.3 | 36.5 | 38 |
| 12:36:50 | 33.9 | 35.3 | 36.5 | 29.2 | 38.3 | 36.5 | 38 |
| 12:36:54 | 33.8 | 35.4 | 36.5 | 29.2 | 38.3 | 36.5 | 38 |
| 12:36:58 | 33.8 | 35.3 | 36.5 | 29.2 | 38.2 | 36.5 | 38 |
| 12:37:03 | 33.8 | 35.4 | 36.5 | 29.2 | 38.3 | 36.5 | 38 |
| 12:37:07 | 33.8 | 35.3 | 36.5 | 29.2 | 38.3 | 36.4 | 38 |
| 12:37:11 | 33.8 | 35.3 | 36.5 | 29.2 | 38.3 | 36.5 | 38 |
| 12:37:15 | 33.8 | 35.3 | 36.4 | 29.2 | 38.2 | 36.4 | 37.9 |
| 12:37:19 | 33.8 | 35.3 | 36.5 | 29.3 | 38.3 | 36.5 | 38 |
| 12:37:23 | 33.8 | 35.3 | 36.4 | 29.2 | 38.3 | 36.5 | 38 |
| 12:37:28 | 33.8 | 35.3 | 36.4 | 29.2 | 38.2 | 36.5 | 37.9 |
| 12:37:32 | 33.8 | 35.3 | 36.4 | 29.2 | 38.2 | 36.4 | 37.9 |
| 12:37:36 | 33.7 | 35.2 | 36.3 | 29.2 | 38.2 | 36.4 | 37.9 |
| 12:37:40 | 33.7 | 35.2 | 36.4 | 29.2 | 38.2 | 36.4 | 38 |
| 12:37:44 | 33.7 | 35.2 | 36.4 | 29.2 | 38.2 | 36.5 | 38 |
| 12:37:48 | 33.7 | 35.2 | 36.3 | 29.2 | 38.2 | 36.4 | 37.9 |
| 12:37:53 | 33.7 | 35.2 | 36.3 | 28.7 | 38.3 | 36.4 | 37.9 |
| 12:37:57 | 33.7 | 35.2 | 36.3 | 28.7 | 38.2 | 36.4 | 37.9 |
| 12:38:01 | 33.7 | 35.2 | 36.3 | 28.7 | 38.3 | 36.5 | 37.9 |
| 12:38:05 | 33.7 | 35.2 | 36.3 | 28.7 | 38.3 | 36.5 | 38 |
| 12:38:09 | 33.6 | 35.2 | 36.3 | 28.6 | 38.2 | 36.4 | 37.9 |
| 12:38:13 | 33.6 | 35.2 | 36.3 | 28.6 | 38.2 | 36.4 | 37.9 |
| 12:38:17 | 33.6 | 35.2 | 36.2 | 28.6 | 38.2 | 36.4 | 37.8 |
| 12:38:21 | 33.6 | 35.2 | 36.3 | 28.6 | 38.2 | 36.5 | 37.9 |
| 12:38:25 | 33.6 | 35.2 | 36.3 | 28.6 | 38.3 | 36.5 | 37.9 |
| 12:38:30 | 33.6 | 35.1 | 36.2 | 28.5 | 38.2 | 36.4 | 37.8 |
| 12:38:34 | 33.6 | 35.2 | 36.2 | 28.5 | 38.3 | 36.4 | 37.9 |
| 12:38:38 | 33.6 | 35.1 | 36.2 | 28.5 | 38.2 | 36.4 | 37.8 |
| 12:38:42 | 33.6 | 35.1 | 36.1 | 28.4 | 38.2 | 36.3 | 37.8 |

TABLE 1-continued

| | | | | | | | |
|---|---|---|---|---|---|---|---|
| 12:38:46 | 33.6 | 35.1 | 36.2 | 28.3 | 38.2 | 36.4 | 37.8 |
| 12:38:50 | 33.6 | 35.1 | 36.2 | 28.4 | 38.2 | 36.5 | 37.9 |
| 12:38:55 | 33.6 | 35.1 | 36.2 | 28.3 | 38.2 | 36.4 | 37.9 |
| 12:38:59 | 33.6 | 35.1 | 36.1 | 28.4 | 38.2 | 36.4 | 37.8 |
| 12:39:03 | 33.6 | 35.1 | 36.2 | 28.3 | 38.2 | 36.4 | 37.8 |
| 12:39:07 | 33.5 | 35.1 | 36.1 | 28.3 | 38.2 | 36.3 | 37.8 |
| 12:39:11 | 33.6 | 35.1 | 36.1 | 28.3 | 38.2 | 36.3 | 37.8 |
| 12:39:15 | 33.6 | 35.1 | 36.1 | 28.3 | 38.2 | 36.4 | 37.8 |
| 12:39:19 | 33.6 | 35.1 | 36.1 | 28.3 | 38.2 | 36.4 | 37.8 |
| 12:39:24 | 33.5 | 35.1 | 36.1 | 28.2 | 38.2 | 36.3 | 37.8 |
| 12:39:28 | 33.6 | 35.1 | 36.1 | 28.2 | 38.2 | 36.4 | 37.8 |
| 12:39:32 | 33.5 | 35.1 | 36.1 | 28.1 | 38.2 | 36.3 | 37.8 |
| 12:39:36 | 33.6 | 35.1 | 36.1 | 28.2 | 38.2 | 36.4 | 37.8 |
| 12:39:40 | 33.5 | 35 | 36.1 | 28.1 | 38.2 | 36.3 | 37.8 |
| 12:39:44 | 33.6 | 35 | 36 | 28.1 | 38.2 | 36.3 | 37.8 |
| 12:39:49 | 33.6 | 35 | 36 | 28.1 | 38.2 | 36.3 | 37.8 |
| 12:39:53 | 33.5 | 35 | 36 | 28.1 | 38.2 | 36.3 | 37.8 |
| 12:39:57 | 33.5 | 35 | 36 | 28 | 38.2 | 36.3 | 37.8 |
| 12:40:01 | 33.5 | 35 | 36 | 28 | 38.2 | 36.3 | 37.8 |
| 12:40:05 | 33.5 | 35 | 36 | 27.9 | 38.2 | 36.3 | 37.8 |
| 12:40:09 | 33.5 | 35 | 36 | 28 | 38.2 | 36.3 | 37.8 |
| 12:40:13 | 33.5 | 35 | 36 | 27.9 | 38.2 | 36.3 | 37.8 |
| 12:40:18 | 33.5 | 35 | 36 | 27.9 | 38.2 | 36.3 | 37.8 |
| 12:40:22 | 33.5 | 35 | 36 | 27.9 | 38.2 | 36.3 | 37.8 |
| 12:40:26 | 33.5 | 35 | 36 | 27.9 | 38.2 | 36.3 | 37.8 |
| 12:40:30 | 33.5 | 35 | 36 | 27.9 | 38.2 | 36.3 | 37.7 |
| 12:40:34 | 33.5 | 35 | 36 | 27.9 | 38.2 | 36.3 | 37.7 |
| 12:40:38 | 33.5 | 35 | 35.9 | 27.8 | 38.2 | 36.3 | 37.7 |
| 12:40:42 | 33.5 | 35 | 36 | 27.8 | 38.2 | 36.3 | 37.7 |
| 12:40:47 | 33.5 | 35 | 35.9 | 27.8 | 38.1 | 36.3 | 37.8 |
| 12:40:51 | 33.5 | 35 | 36 | 27.7 | 38.2 | 36.3 | 37.7 |
| 12:40:55 | 33.6 | 34.9 | 35.9 | 27.8 | 38.2 | 36.3 | 37.8 |
| 12:40:59 | 33.5 | 34.9 | 35.9 | 27.8 | 38.2 | 36.3 | 37.7 |
| 12:41:03 | 33.5 | 34.9 | 35.9 | 27.7 | 38.2 | 36.3 | 37.7 |
| 12:41:07 | 33.5 | 34.9 | 35.9 | 27.8 | 38.2 | 36.3 | 37.7 |
| 12:41:12 | 33.6 | 34.9 | 35.9 | 27.7 | 38.2 | 36.3 | 37.7 |
| 12:41:16 | 33.5 | 34.9 | 35.9 | 27.7 | 38.2 | 36.3 | 37.7 |
| 12:41:20 | 33.5 | 34.9 | 35.9 | 27.6 | 38.2 | 36.3 | 37.7 |
| 12:41:24 | 33.6 | 34.9 | 35.8 | 27.6 | 38.1 | 36.3 | 37.7 |
| 12:41:28 | 33.5 | 34.9 | 35.8 | 27.6 | 38.1 | 36.3 | 37.7 |
| 12:41:32 | 33.6 | 34.9 | 35.8 | 27.6 | 38.1 | 36.3 | 37.7 |
| 12:41:36 | 33.5 | 34.8 | 35.8 | 27.6 | 38.1 | 36.2 | 37.7 |
| 12:41:41 | 33.6 | 34.9 | 35.8 | 27.6 | 38.1 | 36.3 | 37.7 |
| 12:41:45 | 33.5 | 34.8 | 35.8 | 27.7 | 38.1 | 36.2 | 37.7 |
| 12:41:49 | 33.6 | 34.8 | 35.8 | 27.7 | 38.1 | 36.3 | 37.7 |
| 12:41:53 | 33.6 | 34.8 | 35.8 | 27.8 | 38.1 | 36.3 | 37.7 |
| 12:41:57 | 33.6 | 34.9 | 35.8 | 28 | 38.1 | 36.3 | 37.7 |
| 12:42:01 | 33.6 | 35 | 35.8 | 28 | 38.1 | 36.3 | 37.7 |
| 12:42:05 | 33.7 | 35 | 35.7 | 28.6 | 38.1 | 36.3 | 37.7 |
| 12:42:10 | 33.7 | 35 | 35.8 | 28.3 | 38.1 | 36.3 | 37.7 |
| 12:42:14 | 33.7 | 35 | 35.7 | 28.2 | 38.1 | 36.2 | 37.7 |
| 12:42:18 | 33.8 | 35.1 | 35.8 | 28 | 38.1 | 36.2 | 37.7 |
| 12:42:22 | 33.8 | 35.1 | 35.8 | 27.8 | 38.1 | 36.3 | 37.7 |
| 12:42:26 | 33.9 | 35.1 | 35.7 | 27.7 | 38.1 | 36.3 | 37.7 |
| 12:42:30 | 33.9 | 35.1 | 35.7 | 27.6 | 38.1 | 36.2 | 37.7 |
| 12:42:35 | 34 | 35.1 | 35.8 | 27.6 | 38.1 | 36.3 | 37.7 |
| 12:42:39 | 34 | 35.1 | 35.7 | 27.5 | 38.1 | 36.3 | 37.7 |
| 12:42:43 | 34 | 35.1 | 35.8 | 27.5 | 38.1 | 36.3 | 37.7 |
| 12:42:47 | 34 | 35.1 | 35.7 | 27.4 | 38.1 | 36.3 | 37.7 |
| 12:42:51 | 34 | 35.1 | 35.7 | 27.3 | 38.1 | 36.2 | 37.7 |
| 12:42:55 | 34 | 35.1 | 35.7 | 27.2 | 38.1 | 36.3 | 37.7 |
| 12:42:59 | 34.1 | 35.1 | 35.8 | 27.2 | 38.1 | 36.3 | 37.7 |
| 12:43:04 | 34.1 | 35.1 | 35.8 | 27.2 | 38.1 | 36.3 | 37.7 |
| 12:43:08 | 34 | 35.1 | 35.7 | 27.2 | 38.1 | 36.2 | 37.6 |
| 12:43:12 | 34.1 | 35.1 | 35.7 | 27.3 | 38 | 36.2 | 37.6 |
| 12:43:16 | 34.1 | 35.1 | 35.7 | 27.5 | 38.1 | 36.2 | 37.6 |
| 12:43:20 | 34.2 | 35.2 | 35.7 | 27.5 | 38.1 | 36.2 | 37.6 |
| 12:43:24 | 34.3 | 35.3 | 35.7 | 27.6 | 38.1 | 36.2 | 37.6 |
| 12:43:28 | 34.3 | 35.5 | 35.7 | 27.6 | 38.1 | 36.2 | 37.6 |
| 12:43:33 | 34.4 | 35.5 | 35.7 | 27.5 | 38.1 | 36.2 | 37.6 |
| 12:43:37 | 34.5 | 35.5 | 35.7 | 27.5 | 38.1 | 36.2 | 37.6 |
| 12:43:41 | 34.7 | 35.5 | 35.7 | 27.4 | 38.1 | 36.2 | 37.6 |
| 12:43:45 | 34.7 | 35.5 | 35.8 | 27.4 | 38.1 | 36.2 | 37.6 |
| 12:43:49 | 34.7 | 35.5 | 35.8 | 27.4 | 38.1 | 36.2 | 37.6 |
| 12:43:53 | 34.7 | 35.5 | 35.8 | 27.3 | 38 | 36.2 | 37.6 |
| 12:43:58 | 34.7 | 35.4 | 35.7 | 27.4 | 38.1 | 36.2 | 37.6 |
| 12:44:02 | 34.8 | 35.5 | 35.8 | 27.4 | 38.1 | 36.2 | 37.6 |
| 12:44:06 | 34.8 | 35.6 | 35.8 | 27.5 | 38.1 | 36.2 | 37.6 |
| 12:44:10 | 34.8 | 35.6 | 35.8 | 27.5 | 38 | 36.2 | 37.6 |
| 12:44:14 | 34.9 | 35.6 | 35.8 | 27.5 | 38 | 36.2 | 37.6 |

TABLE 1-continued

| | | | | | | | |
|---|---|---|---|---|---|---|---|
| 12:44:18 | 35 | 35.6 | 35.8 | 27.5 | 38 | 36.2 | 37.6 |
| 12:44:22 | 35 | 35.6 | 35.8 | 27.6 | 38 | 36.2 | 37.6 |
| 12:44:27 | 35.1 | 35.7 | 35.8 | 27.7 | 38.1 | 36.2 | 37.6 |
| 12:44:31 | 35.1 | 35.6 | 35.8 | 27.7 | 38 | 36.2 | 37.6 |
| 12:44:35 | 35.1 | 35.7 | 35.8 | 27.7 | 38 | 36.2 | 37.6 |
| 12:44:39 | 35.1 | 35.6 | 35.8 | 27.7 | 38 | 36.2 | 37.5 |
| 12:44:43 | 35.1 | 35.6 | 35.9 | 27.8 | 38.1 | 36.2 | 37.5 |
| 12:44:47 | 35.1 | 35.6 | 35.9 | 27.8 | 38 | 36.2 | 37.6 |
| 12:44:52 | 35.1 | 35.6 | 35.8 | 27.7 | 38 | 36.2 | 37.6 |
| 12:44:56 | 35.1 | 35.7 | 35.8 | 27.6 | 38 | 36.1 | 37.5 |
| 12:45:00 | 35.1 | 35.7 | 35.8 | 27.6 | 38 | 36.2 | 37.6 |
| 12:45:04 | 35.2 | 35.7 | 35.9 | 27.5 | 38 | 36.2 | 37.6 |
| 12:45:08 | 35.2 | 35.7 | 35.9 | 27.6 | 38 | 36.2 | 37.6 |
| 12:45:12 | 35.2 | 35.8 | 35.8 | 27.5 | 38 | 36.2 | 37.6 |
| 12:45:17 | 35.2 | 35.8 | 35.8 | 27.5 | 38 | 36.2 | 37.5 |
| 12:45:21 | 35.2 | 35.8 | 35.9 | 27.5 | 38 | 36.1 | 37.6 |
| 12:45:25 | 35.3 | 35.8 | 35.9 | 27.5 | 38 | 36.1 | 37.6 |
| 12:45:29 | 35.3 | 35.8 | 35.9 | 27.5 | 38 | 36.1 | 37.5 |
| 12:45:33 | 35.3 | 35.8 | 35.9 | 27.5 | 38 | 36.2 | 37.6 |
| 12:45:37 | 35.3 | 35.8 | 36 | 27.5 | 38 | 36.2 | 37.6 |
| 12:45:41 | 35.3 | 35.7 | 35.9 | 27.5 | 38 | 36.1 | 37.5 |
| 12:45:46 | 35.2 | 35.7 | 35.9 | 27.6 | 38 | 36.1 | 37.5 |
| 12:45:50 | 35.2 | 35.7 | 36 | 27.6 | 38 | 36.1 | 37.6 |
| 12:45:54 | 35.2 | 35.7 | 35.9 | 27.6 | 38 | 36.1 | 37.5 |
| 12:45:58 | 35.2 | 35.7 | 36 | 27.6 | 38 | 36.1 | 37.5 |
| 12:46:02 | 35.3 | 35.8 | 35.9 | 27.6 | 38 | 36.1 | 37.5 |
| 12:46:06 | 35.3 | 35.8 | 36 | 27.6 | 38 | 36.1 | 37.5 |
| 12:46:10 | 35.3 | 35.8 | 36 | 27.6 | 38 | 36.2 | 37.5 |
| 12:46:15 | 35.3 | 35.8 | 35.9 | 27.6 | 38 | 36.1 | 37.5 |
| 12:46:19 | 35.3 | 35.9 | 36 | 27.8 | 38 | 36.1 | 37.5 |
| 12:46:23 | 35.3 | 35.9 | 36 | 27.7 | 38 | 36.1 | 37.5 |
| 12:46:27 | 35.4 | 35.9 | 36 | 27.7 | 38 | 36.2 | 37.6 |
| 12:46:31 | 35.4 | 35.9 | 36 | 27.6 | 38 | 36.1 | 37.5 |
| 12:46:35 | 35.5 | 35.9 | 36 | 27.5 | 38 | 36.1 | 37.5 |
| 12:46:40 | 35.5 | 35.9 | 36 | 27.5 | 38 | 36.1 | 37.5 |
| 12:46:44 | 35.5 | 35.9 | 36 | 27.5 | 38 | 36.1 | 37.5 |
| 12:46:48 | 35.5 | 35.9 | 36 | 27.5 | 38 | 36.1 | 37.5 |
| 12:46:52 | 35.5 | 36 | 36 | 27.5 | 38 | 36.1 | 37.5 |
| 12:46:56 | 35.5 | 35.9 | 36 | 27.5 | 38 | 36.1 | 37.5 |
| 12:47:00 | 35.5 | 36 | 36 | 27.4 | 38 | 36.1 | 37.4 |
| 12:47:04 | 35.5 | 35.9 | 36 | 27.3 | 38 | 36.1 | 37.5 |
| 12:47:08 | 35.5 | 35.9 | 36 | 27.3 | 38 | 36.1 | 37.5 |
| 12:47:13 | 35.5 | 35.9 | 36 | 27.2 | 38 | 36.1 | 37.5 |
| 12:47:17 | 35.5 | 35.9 | 36.1 | 27.1 | 38 | 36.1 | 37.5 |
| 12:47:21 | 35.5 | 35.9 | 36.1 | 27.1 | 38 | 36.1 | 37.4 |
| 12:47:25 | 35.5 | 35.9 | 36 | 27.1 | 38 | 36.1 | 37.5 |
| 12:47:29 | 35.5 | 36 | 36.1 | 27.1 | 38 | 36.1 | 37.4 |
| 12:47:33 | 35.5 | 35.9 | 36 | 27.1 | 38 | 36.1 | 37.4 |
| 12:47:37 | 35.5 | 36 | 36.1 | 27 | 38 | 36 | 37.4 |
| 12:47:42 | 35.5 | 36 | 36 | 27 | 38 | 36.1 | 37.4 |
| 12:47:46 | 35.5 | 36 | 36.1 | 27 | 38 | 36 | 37.4 |
| 12:47:50 | 35.5 | 35.9 | 36 | 27 | 38 | 36.1 | 37.5 |
| 12:47:54 | 35.5 | 36 | 36 | 26.8 | 38 | 36 | 37.4 |
| 12:47:58 | 35.6 | 36 | 36.1 | 26.9 | 38 | 36 | 37.4 |
| 12:48:02 | 35.6 | 36 | 36.1 | 26.8 | 38 | 36.1 | 37.4 |
| 12:48:07 | 35.6 | 36 | 36.1 | 26.9 | 37.9 | 36 | 37.4 |
| 12:48:11 | 35.6 | 36 | 36.1 | 26.9 | 38 | 36 | 37.4 |
| 12:48:15 | 35.6 | 36 | 36.1 | 26.9 | 38 | 36 | 37.4 |
| 12:48:19 | 35.5 | 36 | 36 | 26.9 | 37.9 | 36 | 37.3 |
| 12:48:23 | 35.5 | 35.9 | 36.1 | 26.9 | 38 | 36 | 37.3 |
| 12:48:27 | 35.5 | 36 | 36.1 | 26.9 | 38 | 36 | 37.4 |
| 12:48:32 | 35.5 | 36 | 36.1 | 27.2 | 37.9 | 36 | 37.4 |
| 12:48:36 | 35.5 | 36 | 36.1 | 27.3 | 38 | 36.1 | 37.4 |
| 12:48:40 | 35.5 | 35.9 | 36.1 | 27.1 | 37.9 | 36 | 37.3 |
| 12:48:44 | 35.5 | 36 | 36.1 | 27.2 | 38 | 36 | 37.4 |
| 12:48:48 | 35.5 | 36 | 36.1 | 27.5 | 37.9 | 36 | 37.3 |
| 12:48:52 | 35.5 | 36 | 36.1 | 27.5 | 38 | 36 | 37.4 |
| 12:48:56 | 35.5 | 35.9 | 36.1 | 27.5 | 37.9 | 36 | 37.3 |
| 12:49:00 | 35.5 | 36 | 36.1 | 27.6 | 37.9 | 36 | 37.3 |
| 12:49:05 | 35.5 | 35.9 | 36.1 | 27.4 | 37.9 | 36 | 37.3 |
| 12:49:09 | 35.5 | 36 | 36.1 | 27.1 | 37.9 | 36 | 37.3 |
| 12:49:13 | 35.5 | 35.9 | 36.1 | 27 | 38 | 36 | 37.3 |
| 12:49:17 | 35.5 | 35.9 | 36.1 | 26.8 | 37.9 | 36 | 37.3 |
| 12:49:21 | 35.4 | 35.9 | 36.1 | 26.8 | 37.9 | 36 | 37.3 |
| 12:49:25 | 35.4 | 35.9 | 36.1 | 26.8 | 37.9 | 36 | 37.3 |
| 12:49:30 | 35.4 | 35.8 | 36.1 | 26.8 | 37.9 | 36 | 37.3 |
| 12:49:34 | 35.3 | 35.8 | 36.1 | 26.7 | 37.9 | 36 | 37.3 |
| 12:49:38 | 35.3 | 35.8 | 36.1 | 26.6 | 37.9 | 36 | 37.3 |
| 12:49:42 | 35.3 | 35.8 | 36.1 | 26.5 | 37.9 | 36 | 37.3 |
| 12:49:46 | 35.3 | 35.8 | 36.1 | 26.3 | 37.9 | 36 | 37.3 |

TABLE 1-continued

| | | | | | | | |
|---|---|---|---|---|---|---|---|
| 12:49:50 | 35.3 | 35.8 | 36.1 | 26.2 | 37.9 | 36 | 37.3 |
| 12:49:55 | 35.3 | 35.8 | 36.1 | 26.1 | 37.9 | 36 | 37.3 |
| 12:49:59 | 35.3 | 35.8 | 36.1 | 25.9 | 37.9 | 36 | 37.3 |
| 12:50:03 | 35.2 | 35.8 | 36.1 | 25.9 | 37.9 | 36 | 37.3 |
| 12:50:07 | 35.2 | 35.8 | 36.1 | 26 | 37.9 | 36 | 37.3 |
| 12:50:11 | 35.2 | 35.8 | 36.1 | 26 | 37.9 | 36 | 37.3 |
| 12:50:15 | 35.2 | 35.7 | 36.1 | 25.8 | 37.9 | 36 | 37.3 |
| 12:50:20 | 35.1 | 35.7 | 36.1 | 25.7 | 37.9 | 36 | 37.3 |
| 12:50:24 | 35.1 | 35.7 | 36.1 | 25.7 | 37.9 | 35.9 | 37.2 |
| 12:50:28 | 35.1 | 35.7 | 36.1 | 25.7 | 37.8 | 36 | 37.3 |
| 12:50:32 | 35.1 | 35.7 | 36.1 | 25.6 | 37.8 | 35.9 | 37.3 |
| 12:50:36 | 35.1 | 35.7 | 36.1 | 25.6 | 37.8 | 35.9 | 37.2 |
| 12:50:40 | 35.1 | 35.7 | 36.1 | 25.7 | 37.9 | 36 | 37.3 |
| 12:50:44 | 35 | 35.7 | 36.1 | 25.6 | 37.9 | 36 | 37.3 |
| 12:50:49 | 35 | 35.6 | 36.1 | 25.7 | 37.9 | 36 | 37.2 |
| 12:50:53 | 35 | 35.6 | 36 | 25.7 | 37.8 | 35.9 | 37.2 |
| 12:50:57 | 35 | 35.6 | 36 | 25.6 | 37.8 | 35.9 | 37.2 |
| 12:51:01 | 34.9 | 35.6 | 36 | 25.7 | 37.8 | 35.9 | 37.2 |
| 12:51:05 | 34.9 | 35.6 | 36 | 25.7 | 37.8 | 35.8 | 37.2 |
| 12:51:10 | 34.8 | 35.6 | 36 | 25.7 | 37.8 | 35.9 | 37.2 |
| 12:51:14 | 34.8 | 35.6 | 36 | 25.7 | 37.8 | 35.9 | 37.2 |
| 12:51:18 | 34.8 | 35.6 | 36.1 | 25.7 | 37.9 | 35.9 | 37.2 |
| 12:51:22 | 34.8 | 35.6 | 36 | 25.7 | 37.8 | 36 | 37.3 |
| 12:51:26 | 34.8 | 35.5 | 36 | 25.6 | 37.8 | 35.9 | 37.3 |
| 12:51:30 | 34.8 | 35.5 | 36 | 25.5 | 37.8 | 35.9 | 37.2 |
| 12:51:34 | 34.8 | 35.5 | 36 | 25.5 | 37.8 | 35.9 | 37.2 |
| 12:51:39 | 34.7 | 35.5 | 36 | 25.5 | 37.8 | 35.9 | 37.2 |
| 12:51:43 | 34.7 | 35.5 | 36 | 25.6 | 37.8 | 35.9 | 37.2 |
| 12:51:47 | 34.7 | 35.5 | 36 | 25.6 | 37.8 | 35.9 | 37.2 |
| 12:51:51 | 34.7 | 35.5 | 36 | 25.6 | 37.8 | 35.8 | 37.2 |
| 12:51:55 | 34.7 | 35.5 | 36 | 25.6 | 37.8 | 35.9 | 37.2 |
| 12:51:59 | 34.7 | 35.5 | 36 | 25.6 | 37.8 | 35.8 | 37.2 |
| 12:52:04 | 34.7 | 35.5 | 36 | 25.6 | 37.8 | 35.9 | 37.2 |
| 12:52:08 | 34.7 | 35.5 | 36 | 25.6 | 37.8 | 35.9 | 37.2 |
| 12:52:12 | 34.7 | 35.5 | 36 | 25.6 | 37.8 | 35.8 | 37.2 |
| 12:52:16 | 34.7 | 35.4 | 36 | 25.6 | 37.8 | 35.9 | 37.2 |
| 12:52:20 | 34.7 | 35.4 | 36 | 25.5 | 37.8 | 35.8 | 37.2 |
| 12:52:24 | 34.7 | 35.4 | 36 | 25.5 | 37.8 | 35.8 | 37.2 |
| 12:52:28 | 34.6 | 35.5 | 36 | 25.5 | 37.8 | 35.8 | 37.2 |
| 12:52:32 | 34.6 | 35.4 | 35.9 | 25.5 | 37.8 | 35.9 | 37.2 |
| 12:52:37 | 34.6 | 35.4 | 35.9 | 25.5 | 37.8 | 35.8 | 37.2 |
| 12:52:41 | 34.6 | 35.4 | 35.9 | 25.5 | 37.8 | 35.8 | 37.2 |
| 12:52:45 | 34.6 | 35.3 | 35.9 | 25.5 | 37.8 | 35.8 | 37.2 |
| 12:52:49 | 34.6 | 35.4 | 35.9 | 25.5 | 37.8 | 35.9 | 37.2 |
| 12:52:53 | 34.6 | 35.4 | 35.9 | 25.5 | 37.8 | 35.8 | 37.1 |
| 12:52:58 | 34.6 | 35.3 | 35.9 | 25.4 | 37.8 | 35.8 | 37.2 |
| 12:53:02 | 34.6 | 35.3 | 35.9 | 25.6 | 37.8 | 35.8 | 37.2 |
| 12:53:06 | 34.6 | 35.3 | 35.9 | 25.5 | 37.8 | 35.8 | 37.1 |
| 12:53:10 | 34.6 | 35.4 | 35.9 | 25.5 | 37.8 | 35.8 | 37.1 |
| 12:53:14 | 34.6 | 35.3 | 35.9 | 25.5 | 37.8 | 35.8 | 37.2 |
| 12:53:18 | 34.6 | 35.3 | 35.9 | 25.6 | 37.8 | 35.8 | 37.2 |
| 12:53:22 | 34.6 | 35.3 | 35.8 | 25.6 | 37.8 | 35.8 | 37.2 |
| 12:53:27 | 34.6 | 35.3 | 35.9 | 25.6 | 37.8 | 35.8 | 37.2 |
| 12:53:31 | 34.6 | 35.3 | 35.9 | 25.7 | 37.8 | 35.8 | 37.2 |
| 12:53:35 | 34.6 | 35.3 | 35.8 | 25.7 | 37.8 | 35.8 | 37.1 |
| 12:53:39 | 34.6 | 35.3 | 35.9 | 25.6 | 37.8 | 35.8 | 37.2 |
| 12:53:43 | 34.6 | 35.3 | 35.8 | 25.6 | 37.8 | 35.8 | 37.2 |
| 12:53:47 | 34.6 | 35.3 | 35.8 | 25.6 | 37.8 | 35.8 | 37.1 |
| 12:53:51 | 34.6 | 35.3 | 35.8 | 25.6 | 37.8 | 35.8 | 37.1 |
| 12:53:55 | 34.6 | 35.3 | 35.8 | 25.5 | 37.8 | 35.8 | 37.1 |
| 12:54:00 | 34.6 | 35.3 | 35.8 | 25.6 | 37.8 | 35.8 | 37.2 |
| 12:54:04 | 34.6 | 35.3 | 35.8 | 25.5 | 37.8 | 35.8 | 37.2 |
| 12:54:08 | 34.6 | 35.3 | 35.8 | 25.4 | 37.7 | 35.8 | 37.1 |
| 12:54:12 | 34.6 | 35.3 | 35.8 | 25.5 | 37.8 | 35.8 | 37.1 |
| 12:54:16 | 34.6 | 35.3 | 35.8 | 25.4 | 37.8 | 35.8 | 37.1 |
| 12:54:20 | 34.6 | 35.3 | 35.8 | 25.4 | 37.7 | 35.8 | 37.1 |
| 12:54:24 | 34.6 | 35.3 | 35.8 | 25.4 | 37.8 | 35.8 | 37.1 |
| 12:54:29 | 34.6 | 35.3 | 35.8 | 25.5 | 37.8 | 35.8 | 37.1 |
| 12:54:33 | 34.6 | 35.4 | 35.7 | 25.5 | 37.7 | 35.8 | 37.1 |
| 12:54:37 | 34.7 | 35.3 | 35.8 | 25.6 | 37.7 | 35.8 | 37.1 |
| 12:54:41 | 34.6 | 35.3 | 35.8 | 26 | 37.7 | 35.8 | 37.1 |

| TIME | 1:VASC | 1:AIRWAY | 1:EAR | MINUTES | HEAD-M | COOLING | NOSE |
|---|---|---|---|---|---|---|---|
| 12:26:52 | 37.7 | 30.3 | 32.3 | 0 | 38.1 | 0 | 26.6 |
| 12:26:56 | 37.7 | 30 | 32.3 | 0.066667 | 38.1 | 0 | 27.9 |
| 12:27:01 | 37.6 | 29.6 | 32.2 | 0.15 | 38.1 | 0 | 27 |
| 12:27:05 | 37.6 | 29.1 | 32.2 | 0.216667 | 38.1 | 0 | 15 |
| 12:27:09 | 37.6 | 28.9 | 32.3 | 0.283333 | 38.1 | 0 | 14 |
| 12:27:13 | 37.5 | 29.3 | 32.3 | 0.35 | 38.06667 | −0.03333 | 12.8 |

TABLE 1-continued

| | | | | | | | |
|---|---|---|---|---|---|---|---|
| 12:27:17 | 37.3 | 29.8 | 32.3 | 0.416667 | 38 | −0.1 | 12.9 |
| 12:27:21 | 37.3 | 30.1 | 32.3 | 0.483333 | 37.96667 | −0.13333 | 12.6 |
| 12:27:26 | 37.1 | 29.7 | 32.3 | 0.566667 | 37.9 | −0.2 | 11.8 |
| 12:27:30 | 37.1 | 29.4 | 32.3 | 0.633333 | 37.9 | −0.2 | 12 |
| 12:27:34 | 37 | 29 | 32.3 | 0.7 | 37.83333 | −0.26667 | 11.7 |
| 12:27:38 | 36.9 | 28.9 | 32.3 | 0.766667 | 37.8 | −0.3 | 12 |
| 12:27:42 | 36.8 | 29.2 | 32.3 | 0.833333 | 37.73333 | −0.36667 | 11.5 |
| 12:27:46 | 36.7 | 29.7 | 32.3 | 0.9 | 37.7 | −0.4 | 11.7 |
| 12:27:50 | 36.7 | 29.7 | 32.3 | 0.966667 | 37.63333 | −0.46667 | 11.8 |
| 12:27:55 | 36.7 | 29.6 | 32.3 | 1.05 | 37.6 | −0.5 | 11.7 |
| 12:27:59 | 36.7 | 29.2 | 32.3 | 1.116667 | 37.53333 | −0.56667 | 11.4 |
| 12:28:03 | 36.6 | 28.8 | 32.2 | 1.183333 | 37.53333 | −0.56667 | 11.2 |
| 12:28:07 | 36.6 | 28.8 | 32.3 | 1.25 | 37.5 | −0.6 | 11 |
| 12:28:11 | 36.5 | 29 | 32.3 | 1.316667 | 37.43333 | −0.66667 | 10.8 |
| 12:28:15 | 36.6 | 29.5 | 32.3 | 1.383333 | 37.43333 | −0.66667 | 10.8 |
| 12:28:20 | 36.7 | 29.8 | 32.3 | 1.466667 | 37.43333 | −0.66667 | 11 |
| 12:28:24 | 36.8 | 29.6 | 32.3 | 1.533333 | 37.36667 | −0.73333 | 11.2 |
| 12:28:28 | 36.9 | 29.3 | 32.3 | 1.6 | 37.26667 | −0.83333 | 11.1 |
| 12:28:32 | 36.8 | 28.8 | 32.3 | 1.666667 | 37.33333 | −0.76667 | 11.1 |
| 12:28:36 | 36.8 | 28.7 | 32.3 | 1.733333 | 37.26667 | −0.83333 | 11.2 |
| 12:28:40 | 36.8 | 29 | 32.3 | 1.8 | 37.26667 | −0.83333 | 11.1 |
| 12:28:44 | 36.7 | 29.5 | 32.3 | 1.866667 | 37.23333 | −0.86667 | 11 |
| 12:28:49 | 36.8 | 29.9 | 32.3 | 1.95 | 37.2 | −0.9 | 11.2 |
| 12:28:53 | 37 | 29.6 | 32.3 | 2.016667 | 37.13333 | −0.96667 | 11.2 |
| 12:28:57 | 36.8 | 29.2 | 32.3 | 2.083333 | 37.1 | −1 | 11.1 |
| 12:29:01 | 36.8 | 28.8 | 32.3 | 2.15 | 37.1 | −1 | 11.2 |
| 12:29:05 | 36.8 | 29.2 | 32.3 | 2.216667 | 37.1 | −1 | 11.2 |
| 12:29:09 | 36.8 | 29.2 | 32.3 | 2.283333 | 37.03333 | −1.06667 | 11.3 |
| 12:29:13 | 36.6 | 29.6 | 32.3 | 2.35 | 37.03333 | −1.06667 | 10.8 |
| 12:29:18 | 36.5 | 29.2 | 32.2 | 2.433333 | 37.06667 | −1.03333 | 10.9 |
| 12:29:22 | 36.7 | 28.7 | 32.3 | 2.5 | 37.03333 | −1.06667 | 10.5 |
| 12:29:26 | 36.5 | 28.5 | 32.3 | 2.566667 | 37.06667 | −1.03333 | 10.8 |
| 12:29:30 | 36.6 | 28.6 | 32.3 | 2.633333 | 37 | −1.1 | 10.8 |
| 12:29:34 | 36.5 | 29 | 32.3 | 2.7 | 37 | −1.1 | 11 |
| 12:29:38 | 36.5 | 29.3 | 32.3 | 2.766667 | 36.96667 | −1.13333 | 10.9 |
| 12:29:43 | 36.4 | 29.5 | 32.3 | 2.85 | 36.96667 | −1.13333 | 10.9 |
| 12:29:47 | 36.5 | 29.2 | 32.3 | 2.916667 | 36.9 | −1.2 | 10.8 |
| 12:29:51 | 36.7 | 28.8 | 32.3 | 2.983333 | 36.9 | −1.2 | 10.9 |
| 12:29:55 | 36.7 | 28.5 | 32.3 | 3.05 | 36.9 | −1.2 | 10.8 |
| 12:29:59 | 36.7 | 28.5 | 32.3 | 3.116667 | 36.83333 | −1.26667 | 10.8 |
| 12:30:03 | 36.7 | 29 | 32.3 | 3.183333 | 36.86667 | −1.23333 | 11.1 |
| 12:30:07 | 36.7 | 29.5 | 32.3 | 3.25 | 36.8 | −1.3 | 10.9 |
| 12:30:12 | 36.7 | 29.4 | 32.3 | 3.333333 | 36.73333 | −1.36667 | 10.9 |
| 12:30:16 | 36.7 | 29.1 | 32.3 | 3.4 | 36.76667 | −1.33333 | 11 |
| 12:30:20 | 36.7 | 28.7 | 32.3 | 3.466667 | 36.73333 | −1.36667 | 11.1 |
| 12:30:24 | 36.7 | 28.5 | 32.3 | 3.533333 | 36.7 | −1.4 | 10.9 |
| 12:30:28 | 36.7 | 28.9 | 32.3 | 3.6 | 36.66667 | −1.43333 | 11 |
| 12:30:32 | 36.6 | 29.4 | 32.3 | 3.666667 | 36.66667 | −1.43333 | 11.1 |
| 2:30:36 | 36.7 | 29.5 | 32.3 | 3.733333 | 36.66667 | −1.43333 | 11.1 |
| 12:30:41 | 36.7 | 29.1 | 32.3 | 3.816667 | 36.63333 | −1.46667 | 10.8 |
| 12:30:45 | 36.7 | 28.7 | 32.3 | 3.883333 | 36.56667 | −1.53333 | 11 |
| 12:30:49 | 36.7 | 28.4 | 32.3 | 3.95 | 36.56667 | −1.53333 | 11.1 |
| 12:30:53 | 36.6 | 28.6 | 32.3 | 4.016667 | 36.56667 | −1.53333 | 11 |
| 12:30:57 | 36.6 | 29.2 | 32.3 | 4.083333 | 36.56667 | −1.53333 | 11 |
| 12:31:01 | 36.7 | 29.4 | 32.2 | 4.15 | 36.43333 | −1.66667 | 11 |
| 12:31:06 | 36.7 | 29.2 | 32.3 | 4.233333 | 36.43333 | −1.66667 | 11 |
| 12:31:10 | 36.7 | 28.7 | 32.2 | 4.3 | 36.46667 | −1.63333 | 10.8 |
| 12:31:14 | 36.6 | 28.3 | 32.3 | 4.366667 | 36.46667 | −1.63333 | 11 |
| 12:31:18 | 36.6 | 28.3 | 32.3 | 4.433333 | 36.46667 | −1.63333 | 11 |
| 12:31:22 | 36.7 | 28.5 | 32.3 | 4.5 | 36.4 | −1.7 | 11.1 |
| 12:31:26 | 36.7 | 29.1 | 32.2 | 4.566667 | 36.4 | −1.7 | 11 |
| 12:31:30 | 36.7 | 29.2 | 32.3 | 4.633333 | 36.36667 | −1.73333 | 11.3 |
| 12:31:35 | 36.6 | 28.9 | 32.2 | 4.716667 | 36.3 | −1.8 | 11.3 |
| 12:31:39 | 36.7 | 28.5 | 32.2 | 4.783333 | 36.3 | −1.8 | 11.2 |
| 12:31:43 | 36.7 | 28.2 | 32.2 | 4.85 | 36.3 | −1.8 | 11.2 |
| 12:31:47 | 36.6 | 28.2 | 32.3 | 4.916667 | 36.3 | −1.8 | 11.2 |
| 12:31:51 | 36.6 | 28.7 | 32.3 | 4.983333 | 36.3 | −1.8 | 11 |
| 12:31:55 | 36.6 | 29.1 | 32.2 | 5.05 | 36.26667 | −1.83333 | 10.9 |
| 12:31:59 | 36.5 | 29.1 | 32.2 | 5.116667 | 36.3 | −1.8 | 11 |
| 12:32:04 | 36.6 | 28.7 | 32.2 | 5.2 | 36.2 | −1.9 | 10.9 |
| 12:32:08 | 36.6 | 28.2 | 32.2 | 5.266667 | 36.2 | −1.9 | 11 |
| 12:32:12 | 36.6 | 28 | 32.2 | 5.333333 | 36.2 | −1.9 | 10.7 |
| 12:32:16 | 36.6 | 28.2 | 32.2 | 5.4 | 36.16667 | −1.93333 | 11.3 |
| 12:32:20 | 36.6 | 28.7 | 32.2 | 5.466667 | 36.16667 | −1.93333 | 11.1 |
| 12:32:24 | 36.6 | 29 | 32.2 | 5.533333 | 36.1 | −2 | 10.8 |
| 12:32:29 | 36.6 | 28.7 | 32.2 | 5.616667 | 36.06667 | −2.03333 | 10.8 |
| 12:32:33 | 36.5 | 28.3 | 32.2 | 5.683333 | 36.06667 | −2.03333 | 10.7 |
| 12:32:37 | 36.6 | 28 | 32.2 | 5.75 | 36.06667 | −2.03333 | 10.8 |
| 12:32:41 | 36.6 | 28 | 32.2 | 5.816667 | 36.03333 | −2.06667 | 10.8 |
| 12:32:45 | 36.6 | 28.2 | 32.2 | 5.883333 | 36.03333 | −2.06667 | 11 |

TABLE 1-continued

| | | | | | | | |
|---|---|---|---|---|---|---|---|
| 12:32:49 | 36.6 | 28.7 | 32.2 | 5.95 | 36 | −2.1 | 11 |
| 12:32:53 | 36.6 | 28.9 | 32.2 | 6.016667 | 35.96667 | −2.13333 | 11 |
| 12:32:58 | 36.7 | 28.7 | 32.2 | 6.1 | 35.96667 | −2.13333 | 10.8 |
| 12:33:02 | 36.6 | 28.2 | 32.2 | 6.166667 | 35.93333 | −2.16667 | 10.9 |
| 12:33:06 | 36.6 | 28.1 | 32.2 | 6.233333 | 35.93333 | −2.16667 | 10.8 |
| 12:33:10 | 36.5 | 28.5 | 32.2 | 6.3 | 35.93333 | −2.16667 | 10.8 |
| 12:33:14 | 36.6 | 29 | 32.2 | 6.366667 | 35.93333 | −2.16667 | 10.6 |
| 12:33:18 | 36.6 | 29 | 32.2 | 6.433333 | 35.86667 | −2.23333 | 10.9 |
| 12:33:23 | 36.7 | 28.8 | 32.2 | 6.516667 | 35.9 | −2.2 | 10.8 |
| 12:33:27 | 36.7 | 28.4 | 32.2 | 6.583333 | 35.9 | −2.2 | 10.8 |
| 12:33:31 | 36.7 | 28 | 32.2 | 6.65 | 35.86667 | −2.23333 | 10.8 |
| 12:33:35 | 36.6 | 28.1 | 32.2 | 6.716667 | 35.86667 | −2.23333 | 10.8 |
| 12:33:39 | 36.6 | 28.7 | 32.2 | 6.783333 | 35.83333 | −2.26667 | 10.7 |
| 12:33:43 | 36.6 | 29 | 32.2 | 6.85 | 35.86667 | −2.23333 | 11.1 |
| 12:33:47 | 36.6 | 28.7 | 32.2 | 6.916667 | 35.86667 | −2.23333 | 10.8 |
| 12:33:52 | 36.6 | 28.4 | 32.2 | 7 | 35.86667 | −2.23333 | 10.6 |
| 12:33:56 | 36.6 | 28.1 | 32.2 | 7.066667 | 35.86667 | −2.23333 | 10.6 |
| 12:34:00 | 36.6 | 28 | 32.2 | 7.133333 | 35.9 | −2.2 | 10.7 |
| 12:34:04 | 36.6 | 28.2 | 32.2 | 7.2 | 35.9 | −2.2 | 10.7 |
| 12:34:08 | 36.5 | 28.6 | 32.2 | 7.266667 | 35.86667 | −2.23333 | 10.7 |
| 12:34:12 | 36.6 | 29 | 32.2 | 7.333333 | 35.86667 | −2.23333 | 10.7 |
| 12:34:16 | 36.5 | 28.8 | 32.2 | 7.4 | 35.86667 | −2.23333 | 10.6 |
| 12:34:21 | 36.6 | 28.5 | 32.2 | 7.483333 | 35.83333 | −2.26667 | 10.6 |
| 12:34:25 | 36.5 | 28.1 | 32.2 | 7.55 | 35.83333 | −2.26667 | 10.4 |
| 12:34:29 | 36.5 | 28 | 32.2 | 7.616667 | 35.83333 | −2.26667 | 10.6 |
| 12:34:33 | 36.5 | 28.2 | 32.2 | 7.683333 | 35.76667 | −2.33333 | 10.6 |
| 12:34:37 | 36.4 | 28.6 | 32.2 | 7.75 | 35.76667 | −2.33333 | 10.5 |
| 12:34:41 | 36.5 | 28.9 | 32.2 | 7.816667 | 35.76667 | −2.33333 | 10.4 |
| 12:34:46 | 36.5 | 28.7 | 32.2 | 7.9 | 35.76667 | −2.33333 | 10.5 |
| 12:34:50 | 36.5 | 28.4 | 32.2 | 7.966667 | 35.7 | −2.4 | 10.7 |
| 12:34:54 | 36.4 | 28.2 | 32.2 | 8.033333 | 35.7 | −2.4 | 10.5 |
| 12:34:58 | 36.3 | 27.9 | 32.2 | 8.1 | 35.7 | −2.4 | 10.3 |
| 12:35:02 | 36.3 | 27.9 | 32.2 | 8.166667 | 35.66667 | −2.43333 | 10.3 |
| 12:35:06 | 36.3 | 28.2 | 32.2 | 8.233333 | 35.7 | −2.4 | 10.3 |
| 12:35:11 | 36.3 | 28.6 | 32.2 | 8.316667 | 35.63333 | −2.46667 | 10.3 |
| 12:35:15 | 36.3 | 28.6 | 32.1 | 8.383333 | 35.6 | −2.5 | 10.2 |
| 12:35:19 | 36.4 | 28.3 | 32.2 | 8.45 | 35.6 | −2.5 | 10.3 |
| 12:35:23 | 36.3 | 28 | 32.2 | 8.516667 | 35.5 | −2.6 | 10.3 |
| 12:35:27 | 36.3 | 27.8 | 32.1 | 8.583333 | 35.5 | −2.6 | 10.2 |
| 12:35:31 | 36.3 | 27.8 | 32.1 | 8.65 | 35.5 | −2.6 | 10.2 |
| 12:35:35 | 36.3 | 28.1 | 32.1 | 8.716667 | 35.53333 | −2.56667 | 10.1 |
| 12:35:40 | 36.3 | 28.5 | 32.2 | 8.8 | 35.53333 | −2.56667 | 10.1 |
| 12:35:44 | 36.3 | 28.6 | 32.2 | 8.866667 | 35.53333 | −2.56667 | 9.9 |
| 12:35:48 | 36.4 | 28.5 | 32.2 | 8.933333 | 35.5 | −2.6 | 10 |
| 12:35:52 | 36.5 | 28.2 | 32.2 | 9 | 35.46667 | −2.63333 | 10 |
| 12:35:56 | 36.4 | 28 | 32.2 | 9.066667 | 35.4 | −2.7 | 9.9 |
| 12:36:00 | 36.4 | 27.7 | 32.1 | 9.133333 | 35.46667 | −2.63333 | 9.7 |
| 12:36:04 | 36.5 | 28.1 | 32.2 | 9.2 | 35.4 | −2.7 | 9.9 |
| 12:36:09 | 36.4 | 28.4 | 32.2 | 9.283333 | 35.4 | −2.7 | 9.8 |
| 12:36:13 | 36.3 | 28.6 | 32.1 | 9.35 | 35.4 | −2.7 | 9.8 |
| 12:36:17 | 36.4 | 28.6 | 32.1 | 9.416667 | 35.36667 | −2.73333 | 9.8 |
| 12:36:21 | 36.4 | 28.3 | 32.2 | 9.483333 | 35.36667 | −2.73333 | 9.7 |
| 12:36:25 | 36.4 | 28 | 32.1 | 9.55 | 35.36667 | −2.73333 | 9.8 |
| 12:36:29 | 36.4 | 27.8 | 32.2 | 9.616667 | 35.33333 | −2.76667 | 9.7 |
| 12:36:34 | 36.4 | 27.8 | 32.1 | 9.7 | 35.33333 | −2.76667 | 9.6 |
| 12:36:38 | 36.3 | 27.9 | 32.1 | 9.766667 | 35.33333 | −2.76667 | 9.7 |
| 12:36:42 | 36.4 | 28.3 | 32.1 | 9.833333 | 35.26667 | −2.83333 | 9.7 |
| 12:36:46 | 36.3 | 28.5 | 32.1 | 9.9 | 35.26667 | −2.83333 | 9.6 |
| 12:36:50 | 36.3 | 28.3 | 32.1 | 9.966667 | 35.23333 | −2.86667 | 9.5 |
| 12:36:54 | 36.3 | 28.1 | 32.1 | 10.03333 | 35.23333 | −2.86667 | 9.6 |
| 12:36:58 | 36.3 | 27.8 | 32.1 | 10.1 | 35.2 | −2.9 | 9.6 |
| 12:37:03 | 36.4 | 27.6 | 32.1 | 10.18333 | 35.23333 | −2.86667 | 9.5 |
| 12:37:07 | 36.3 | 27.8 | 32.1 | 10.25 | 35.2 | −2.9 | 9.5 |
| 12:37:11 | 36.3 | 28.2 | 32.1 | 10.31667 | 35.2 | −2.9 | 9.6 |
| 12:37:15 | 36.3 | 28.2 | 32.1 | 10.38333 | 35.16667 | −2.93333 | 9.6 |
| 12:37:19 | 36.3 | 28.1 | 32.1 | 10.45 | 35.2 | −2.9 | 9.4 |
| 12:37:23 | 36.3 | 27.8 | 32.1 | 10.51667 | 35.16667 | −2.93333 | 9.6 |
| 12:37:28 | 36.3 | 27.6 | 32.1 | 10.6 | 35.16667 | −2.93333 | 9.6 |
| 12:37:32 | 36.3 | 27.7 | 32.1 | 10.66667 | 35.16667 | −2.93333 | 9.3 |
| 12:37:36 | 36.2 | 28.1 | 32.1 | 10.73333 | 35.06667 | −3.03333 | 9.4 |
| 12:37:40 | 36.2 | 28.3 | 32.1 | 10.8 | 35.1 | −3 | 9.5 |
| 12:37:44 | 36.2 | 28.3 | 32.1 | 10.86667 | 35.1 | −3 | 9.4 |
| 12:37:48 | 36.2 | 28 | 32.1 | 10.93333 | 35.06667 | −3.03333 | 9.2 |
| 12:37:53 | 36.2 | 27.7 | 32.1 | 11.01667 | 35.06667 | −3.03333 | 9.3 |
| 12:37:57 | 36.2 | 27.5 | 32.1 | 11.08333 | 35.06667 | −3.03333 | 9.3 |
| 12:38:01 | 36.1 | 27.6 | 32.1 | 11.15 | 35.06667 | −3.03333 | 9.3 |
| 12:38:05 | 36.1 | 28 | 32.1 | 11.21667 | 35.06667 | −3.03333 | 9.3 |
| 12:38:09 | 36 | 28.2 | 32.1 | 11.28333 | 35.03333 | −3.06667 | 9.3 |
| 12:38:13 | 36.1 | 28.1 | 32.1 | 11.35 | 35.03333 | −3.06667 | 9.3 |
| 12:38:17 | 36 | 27.8 | 32.1 | 11.41667 | 35 | −3.1 | 9.3 |

TABLE 1-continued

| | | | | | | | |
|---|---|---|---|---|---|---|---|
| 12:38:21 | 36.1 | 27.5 | 32.1 | 11.48333 | 35.03333 | −3.06667 | 9.3 |
| 12:38:25 | 36.1 | 27.5 | 32.1 | 11.55 | 35.03333 | −3.06667 | 9.3 |
| 12:38:30 | 36 | 27.7 | 32.1 | 11.63333 | 34.96667 | −3.13333 | 9.3 |
| 12:38:34 | 36 | 28.1 | 32.1 | 11.7 | 35 | −3.1 | 9.3 |
| 12:38:38 | 36.1 | 28.1 | 32.1 | 11.76667 | 34.96667 | −3.13333 | 9.3 |
| 12:38:42 | 36.1 | 27.8 | 32.1 | 11.83333 | 34.93333 | −3.16667 | 9.4 |
| 12:38:46 | 36.1 | 27.5 | 32.1 | 11.9 | 34.96667 | −3.13333 | 9.5 |
| 12:38:50 | 36.2 | 27.3 | 32.1 | 11.96667 | 34.96667 | −3.13333 | 9.4 |
| 12:38:55 | 36 | 27.5 | 32.1 | 12.05 | 34.96667 | −3.13333 | 9.4 |
| 12:38:59 | 36.1 | 27.8 | 32.1 | 12.11667 | 34.93333 | −3.16667 | 9.5 |
| 12:39:03 | 36.1 | 28.2 | 32.1 | 12.18333 | 34.96667 | −3.13333 | 9.5 |
| 12:39:07 | 36.1 | 28.1 | 32.1 | 12.25 | 34.9 | −3.2 | 9.4 |
| 12:39:11 | 36.1 | 27.8 | 32.1 | 12.31667 | 34.93333 | −3.16667 | 9.4 |
| 12:39:15 | 36.1 | 27.5 | 32.1 | 12.38333 | 34.93333 | −3.16667 | 9.5 |
| 12:39:19 | 36.1 | 27.3 | 32.1 | 12.45 | 34.93333 | −3.16667 | 9.6 |
| 12:39:24 | 36 | 27.6 | 32.1 | 12.53333 | 34.9 | −3.2 | 9.4 |
| 12:39:28 | 36.1 | 28 | 32.1 | 12.6 | 34.93333 | −3.16667 | 9.3 |
| 12:39:32 | 36 | 28.2 | 32 | 12.66667 | 34.9 | −3.2 | 9.5 |
| 12:39:36 | 36 | 28.1 | 32.1 | 12.73333 | 34.93333 | −3.16667 | 9.5 |
| 12:39:40 | 36 | 27.8 | 32.1 | 12.8 | 34.86667 | −3.23333 | 9.3 |
| 12:39:44 | 36.1 | 27.5 | 32 | 12.86667 | 34.86667 | −3.23333 | 9.3 |
| 12:39:49 | 36.1 | 27.3 | 32 | 12.95 | 34.86667 | −3.23333 | 9.3 |
| 12:39:53 | 36 | 27.6 | 32 | 13.01667 | 34.83333 | −3.26667 | 9.3 |
| 12:39:57 | 36.1 | 28 | 32 | 13.08333 | 34.83333 | −3.26667 | 9.2 |
| 12:40:01 | 36 | 28.1 | 32 | 13.15 | 34.83333 | −3.26667 | 9.2 |
| 12:40:05 | 36 | 27.8 | 32 | 13.21667 | 34.83333 | −3.26667 | 9.2 |
| 12:40:09 | 36.1 | 27.5 | 32 | 13.28333 | 34.83333 | −3.26667 | 9.2 |
| 12:40:13 | 36.2 | 27.3 | 32.1 | 13.35 | 34.83333 | −3.26667 | 9.2 |
| 12:40:18 | 36 | 27.3 | 32 | 13.43333 | 34.83333 | −3.26667 | 9.1 |
| 12:40:22 | 36 | 27.8 | 32 | 13.5 | 34.83333 | −3.26667 | 9.2 |
| 12:40:26 | 36 | 28.1 | 32 | 13.56667 | 34.83333 | −3.26667 | 9.1 |
| 12:40:30 | 36 | 27.9 | 32 | 13.63333 | 34.83333 | −3.26667 | 9.1 |
| 12:40:34 | 36 | 27.7 | 32 | 13.7 | 34.83333 | −3.26667 | 9.1 |
| 12:40:38 | 36 | 27.3 | 32 | 13.76667 | 34.8 | −3.3 | 9.2 |
| 12:40:42 | 36 | 27.2 | 32 | 13.83333 | 34.83333 | −3.26667 | 9 |
| 12:40:47 | 36 | 27.5 | 32 | 13.91667 | 34.8 | −3.3 | 8.9 |
| 12:40:51 | 35.9 | 27.9 | 32 | 13.98333 | 34.83333 | −3.26667 | 8.8 |
| 12:40:55 | 35.9 | 28 | 32 | 14.05 | 34.8 | −3.3 | 8.9 |
| 12:40:59 | 35.9 | 27.6 | 32 | 14.11667 | 34.76667 | −3.33333 | 8.9 |
| 12:41:03 | 36 | 27.3 | 32 | 14.18333 | 34.76667 | −3.33333 | 8.8 |
| 12:41:07 | 35.9 | 27.1 | 32 | 14.25 | 34.76667 | −3.33333 | 8.8 |
| 12:41:12 | 36 | 27.4 | 32 | 14.33333 | 34.8 | −3.3 | 8.8 |
| 12:41:16 | 36 | 28 | 32 | 14.4 | 34.76667 | −3.33333 | 8.8 |
| 12:41:20 | 35.9 | 27.7 | 32 | 14.46667 | 34.76667 | −3.33333 | 8.8 |
| 12:41:24 | 36 | 27.4 | 32 | 14.53333 | 34.76667 | −3.33333 | 8.7 |
| 12:41:28 | 36 | 27.1 | 32 | 14.6 | 34.73333 | −3.36667 | 8.8 |
| 12:41:32 | 35.8 | 27.2 | 32 | 14.66667 | 34.76667 | −3.33333 | 8.8 |
| 12:41:36 | 35.8 | 27.7 | 32 | 14.73333 | 34.7 | −3.4 | 8.9 |
| 12:41:41 | 35.9 | 27.9 | 32 | 14.81667 | 34.76667 | −3.33333 | 8.8 |
| 12:41:45 | 35.9 | 27.7 | 32 | 14.88333 | 34.7 | −3.4 | 8.8 |
| 12:41:49 | 35.8 | 27.4 | 32 | 14.95 | 34.73333 | −3.36667 | 8.8 |
| 12:41:53 | 35.9 | 27.1 | 32 | 15.01667 | 34.73333 | −3.36667 | 8.8 |
| 12:41:57 | 35.8 | 27.1 | 32 | 15.08333 | 34.76667 | −3.33333 | 9 |
| 12:42:01 | 35.8 | 27.5 | 32 | 15.15 | 34.8 | −3.3 | 8.8 |
| 12:42:05 | 35.7 | 27.8 | 32 | 15.21667 | 34.8 | −3.3 | 8.8 |
| 12:42:10 | 35.9 | 27.6 | 32 | 15.3 | 34.83333 | −3.26667 | 8.7 |
| 12:42:14 | 35.8 | 27.3 | 32 | 15.36667 | 34.8 | −3.3 | 8.8 |
| 12:42:18 | 35.8 | 27 | 32 | 15.43333 | 34.9 | −3.2 | 8.8 |
| 12:42:22 | 35.8 | 27.1 | 32 | 15.5 | 34.9 | −3.2 | 8.8 |
| 12:42:26 | 35.8 | 27.3 | 32 | 15.56667 | 34.9 | −3.2 | 8.6 |
| 12:42:30 | 35.8 | 27.7 | 32 | 15.63333 | 34.9 | −3.2 | 8.5 |
| 12:42:35 | 35.9 | 27.7 | 32 | 15.71667 | 34.96667 | −3.13333 | 8.6 |
| 12:42:39 | 35.9 | 27.5 | 32 | 15.78333 | 34.93333 | −3.16667 | 8.5 |
| 12:42:43 | 35.8 | 27.1 | 32 | 15.85 | 34.96667 | −3.13333 | 8.5 |
| 12:42:47 | 35.7 | 27 | 32 | 15.91667 | 34.93333 | −3.16667 | 8.5 |
| 12:42:51 | 35.8 | 27.2 | 32 | 15.98333 | 34.93333 | −3.16667 | 9.2 |
| 12:42:55 | 35.8 | 27.6 | 32 | 16.05 | 34.93333 | −3.16667 | 9.1 |
| 12:42:59 | 35.8 | 27.7 | 32 | 16.11667 | 35 | −3.1 | 9.1 |
| 12:43:04 | 35.9 | 27.5 | 32 | 16.2 | 35 | −3.1 | 8.9 |
| 12:43:08 | 35.8 | 27.2 | 31.9 | 16.26667 | 34.93333 | −3.16667 | 8.9 |
| 12:43:12 | 35.7 | 26.8 | 31.9 | 16.33333 | 34.96667 | −3.13333 | 8.9 |
| 12:43:16 | 35.6 | 27 | 32 | 16.4 | 34.96667 | −3.13333 | 8.9 |
| 12:43:20 | 35.7 | 27.4 | 32 | 16.46667 | 35.03333 | −3.06667 | 8.7 |
| 12:43:24 | 35.7 | 27.8 | 31.9 | 16.53333 | 35.1 | −3 | 8.7 |
| 12:43:28 | 35.8 | 27.5 | 31.9 | 16.6 | 35.16667 | −2.93333 | 8.7 |
| 12:43:33 | 35.8 | 27.3 | 31.9 | 16.68333 | 35.2 | −2.9 | 8.8 |
| 12:43:37 | 35.8 | 27.1 | 31.9 | 16.75 | 35.23333 | −2.86667 | 8.7 |
| 12:43:41 | 35.7 | 26.8 | 31.9 | 16.81667 | 35.3 | −2.8 | 8.7 |
| 12:43:45 | 35.7 | 27.1 | 31.9 | 16.88333 | 35.33333 | −2.76667 | 8.7 |
| 12:43:49 | 35.8 | 27.5 | 31.9 | 16.95 | 35.33333 | −2.76667 | 8.8 |

TABLE 1-continued

| | | | | | | | |
|---|---|---|---|---|---|---|---|
| 12:43:53 | 35.7 | 27.6 | 31.9 | 17.01667 | 35.33333 | −2.76667 | 8.7 |
| 12:43:58 | 35.6 | 27.5 | 31.9 | 17.1 | 35.26667 | −2.83333 | 8.9 |
| 12:44:02 | 35.8 | 27.1 | 32 | 17.16667 | 35.36667 | −2.73333 | 8.8 |
| 12:44:06 | 35.7 | 26.9 | 32 | 17.23333 | 35.4 | −2.7 | 8.8 |
| 12:44:10 | 35.6 | 26.8 | 31.9 | 17.3 | 35.4 | −2.7 | 8.8 |
| 12:44:14 | 35.5 | 27.2 | 31.9 | 17.36667 | 35.43333 | −2.66667 | 8.7 |
| 12:44:18 | 35.6 | 27.5 | 31.9 | 17.43333 | 35.46667 | −2.63333 | 8.7 |
| 12:44:22 | 35.8 | 27.6 | 31.9 | 17.5 | 35.46667 | −2.63333 | 8.7 |
| 12:44:27 | 35.8 | 27.3 | 31.9 | 17.58333 | 35.53333 | −2.56667 | 8.6 |
| 12:44:31 | 35.8 | 27.1 | 31.9 | 17.65 | 35.5 | −2.6 | 8.6 |
| 12:44:35 | 35.8 | 26.8 | 31.9 | 17.71667 | 35.53333 | −2.56667 | 8.6 |
| 12:44:39 | 35.7 | 26.8 | 31.8 | 17.78333 | 35.5 | −2.6 | 8.4 |
| 12:44:43 | 35.6 | 27.2 | 31.8 | 17.85 | 35.53333 | −2.56667 | 8.5 |
| 12:44:47 | 35.7 | 27.5 | 31.9 | 17.91667 | 35.53333 | −2.56667 | 8.5 |
| 12:44:52 | 35.8 | 27.5 | 31.8 | 18 | 35.5 | −2.6 | 8.6 |
| 12:44:56 | 35.7 | 27.1 | 31.8 | 18.06667 | 35.53333 | −2.56667 | 8.8 |
| 12:45:00 | 35.5 | 26.8 | 31.9 | 18.13333 | 35.53333 | −2.56667 | 8.8 |
| 12:45:04 | 35.6 | 27 | 31.8 | 18.2 | 35.6 | −2.5 | 8.7 |
| 12:45:08 | 35.7 | 27.4 | 31.8 | 18.26667 | 35.6 | −2.5 | 8.5 |
| 12:45:12 | 35.7 | 27.5 | 31.8 | 18.33333 | 35.6 | −2.5 | 8.5 |
| 12:45:17 | 35.7 | 27.3 | 31.8 | 18.41667 | 35.6 | −2.5 | 8.5 |
| 12:45:21 | 35.7 | 27 | 31.8 | 18.48333 | 35.63333 | −2.46667 | 8.5 |
| 12:45:25 | 35.6 | 26.7 | 31.8 | 18.55 | 35.66667 | −2.43333 | 8.3 |
| 12:45:29 | 35.5 | 26.8 | 31.8 | 18.61667 | 35.66667 | −2.43333 | 8.4 |
| 12:45:33 | 35.6 | 27.4 | 31.8 | 18.68333 | 35.66667 | −2.43333 | 8.6 |
| 12:45:37 | 35.8 | 27.5 | 31.8 | 18.75 | 35.7 | −2.4 | 8.5 |
| 12:45:41 | 35.7 | 27.2 | 31.8 | 18.81667 | 35.63333 | −2.46667 | 8.5 |
| 12:45:46 | 35.6 | 27 | 31.8 | 18.9 | 35.6 | −2.5 | 8.6 |
| 12:45:50 | 35.6 | 26.7 | 31.8 | 18.96667 | 35.63333 | −2.46667 | 8.6 |
| 12:45:54 | 35.7 | 26.8 | 31.7 | 19.03333 | 35.6 | −2.5 | 8.5 |
| 12:45:58 | 35.7 | 27.3 | 31.8 | 19.1 | 35.63333 | −2.46667 | 8.5 |
| 12:46:02 | 35.7 | 27.6 | 31.8 | 19.16667 | 35.66667 | −2.43333 | 8.5 |
| 12:46:06 | 35.6 | 27.3 | 31.8 | 19.23333 | 35.7 | −2.4 | 8.6 |
| 12:46:10 | 35.6 | 27 | 31.8 | 19.3 | 35.7 | −2.4 | 8.5 |
| 12:46:15 | 35.6 | 26.8 | 31.8 | 19.38333 | 35.66667 | −2.43333 | 8.3 |
| 12:46:19 | 35.7 | 26.9 | 31.8 | 19.45 | 35.73333 | −2.36667 | 8.4 |
| 12:46:23 | 35.6 | 27.2 | 31.8 | 19.51667 | 35.73333 | −2.36667 | 8.4 |
| 12:46:27 | 35.7 | 27.6 | 31.8 | 19.58333 | 35.76667 | −2.33333 | 8.5 |
| 12:46:31 | 35.7 | 27.4 | 31.8 | 19.65 | 35.76667 | −2.33333 | 8.5 |
| 12:46:35 | 35.6 | 27.2 | 31.8 | 19.71667 | 35.8 | −2.3 | 8.4 |
| 12:46:40 | 35.5 | 26.9 | 31.8 | 19.8 | 35.8 | −2.3 | 8.3 |
| 12:46:44 | 35.6 | 26.7 | 31.8 | 19.86667 | 35.8 | −2.3 | 8.2 |
| 12:46:48 | 35.6 | 27.1 | 31.8 | 19.93333 | 35.8 | −2.3 | 8.2 |
| 12:46:52 | 35.6 | 27.5 | 31.8 | 20 | 35.83333 | −2.26667 | 8.1 |
| 12:46:56 | 35.6 | 27.5 | 31.8 | 20.06667 | 35.8 | −2.3 | 8.1 |
| 12:47:00 | 35.7 | 27.2 | 31.8 | 20.13333 | 35.83333 | −2.26667 | 8.2 |
| 12:47:04 | 35.7 | 27 | 31.8 | 20.2 | 35.8 | −2.3 | 8.3 |
| 12:47:08 | 35.7 | 26.7 | 31.8 | 20.26667 | 35.8 | −2.3 | 8.2 |
| 12:47:13 | 35.6 | 27 | 31.8 | 20.35 | 35.8 | −2.3 | 8.1 |
| 12:47:17 | 35.7 | 27.2 | 31.8 | 20.41667 | 35.83333 | −2.26667 | 8.1 |
| 12:47:21 | 35.6 | 27.5 | 31.8 | 20.48333 | 35.83333 | −2.26667 | 8.2 |
| 12:47:25 | 35.5 | 27.3 | 31.8 | 20.55 | 35.8 | −2.3 | 8.4 |
| 12:47:29 | 35.6 | 27.1 | 31.8 | 20.61667 | 35.86667 | −2.23333 | 8.3 |
| 12:47:33 | 35.7 | 26.8 | 31.8 | 20.68333 | 35.8 | −2.3 | 8.3 |
| 12:47:37 | 35.7 | 26.7 | 31.8 | 20.75 | 35.86667 | −2.23333 | 8.2 |
| 12:47:42 | 35.7 | 27 | 31.8 | 20.83333 | 35.83333 | −2.26667 | 8.2 |
| 12:47:46 | 35.7 | 27.3 | 31.8 | 20.9 | 35.86667 | −2.23333 | 8.2 |
| 12:47:50 | 35.7 | 27.5 | 31.8 | 20.96667 | 35.8 | −2.3 | 8.2 |
| 12:47:54 | 35.7 | 27.5 | 31.8 | 21.03333 | 35.83333 | −2.26667 | 8.2 |
| 12:47:58 | 35.7 | 27.2 | 31.8 | 21.1 | 35.9 | −2.2 | 8.2 |
| 12:48:02 | 35.6 | 26.9 | 31.8 | 21.16667 | 35.9 | −2.2 | 8.2 |
| 12:48:07 | 35.6 | 26.7 | 31.8 | 21.25 | 35.9 | −2.2 | 8.2 |
| 12:48:11 | 35.5 | 26.8 | 31.8 | 21.31667 | 35.9 | −2.2 | 8.1 |
| 12:48:15 | 35.5 | 27.1 | 31.8 | 21.38333 | 35.9 | −2.2 | 8.2 |
| 12:48:19 | 35.6 | 27.5 | 31.8 | 21.45 | 35.83333 | −2.26667 | 8.1 |
| 12:48:23 | 35.6 | 27.3 | 31.8 | 21.51667 | 35.83333 | −2.26667 | 8.1 |
| 12:48:27 | 35.6 | 27.1 | 31.8 | 21.58333 | 35.86667 | −2.23333 | 8.2 |
| 12:48:32 | 35.6 | 26.8 | 31.8 | 21.66667 | 35.86667 | −2.23333 | 11.1 |
| 12:48:36 | 35.5 | 26.7 | 31.8 | 21.73333 | 35.86667 | −2.23333 | 12.8 |
| 12:48:40 | 35.5 | 27.3 | 31.8 | 21.8 | 35.83333 | −2.26667 | 12.7 |
| 12:48:44 | 35.5 | 27.6 | 31.8 | 21.86667 | 35.86667 | −2.23333 | 13.2 |
| 12:48:48 | 35.5 | 27.4 | 31.7 | 21.93333 | 35.86667 | −2.23333 | 13.8 |
| 12:48:52 | 35.6 | 27 | 31.7 | 22 | 35.86667 | −2.23333 | 14 |
| 12:48:56 | 35.5 | 26.7 | 31.7 | 22.06667 | 35.83333 | −2.26667 | 14.5 |
| 12:49:00 | 35.5 | 26.7 | 31.7 | 22.13333 | 35.86667 | −2.23333 | 10 |
| 12:49:05 | 35.3 | 27.1 | 31.7 | 22.21667 | 35.83333 | −2.26667 | 9.6 |
| 12:49:09 | 35.4 | 27.5 | 31.7 | 22.28333 | 35.86667 | −2.23333 | 8.9 |
| 12:49:13 | 35.6 | 27.3 | 31.7 | 22.35 | 35.83333 | −2.26667 | 8.6 |
| 12:49:17 | 35.5 | 27.2 | 31.7 | 22.41667 | 35.83333 | −2.26667 | 8.5 |
| 12:49:21 | 35.5 | 26.9 | 31.8 | 22.48333 | 35.8 | −2.3 | 8.6 |

TABLE 1-continued

| | | | | | | | |
|---|---|---|---|---|---|---|---|
| 12:49:25 | 35.5 | 26.8 | 31.8 | 22.55 | 35.8 | −2.3 | 8.5 |
| 12:49:30 | 35.5 | 27.2 | 31.7 | 22.63333 | 35.76667 | −2.33333 | 8.4 |
| 12:49:34 | 35.5 | 27.6 | 31.7 | 22.7 | 35.73333 | −2.36667 | 8.4 |
| 12:49:38 | 35.5 | 27.5 | 31.7 | 22.76667 | 35.73333 | −2.36667 | 8.5 |
| 12:49:42 | 35.6 | 27.4 | 31.7 | 22.83333 | 35.73333 | −2.36667 | 8.4 |
| 12:49:46 | 35.6 | 27 | 31.7 | 22.9 | 35.73333 | −2.36667 | 8.3 |
| 12:49:50 | 35.6 | 26.8 | 31.7 | 22.96667 | 35.73333 | −2.36667 | 8.3 |
| 12:49:55 | 35.6 | 27 | 31.7 | 23.05 | 35.73333 | −2.36667 | 8.3 |
| 12:49:59 | 35.5 | 27.4 | 31.7 | 23.11667 | 35.73333 | −2.36667 | 8.4 |
| 12:50:03 | 35.5 | 27.6 | 31.7 | 23.18333 | 35.7 | −2.4 | 8.4 |
| 12:50:07 | 35.5 | 27.5 | 31.7 | 23.25 | 35.7 | −2.4 | 8.3 |
| 12:50:11 | 35.6 | 27.2 | 31.7 | 23.31667 | 35.7 | −2.4 | 8.3 |
| 12:50:15 | 35.5 | 26.8 | 31.7 | 23.38333 | 35.66667 | −2.43333 | 8.3 |
| 12:50:20 | 35.5 | 26.8 | 31.7 | 23.46667 | 35.63333 | −2.46667 | 8.3 |
| 12:50:24 | 35.5 | 27.2 | 31.7 | 23.53333 | 35.63333 | −2.46667 | 8.3 |
| 12:50:28 | 35.5 | 27.6 | 31.7 | 23.6 | 35.63333 | −2.46667 | 8.2 |
| 12:50:32 | 35.5 | 27.5 | 31.7 | 23.66667 | 35.63333 | −2.46667 | 8.2 |
| 12:50:36 | 35.5 | 27.3 | 31.7 | 23.73333 | 35.63333 | −2.46667 | 8.3 |
| 12:50:40 | 35.5 | 27 | 31.7 | 23.8 | 35.63333 | −2.46667 | 8.3 |
| 12:50:44 | 35.5 | 26.8 | 31.7 | 23.86667 | 35.6 | −2.5 | 8.2 |
| 12:50:49 | 35.5 | 27.1 | 31.7 | 23.95 | 35.56667 | −2.53333 | 8.5 |
| 12:50:53 | 35.3 | 27.5 | 31.6 | 24.01667 | 35.53333 | −2.56667 | 8.3 |
| 12:50:57 | 35.3 | 27.5 | 31.6 | 24.08333 | 35.53333 | −2.56667 | 8.3 |
| 12:51:01 | 35.5 | 27.3 | 31.6 | 24.15 | 35.5 | −2.6 | 8.2 |
| 12:51:05 | 35.5 | 27 | 31.7 | 24.21667 | 35.5 | −2.6 | 8.2 |
| 12:51:10 | 35.4 | 26.8 | 31.7 | 24.3 | 35.46667 | −2.63333 | 8.2 |
| 12:51:14 | 35.3 | 26.9 | 31.7 | 24.36667 | 35.46667 | −2.63333 | 8.2 |
| 12:51:18 | 35.3 | 27.3 | 31.7 | 24.43333 | 35.5 | −2.6 | 8.1 |
| 12:51:22 | 35.4 | 27.6 | 31.7 | 24.5 | 35.46667 | −2.63333 | 8.2 |
| 12:51:26 | 35.3 | 27.4 | 31.6 | 24.56667 | 35.43333 | −2.66667 | 8.2 |
| 12:51:30 | 35.3 | 27.1 | 31.7 | 24.63333 | 35.43333 | −2.66667 | 8.2 |
| 12:51:34 | 35.3 | 26.9 | 31.7 | 24.7 | 35.43333 | −2.66667 | 8.1 |
| 12:51:39 | 35.3 | 26.8 | 31.7 | 24.78333 | 35.4 | −2.7 | 8.1 |
| 12:51:43 | 35.3 | 27.1 | 31.6 | 24.85 | 35.4 | −2.7 | 8 |
| 12:51:47 | 35.3 | 27.5 | 31.7 | 24.91667 | 35.4 | −2.7 | 8 |
| 12:51:51 | 35.3 | 27.5 | 31.6 | 24.98333 | 35.4 | −2.7 | 8 |
| 12:51:55 | 35.3 | 27.2 | 31.6 | 25.05 | 35.4 | −2.7 | 8 |
| 12:51:59 | 35.3 | 27.1 | 31.7 | 25.11667 | 35.4 | −2.7 | 8.1 |
| 12:52:04 | 35.3 | 26.8 | 31.6 | 25.2 | 35.4 | −2.7 | 8 |
| 12:52:08 | 35.3 | 26.9 | 31.6 | 25.26667 | 35.4 | −2.7 | 8 |
| 12:52:12 | 35.3 | 27.3 | 31.6 | 25.33333 | 35.4 | −2.7 | 8.1 |
| 12:52:16 | 35.3 | 27.6 | 31.7 | 25.4 | 35.36667 | −2.73333 | 8.1 |
| 12:52:20 | 35.3 | 27.4 | 31.6 | 25.46667 | 35.36667 | −2.73333 | 8.1 |
| 12:52:24 | 35.3 | 27.1 | 31.6 | 25.53333 | 35.36667 | −2.73333 | 8 |
| 12:52:28 | 35.2 | 26.8 | 31.6 | 25.6 | 35.36667 | −2.73333 | 8 |
| 12:52:32 | 35.3 | 27.1 | 31.6 | 25.66667 | 35.3 | −2.8 | 8.1 |
| 12:52:37 | 35.3 | 27.5 | 31.6 | 25.75 | 35.3 | −2.8 | 8.1 |
| 12:52:41 | 35.2 | 27.4 | 31.6 | 25.81667 | 35.3 | −2.8 | 8.1 |
| 12:52:45 | 35.3 | 27.2 | 31.6 | 25.88333 | 35.26667 | −2.83333 | 8 |
| 12:52:49 | 35.3 | 26.9 | 31.6 | 25.95 | 35.3 | −2.8 | 8 |
| 12:52:53 | 35.2 | 26.8 | 31.6 | 26.01667 | 35.3 | −2.8 | 8.1 |
| 12:52:58 | 35.2 | 27 | 31.6 | 26.1 | 35.26667 | −2.83333 | 8 |
| 12:53:02 | 35.2 | 27.4 | 31.6 | 26.16667 | 35.26667 | −2.83333 | 7.9 |
| 12:53:06 | 35.3 | 27.5 | 31.6 | 26.23333 | 35.26667 | −2.83333 | 7.9 |
| 12:53:10 | 35.3 | 27.4 | 31.6 | 26.3 | 35.3 | −2.8 | 8.1 |
| 12:53:14 | 35.3 | 27.1 | 31.6 | 26.36667 | 35.26667 | −2.83333 | 8 |
| 12:53:18 | 35.2 | 26.9 | 31.6 | 26.43333 | 35.26667 | −2.83333 | 8 |
| 12:53:22 | 35.2 | 26.8 | 31.6 | 26.5 | 35.23333 | −2.86667 | 8 |
| 12:53:27 | 35.2 | 27.1 | 31.6 | 26.58333 | 35.26667 | −2.83333 | 8 |
| 12:53:31 | 35.2 | 27.5 | 31.6 | 26.65 | 35.26667 | −2.83333 | 7.9 |
| 12:53:35 | 35.2 | 27.5 | 31.6 | 26.71667 | 35.23333 | −2.86667 | 8 |
| 12:53:39 | 35.2 | 27.3 | 31.6 | 26.78333 | 35.26667 | −2.83333 | 8 |
| 12:53:43 | 35.2 | 27 | 31.6 | 26.85 | 35.23333 | −2.86667 | 8 |
| 12:53:47 | 35.1 | 26.8 | 31.6 | 26.91667 | 35.23333 | −2.86667 | 8 |
| 12:53:51 | 35.3 | 26.9 | 31.6 | 26.98333 | 35.23333 | −2.86667 | 8 |
| 12:53:55 | 35.4 | 27.2 | 31.6 | 27.05 | 35.23333 | −2.86667 | 7.9 |
| 12:54:00 | 35.5 | 27.5 | 31.6 | 27.13333 | 35.23333 | −2.86667 | 8 |
| 12:54:04 | 35.4 | 27.4 | 31.6 | 27.2 | 35.23333 | −2.86667 | 8 |
| 12:54:08 | 35.4 | 27.1 | 31.6 | 27.26667 | 35.23333 | −2.86667 | 7.8 |
| 12:54:12 | 35.4 | 26.8 | 31.6 | 27.33333 | 35.23333 | −2.86667 | 7.8 |
| 12:54:16 | 35.1 | 26.8 | 31.6 | 27.4 | 35.23333 | −2.86667 | 7.8 |
| 12:54:20 | 35 | 27.1 | 31.6 | 27.46667 | 35.23333 | −2.86667 | 8 |
| 12:54:24 | 35 | 27.5 | 31.6 | 27.53333 | 35.23333 | −2.86667 | 8 |
| 12:54:29 | 34.8 | 27.5 | 31.6 | 27.61667 | 35.23333 | −2.86667 | 7.8 |
| 12:54:33 | 34.8 | 27.3 | 31.6 | 27.68333 | 35.23333 | −2.86667 | 7.8 |
| 12:54:37 | 34.9 | 27 | 31.6 | 27.75 | 35.26667 | −2.83333 | 7.4 |
| 12:54:41 | 35 | 26.8 | 31.6 | 27.81667 | 35.23333 | −2.86667 | 8.7 |

Figure 39:
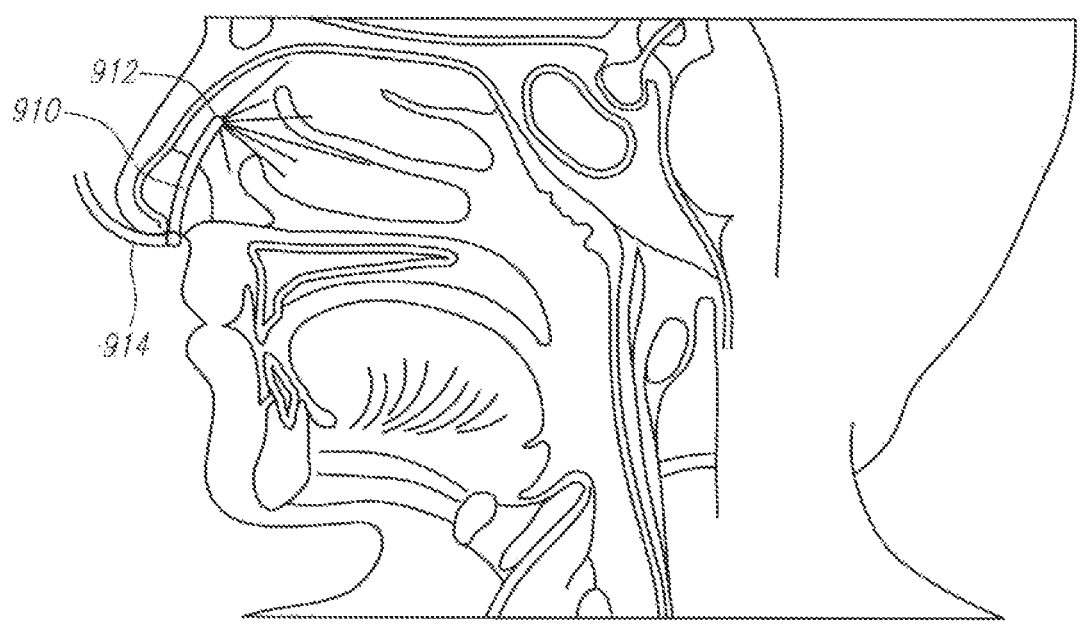
FIG. 39 illustrates an embodiment of a device having a spray nozzle constructed according to the present invention for non-invasive cerebral and systemic cooling via the nasal cavity.

FIG. 39 illustrates nasal catheter 910 for non-invasive cerebral and systemic cooling of the nasal cavity. The nasal catheter has a rounded sealed tip 912 on the distal end, which provides a smooth surface to avoid damaging sensitive tissues. Tip 912 may be sealed by selective melting of the distal end of the catheter. In use, catheter 910 is intended to be placed in the nares of the nose, so that a spray outlet (not shown) may be directed at the desired structures of the nasal cavity, specifically the nasal conchae. The spray nozzle on the distal end of nasal catheter 10 is designed so as to cause the spray to spread in a pattern which will allow the gas/liquid mixture to contact as much of the desired tissues as possible. By doing this, any mechanical trauma due to a concentrated high velocity jet should be minimized.

Figure 43A:
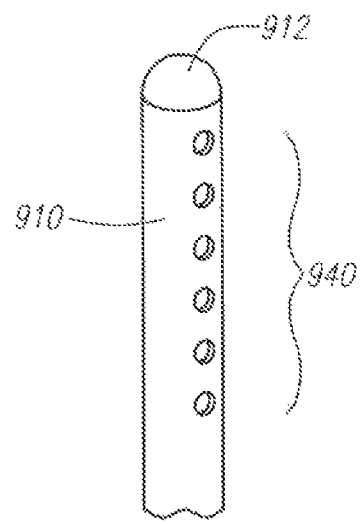
FIG. 43A illustrates an embodiment of a spray nozzle for use with the present invention.
Figure 43B:
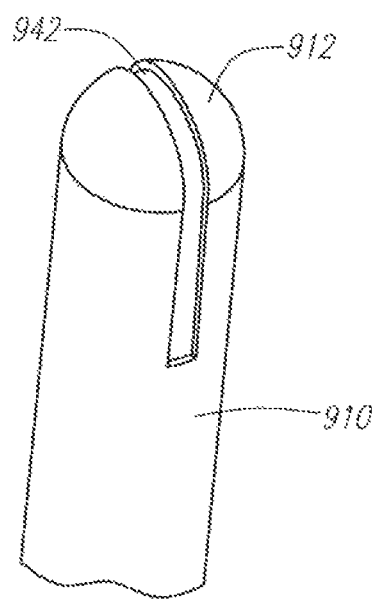
FIG. 43B illustrates an embodiment of a spray nozzle for use with the present invention.
Figure 43C:
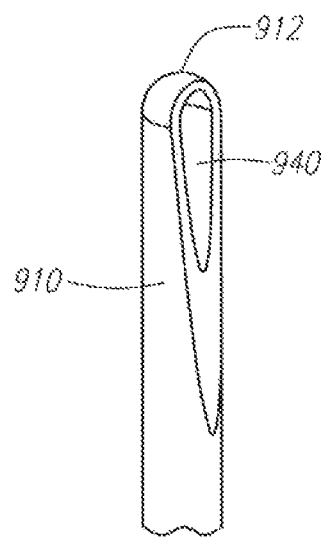
FIG. 43C illustrates an embodiment of a spray nozzle for use with the present invention.
Figure 44:
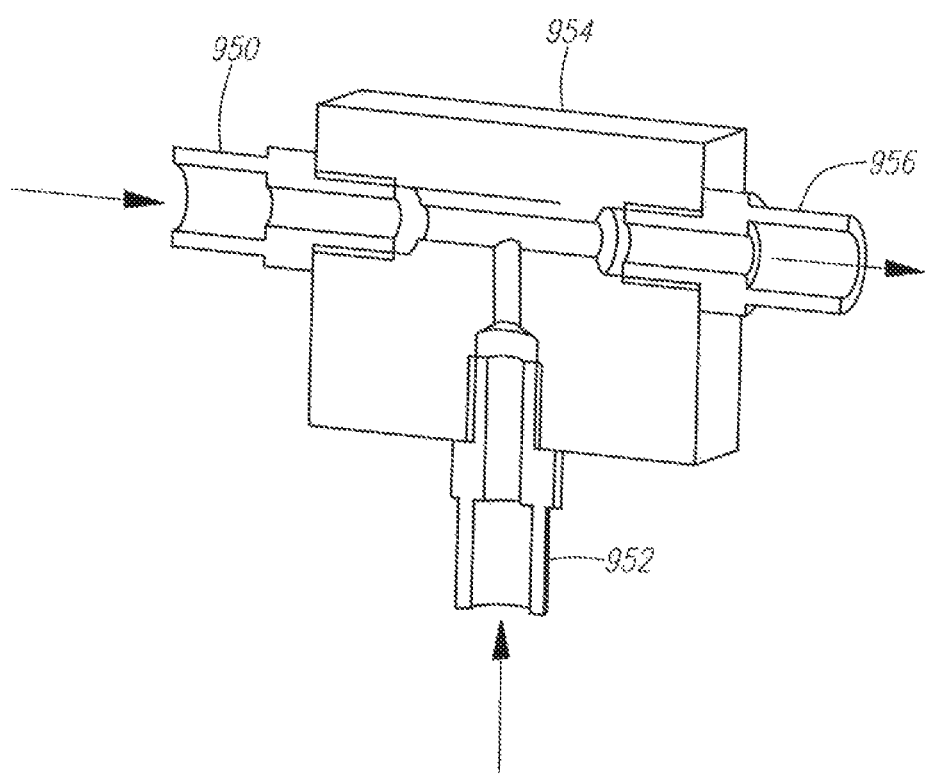
FIG. 44 illustrates a mixing block for mixing the liquid and gas at the point of administration constructed according to the present invention.

FIGS. 43A-C depict several possible designs for the spray nozzle for creating varying spread spray patterns. FIG. 43A shows nasal catheter 910 wherein the spray nozzle has been formed by drilling multiple holes 940 along the outer wall of nasal catheter 910. In use, this pattern produces will produce a broad, flat spray perpendicular to the axis of the catheter. This pattern may be further customized by drilling corresponding holes in the opposite side of the catheter wall (not show), or by changing the size, location and number of holes drilled in the catheter outer wall. In addition, it may also be possible to include a hole in the catheter tip 12 (hole not shown), to produce some additional flow in the axial direction.

FIG. 43B shows nasal catheter 910, wherein the spray nozzle has been formed by cutting a rectangular slit 942 in tip 912 of catheter 910. In use, this pattern produces a fan shaped spray centered along the axial direction of the catheter. Here, the width and length of slit 942 will dictate the character of the spray. The pattern may, therefore be customized by varying the width and length of slit 942. In addition, the symmetry of the spray may be altered by cutting slit 942 to extend farther down one side catheter 910 than the other. Alternatively, the spray pattern may be altered by adding one or more additional slits of varying widths and lengths (not shown).

FIG. 43C shows a nasal catheter 910, wherein the spray nozzle has been formed by making an angled straight cut 944 or a curved cut (not shown) in the side of catheter 910, including a portion of catheter tip 912. In use, this skived cut produces a wide 'fan' shaped spray which covers a broad angle from the perpendicular to the axial directions of catheter 910. In addition, any of the patterns depicted in FIGS. 43A-C could also be combined to further disperse the spray. For example, holes could be cut along the length of a skived tip catheter to cover a wider area, or a slit could be cut in the tip of a the drilled hole catheter to enhance flow in the axial direction.

Figure 40:
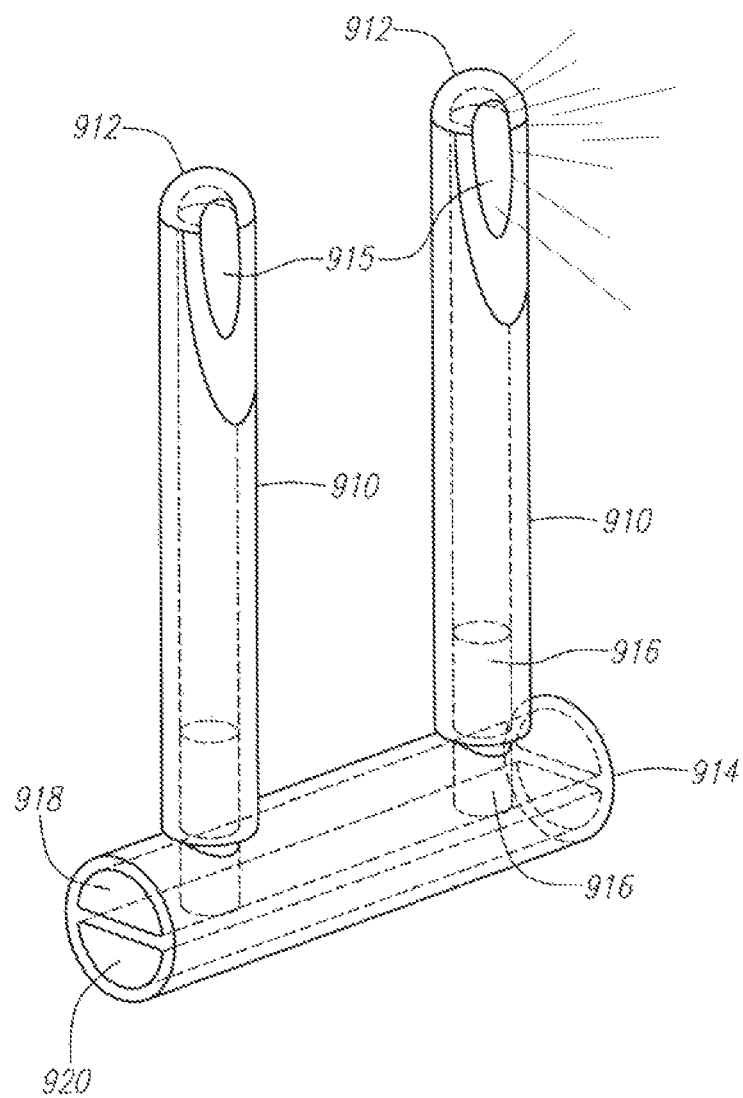
FIG. 40 illustrates an embodiment of a delivery system constructed according to the present invention for delivery of a liquid and gas for non-invasive cerebral and systemic cooling of the nasal cavity.

FIG. 40 shows a dual-lumen mixing catheter 914 connected to two nasal catheters 910 for separately delivering a liquid and a gas to the proximal end of each nasal catheter 910. In use, nasal catheter 910 will be placed a distance apart appropriate for the nares of the desired patient, and made a length appropriate for administration at the targeted tissues. The dual-lumen mixing catheter 914 comprises an upper lumen 918 and a lower lumen 920 used to separately deliver the liquid and the gas. This mixing catheter may be constructed as a single ended device, or made into a loop (not shown) similar to a standard nasal cannula for oxygen therapy. The 'loop' configuration aids in placement on the patient, as it may be routed over and behind the ears to hold it in place. The loop configuration also helps ensure equal flow when two nasal catheters are used.

Figure 41:
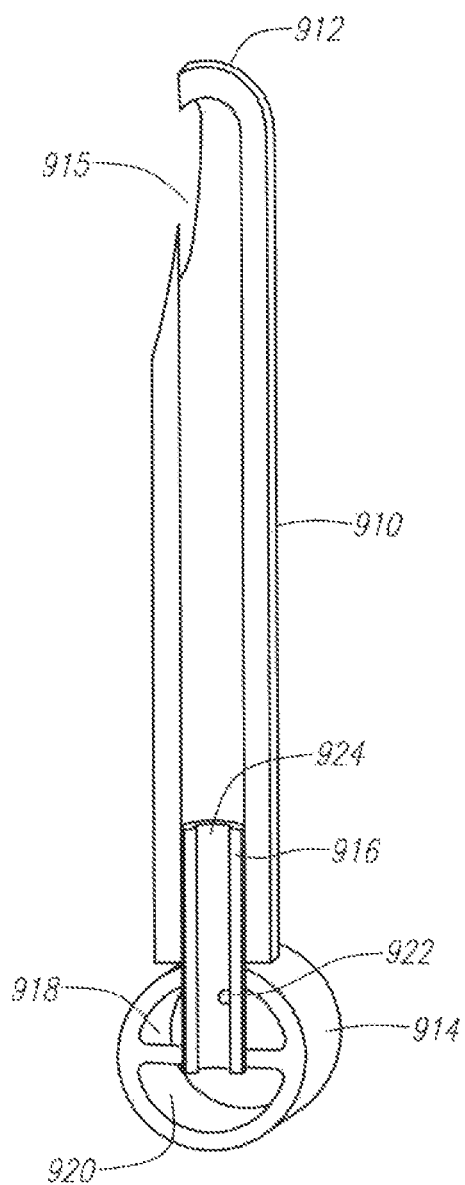
FIG. 41 illustrates an embodiment of a connecting tube for connecting the nasal catheter to the liquid delivery system constructed according to the present invention.
Figure 42:
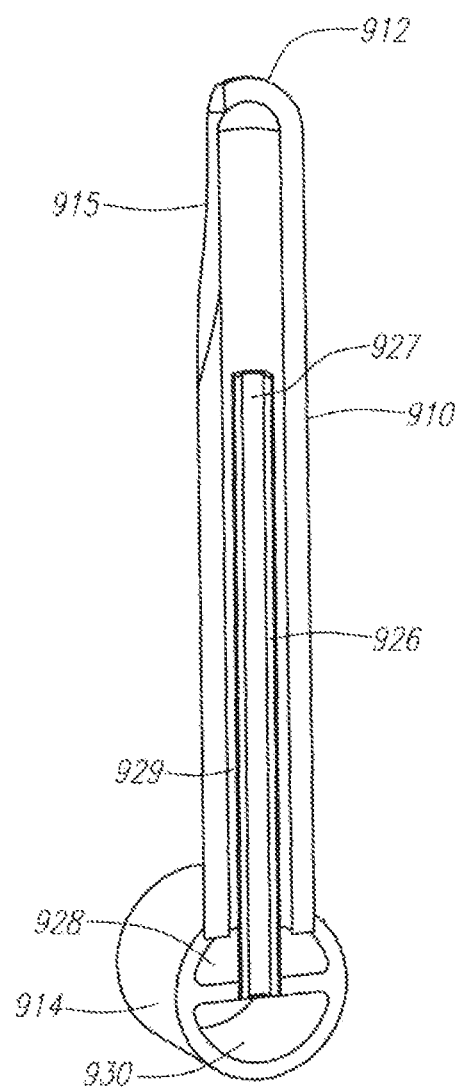
FIG. 42 illustrates an embodiment of a connecting tube for connecting the nasal catheter to the liquid delivery system constructed according to the present invention.

Nasal catheter 910 is connected to mixing catheter 914 by a connecting tube 916. Connecting tube 916 is a hollow, open ended tube for attaching nasal catheter 910 to mixing catheter 914 and for placing nasal catheter 910 in fluid communication with at least the lower lumen 920 of mixing catheter 914. It can be made from metal 'hypodermic' tubing, or a suitable plastic. As shown in FIG. 41, the connecting tube 916 has an outer diameter sized to fit tightly in the lumen of nasal catheter 910 and thus form a seal between nasal catheter 910 and mixing catheter 914. Once assembled, an over layer of glue or other compound such as silicone may be used to ensure a durable connection and smooth texture for patient comfort. In use, open ended, hollow tub 924 of connecting tube 916 places the lumen of nasal catheter 910 in fluid communication with the lower lumen 920 of mixing catheter 910. In this configuration, the gas is supplied through the lower lumen 920 of the dual lumen tubing 914. The gas flows through the lower lumen 920 and up through the lumen 924 of connecting tube 916 into the nasal catheter(s) 910. At the same time, the liquid is supplied through the upper lumen 918 of mixing catheter 914. The liquid passes into the lumen 924 of connecting tube 916 via a small hole 922 drilled in the wall of connecting tube 916. The inner diameter of the tube and the size of fluid hole 922 are important parameters in the optimization of the spray pattern.

At this point, the gas is moving at a high velocity, and the liquid experiences high shear forces, breaking the stream into small droplets that then flow through the lumen of nasal catheter 910 and are delivered as a spray to the patient's nasal cavity through the spray nozzle 915.

FIG. 42 illustrates an alternate embodiment of a mixing catheter. The dual lumen tubing 914 is used as above, and catheter tip 912, including a spray nozzle 915 is also as previously described. In this embodiment, however, the mixing of the air and liquid occurs very near tip 912. The liquid is delivered through lower lumen 930 and the gas is delivered through upper lumen 928 of mixing catheter 914. The nasal catheter is secured directly to an aperture in upper lumen 928 so that a small diameter liquid delivery tube 926 extending perpendicularly from lower lumen 930 of mixing catheter 914 is positioned inside the lumen of the nasal catheter 910. Liquid tube 926 is a hollow, open ended tube extending through the lumen of nasal catheter 910 to the distal region of nasal catheter 910. Liquid tube 926 has an outer diameter smaller than the inner diameter of nasal catheter 910 and smaller than the aperture connecting nasal catheter 910 to mixing catheter 914. In use, the liquid flows through lumen 927 of liquid tube 926 while the gas flows through upper lumen 928 and enters nasal catheter 910 via the annular space 929 between liquid tube 926 and the inside diameter of catheter 910. Turbulence and other flow effects, such as Bernoulli pressure, at the end of liquid tube 926 cause the fluid to be broken up into small droplets. This design requires less pressure to drive the liquid, and may aid in matching the liquid and gas flows.

FIG. 44 illustrates an alternative embodiment of a gas and liquid delivery system that may be attached the proximal end of the nasal catheter whereby the liquid and the gas are delivered to the catheter through their own tubes 950 and 952 and mixed at the point of administration to the patient, rather than prior to use. This ensures that even an unstable spray can be delivered to the desired region. Furthermore, because the liquid begins to evaporate immediately upon contact with the gas, mixing at the point of use in the patient will ensure efficient use of all available cooling. As seen in FIG. 44, the mixing device may comprise a mixing block 954 including at least two input flow channels 950 and 952 and a single output flow channel 956. Mixing block 954 may be machined from metal, plastic, or molded from plastic. The two input flow channels 950 and 952 may be connected to two separate tubes containing a liquid and a compressed gas. Input channels 950 and 952 may then be joined in mixing block 954 so that the liquid and gas carried by the input tubes will be combined, after which the combined liquid/gas mixture may then flow through output channel 956. The nasal catheter may be attached to output channel 956 for delivery of the combined liquid/gas mixture to the patient's nasal cavity.

Figure 46:
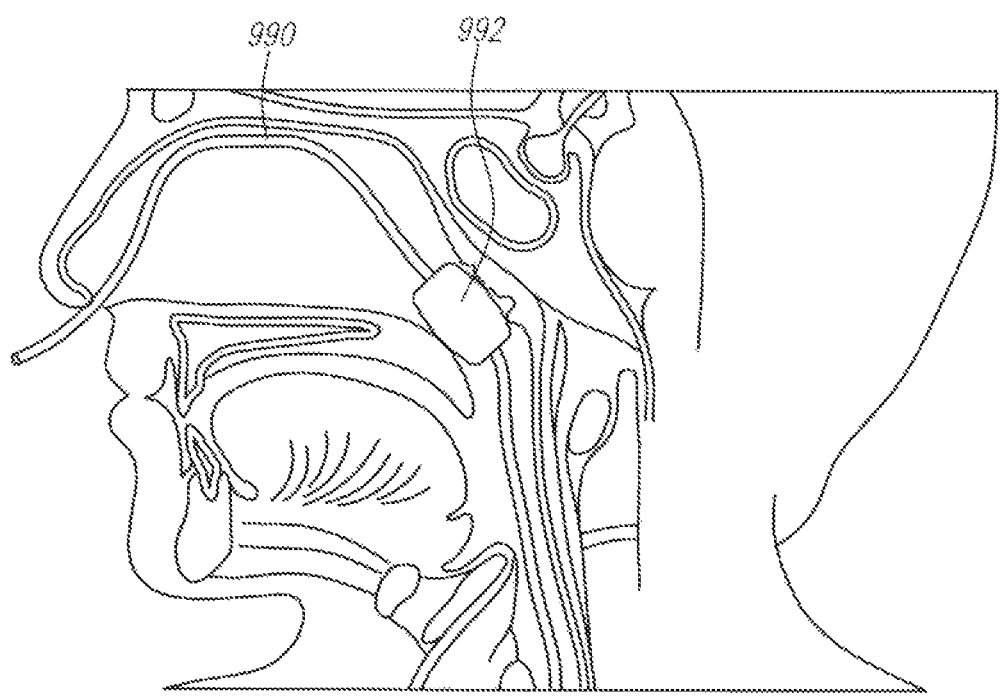
FIG. 46 illustrates an embodiment of a device having an expandable member constructed according to the present invention for non-invasive cerebral and systemic cooling via the nasal cavity.

FIG. 46 illustrates an alternative nasal catheter for cooling the nasal cavity with cold saline. Here, nasal catheter 990 includes an elongate tubular member, operably sized to extend into the patient's nasopharynx with expandable member 992 mounted on the distal end of catheter 990. In use, nasal catheter 990 is inserted into one of the patient's nostrils and positioned in the nasopharynx. Once positioned in the nasopharynx, expandable member 992 is expanded to conform to the nasopharynx and form a seal isolating the nasal cavity from the rest of the patient's airways. Once isolated, cold saline is injected into one of the patient's nostrils and circulated though the nasal cavity to allow for rapid cooling of the patient's head. Expandable member 992 prevents the saline from entering the patients other airways. The saline may then by allowed to run out the patient's other nostril or may be suctioned from the patient's nasal cavity from a suction port (not shown) proximal to expandable member 992. In addition, a second nasal catheter (not shown), also comprising an elongate tubular member with an expandable member mounted on the distal end, may be inserted in the patient's second nostril. Here, the balloons may be positioned on either side of the nasal cavity before the septum and expanded to isolate the nasal cavity from the rest of the patient's airways.

Figure 47:
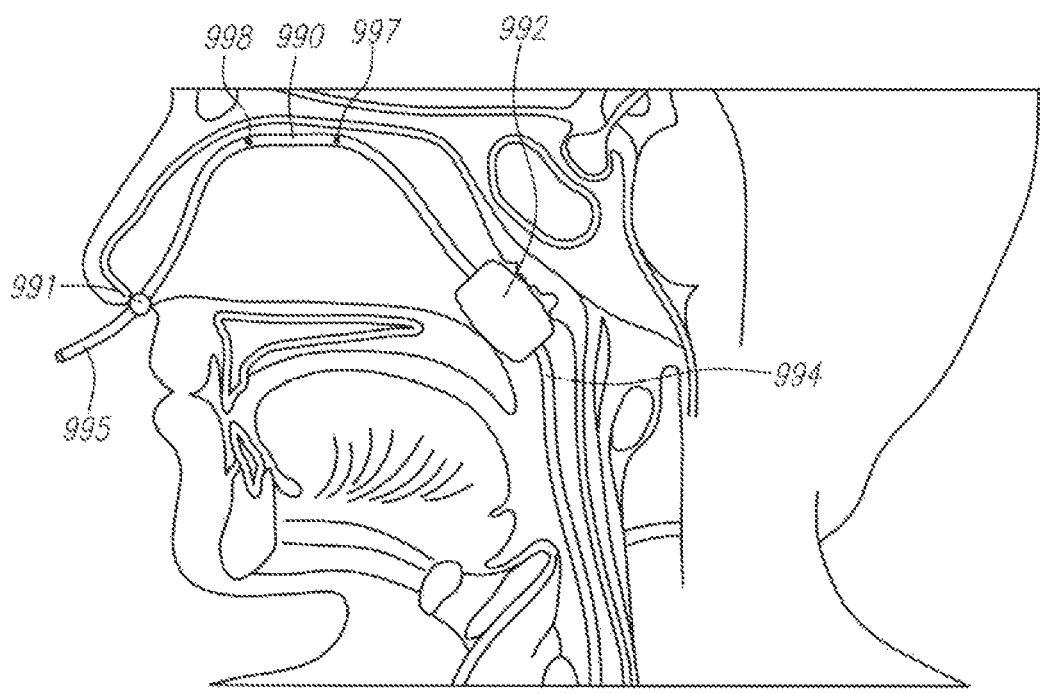
FIG. 47 illustrates an embodiment of a device having proximal and distal expandable members constructed according to the present invention for non-invasive cerebral and systemic cooling via the nasal cavity.
Figure 48:
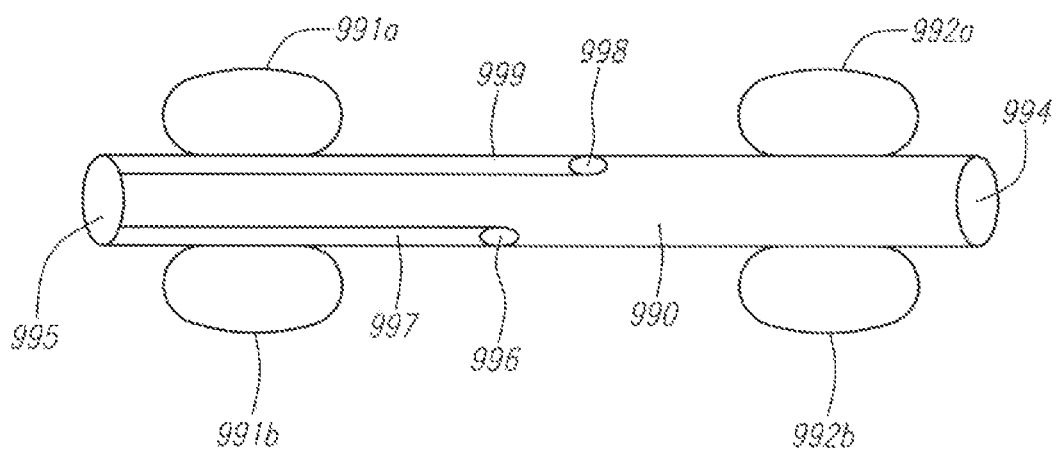
FIG. 48 illustrates an embodiment of a device having proximal and distal expandable members constructed according to the present invention for non-invasive cerebral and systemic cooling via the nasal cavity.

FIGS. 47-48 show an alternative nasal catheter for cooling the nasal cavity with a cold liquid. Here, nasal catheter 990 includes an elongate tubular member, operably sized to extend into the patients nasopharynx and at least one expandable member 992 mounted near the distal end of the elongate tubular member and two expandable members 991*a-b* mounted near the proximal end of catheter 990. In use, nasal catheter 990 is inserted into one of the patient's nostrils and positioned in the nasopharynx. Once positioned in the nasopharynx, expandable member 992 is expanded to conform to the nasopharynx and form a seal isolating the nasal cavity from the rest of the patient's airways and the expandable members 991*a-b* at the proximal end are positioned in the patients nostrils to seal the patient's nasal cavity. Alternatively, as depicted in FIG. 48, the distal end may have two expandable members 992*a-b* that may be positioned at the posterior aspect of the nasal cavity to isolate the nasal cavity from the pharynx. Catheter 990 also has openings 994 and 995 at the distal and proximal ends, respectively, to provide a breathing passage while the nasal cavity is sealed. Once the nasal cavity is isolated, a cold fluid may be delivered to the nasal cavity via delivery lumen 997, which is in fluid communication with port 996. Alternatively, a tube comprising a spray nozzle (not shown) may be inserted in the delivery lumen 997 to deliver a liquid spray to the nasal cavity.

Expandable members 992*a-b* and 991*a-b* at the distal and proximal ends of catheter 990 prevent non-vaporized fluid from leaking into the throat or running out of the patient's nostrils. The non-vaporized liquid may then be suctioned form the nasal cavity via suction lumen 999, which is in fluid communication with port 998. This liquid may be discarded or alternatively it may be recycled for successive use. Because there is a dedicated lumen for delivery and suction, however, delivery of the cooled liquid to the nasal cavity does not need to be interrupted.

Convective Cooling in the Nasal Cavity

Figure 22A:
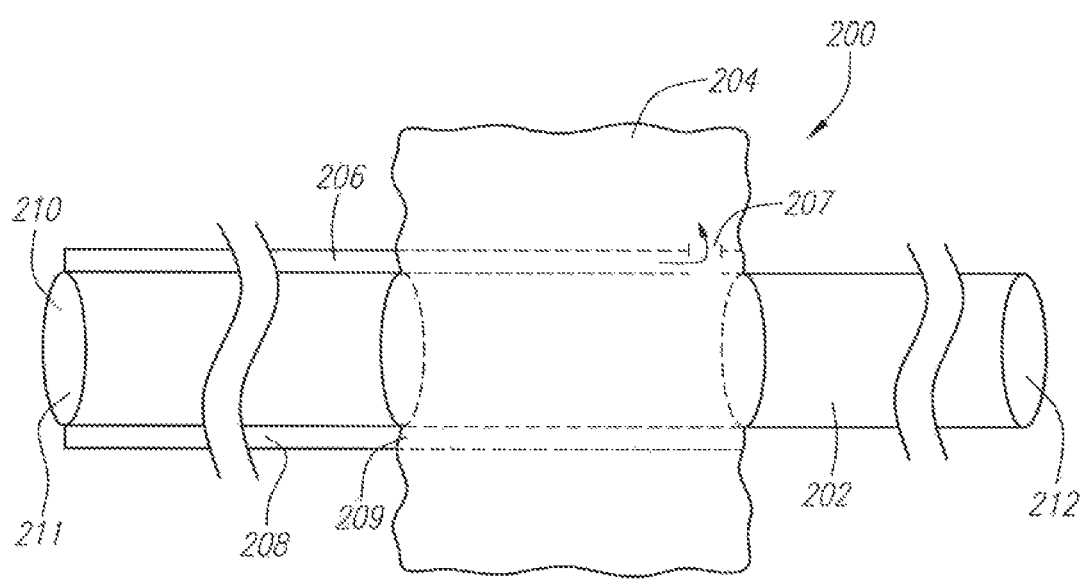
FIG. 22A illustrates an embodiment of a device having a flexible balloon mounted on an elongate tubular member for insertion into the nasal cavity.

In another aspect of this invention, a catheter with a flexible balloon having a chamber filled with a cooling liquid can be used to cool the brain via the nasal cavity. As seen in FIG. 22A, assembly 200 includes flexible balloon 204 that is mounted circumferentially around catheter 202. Catheter 202 has ports 211, 212 at the proximal and distal ends and lumen 210 extending therebetween that enables the patient to breathe while the catheter is in use. Ports 211, 212 and lumen 210 are in fluid communication with the patient's nasopharynx, pharynx, larynx, and/or esophagus. Catheter 202 is approximately 8 cm in length, alternatively approximately 10 cm in length, alternatively approximately 12 cm in length, alternatively approximately 14 cm in length, alternatively approximately 16 cm in length, alternatively approximately 18 cm in length, alternatively approximately 20 cm in length. Lumens 206, 208 are in fluid communication with the chamber of the flexible balloon 204 through ports 207, 209 located at the distal ends. At their proximal ends, lumens 204, 206 are connected to a refrigerated pump (not shown) that is capable of recycling a cooling fluid through the chamber of the flexible balloon 204.

Figure 22B:
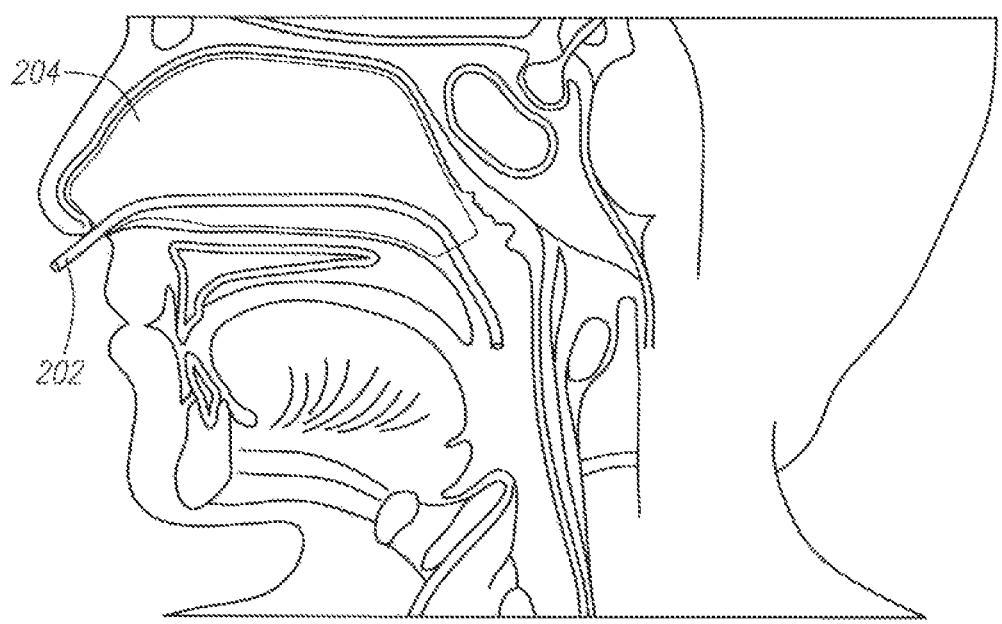
FIG. 22B illustrates the device of FIG. 22A inserted into a nasal cavity.

In use, as seen in FIG. 22B, assembly 200 is inserted into the nasal cavity through the patient's nostril such that flexible balloon 204 is within the nasal cavity and the distal end of catheter 202 extends through the narices to the nasopharyngeal region of the nasal cavity. A cooling liquid or fluid can then be used to inflate or infuse the chamber of flexible balloon 204 to a sufficient pressure such that flexible balloon 204 expands and is in contact with a substantial portion of the nasal cavity. The cooling fluid may then be recirculated through the chamber of flexible balloon 204 via lumens 206, 208 and a refrigerated bath/pump (not shown). Optionally, the cooling fluid can be withdrawn or suctioned back out of flexible balloon 204 at a rate sufficient to induce or maintain a desired balloon pressure or brain temperature. Additionally, a second assembly can also be inserted into the other nostril such that maximum cooling can be obtained. The cooling of the brain would occur by convection or heat exchange from the cold liquid in the chamber of the balloon to the warm nasal cavity. Lumen 210 of catheter 202 allows the patient to breathe through his nose after the flexible balloon 204 is inflated. Alternatively, when the patient is getting oxygen through alternative means, other medical devices can be passed through lumen 210. These medical devices include, but are not limited to, oxygen tube, nasogastric tube, fiber optics, laryngoscope, pH probes, and esophageal manometry.

Figure 23A:
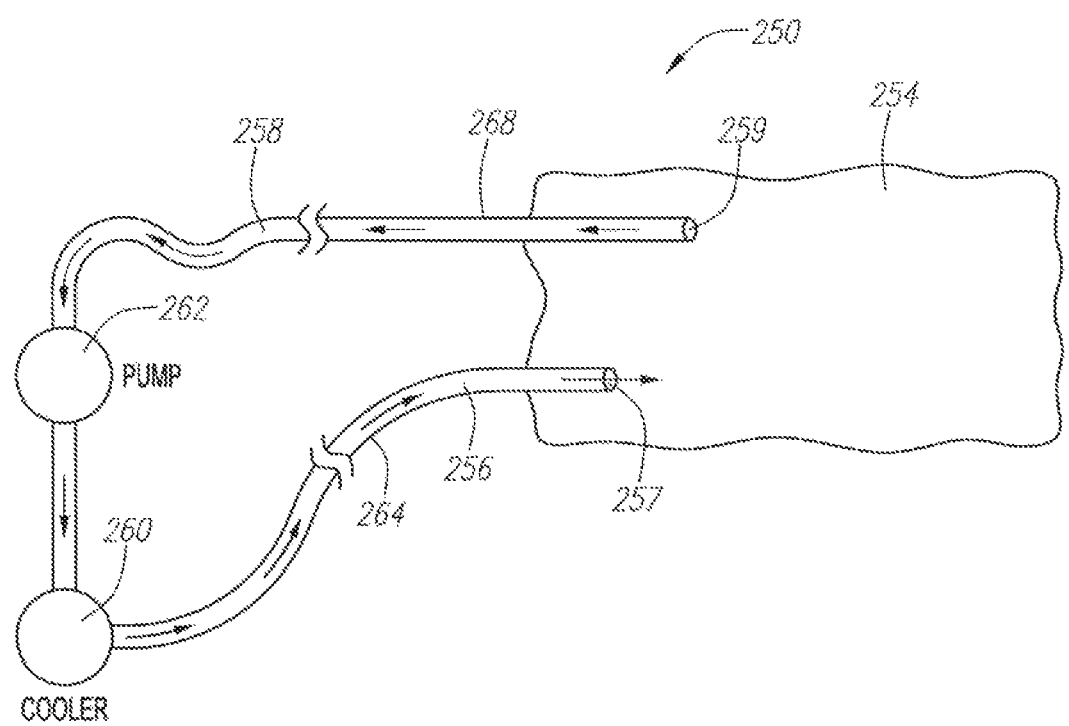
FIG. 23A illustrates an alternative embodiment of a flexible balloon device for insertion into a nasal cavity.

In an alternative embodiment, a flexible balloon having a chamber filled with a cooling liquid can be used to cool the brain via the nasal cavity. As seen in FIG. 23A, assembly 250 includes flexible balloon 254 that has a chamber that is in fluid communication with lumens 256, 258 of elongate tubular members 264, 268 through ports 257, 259 located at their distal ends. At their proximal ends, elongate tubular members 264, 268 may be connected to cooler 260 and pump 262 that infuse and/or recirculate the cooling liquid through lumens 256, 258 and the chamber of flexible balloon 254. Alternatively, elongate tubular members 264, 268 may be connected to a refrigerated pump (not shown) that is capable of pumping and/or recirculating the cooling fluid.

Figure 23B:
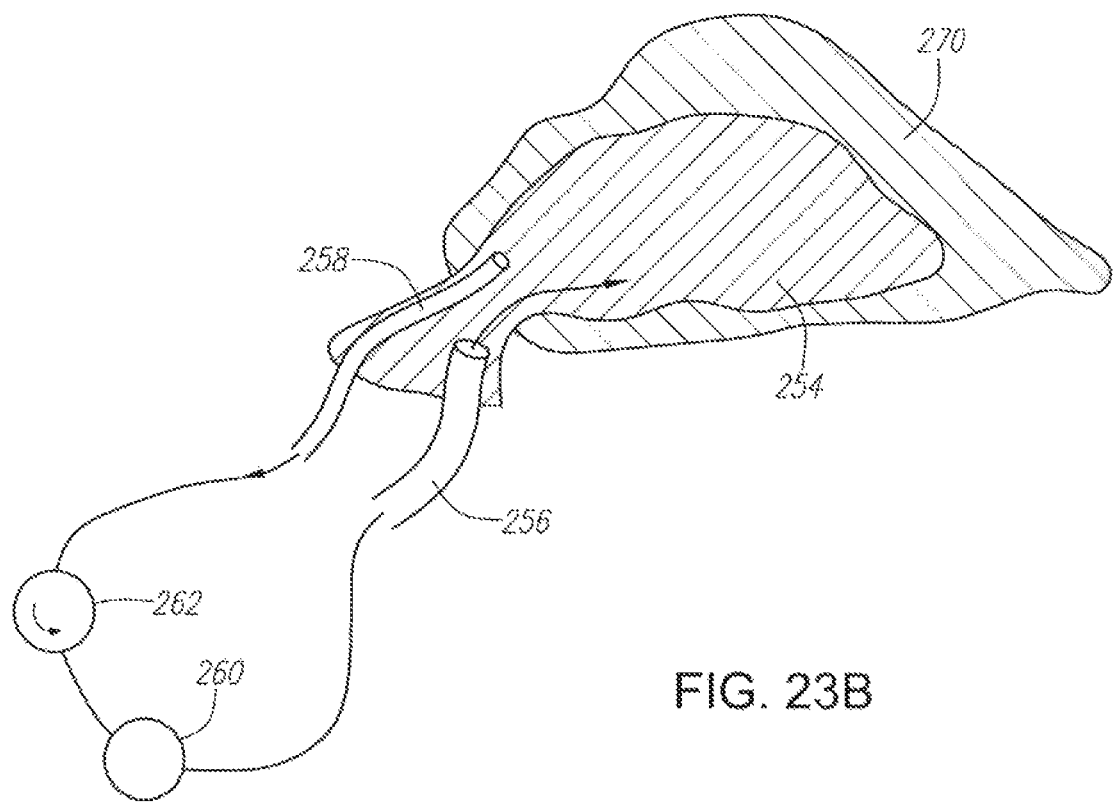
FIG. 23B illustrates the device of FIG. 23A inserted into a nasal cavity.

In use, as seen in FIG. 23B, assembly 250 is inserted into the nasal cavity through a nostril such that flexible balloon 254 is within the nasal cavity 270. A cooling fluid can then be used to inflate flexible balloon 254 to a sufficient pressure such that flexible balloon 254 expands and is in contact with a substantial portion of the nasal cavity. The cooling fluid is then recirculated through flexible balloon 254 via lumens 256, 258, cooler 260, and pump 262. Optionally, the cooling fluid can be suctioned back out of flexible balloon 254 at a rate sufficient to induce or maintain a desired balloon pressure or brain temperature. Additionally, a second assembly can also be inserted into the other nostril such that maximum cooling can be obtained. The cooling of the brain would occur by convection or heat exchange from the cold liquid in the balloon to the warm nasal cavity.

Figure 29:
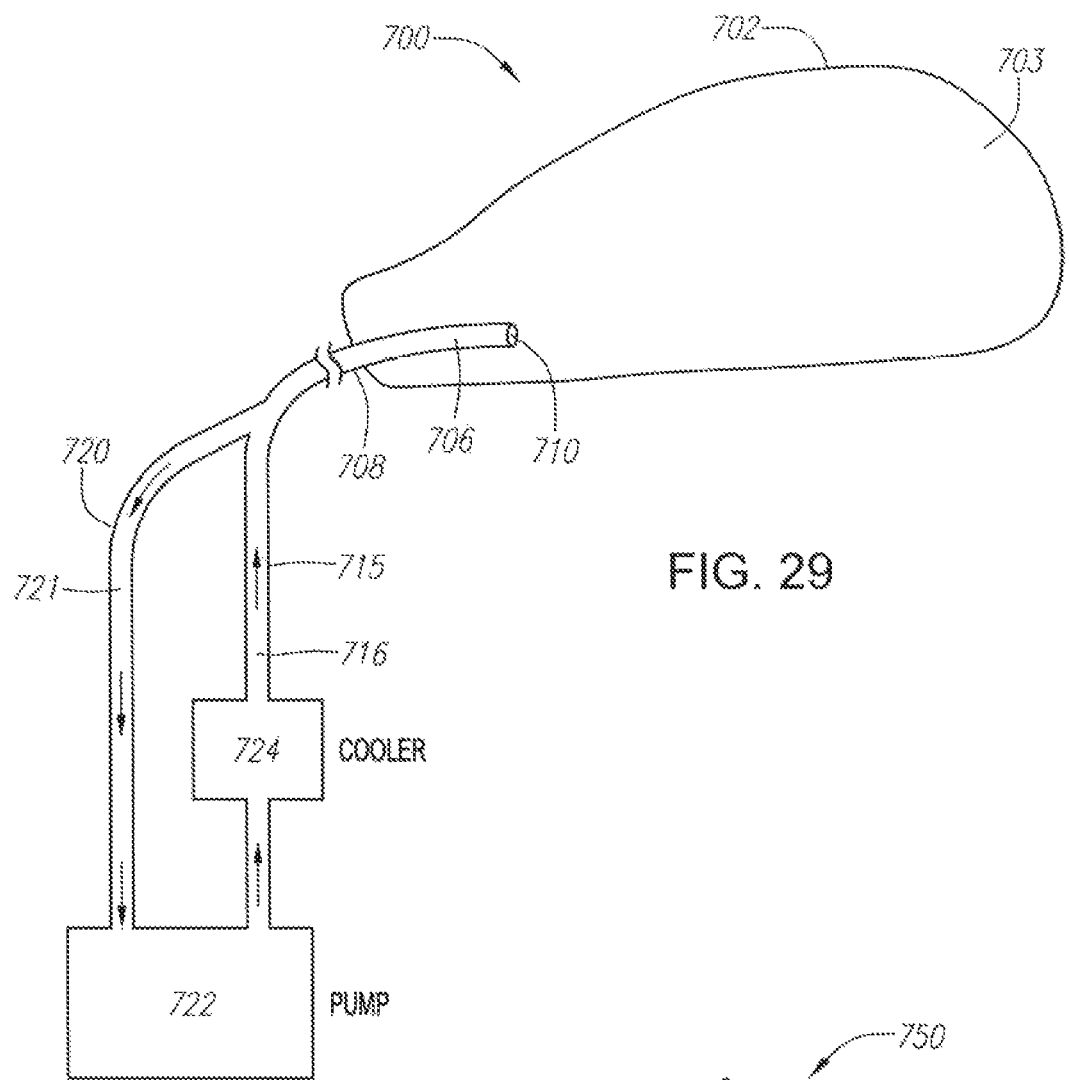
FIG. 29 illustrates an embodiment of a device having a flexible balloon mounted on a branched elongate tubular member for insertion into the nasal cavity.

In an alternative embodiment, a flexible balloon having a chamber filled with a cooling liquid can be used to cool the brain via the nasal cavity. As seen in FIG. 29, assembly 700 includes flexible balloon 702 that has a chamber 703 that is in fluid communication with lumen 706 of elongate tubular member 708 through port 710 located at its distal end. At a point outside of chamber 703, elongate tubular member 708 branches into two elongate tubular members 715 and 720 having lumens 716 and 721, respectively. Elongate tubular members 720 and 715 are in communication with each other through pump 722, e.g., a piston pump, and cooler 724, located at or near the proximal ends of elongate tubular members 715 and 720. Cooler 724 and pump 722 infuse and/or recirculate the cooling liquid through lumens 716 and 721 and the chamber of flexible balloon 254. This single lumen design may allow for faster inflation and deflation. Alternatively, elongate tubular members 715 and 720 may be connected to a refrigerated pump (not shown) that is capable of pumping and/or recirculating the cooling fluid.

In use, assembly 700 is inserted into the nasal cavity through a nostril such that flexible balloon 702 is within the nasal cavity. A cooling fluid can then be used to inflate flexible balloon 702 to a sufficient pressure such that flexible balloon 702 expands and is in contact with a substantial portion of the nasal cavity. The cooling fluid is then recirculated through flexible balloon 702 via lumens 706, 716, and 721, cooler 722, and pump 724. For instance, cooling liquid may be withdrawn from chamber 703 by having a pump 722 withdraw then cooling liquid through lumens 706 and 721 of elongate tubular members 708 and 720, respectively. Cooling liquid can then be pumped into cooler for further cooling and then pumped back into chamber 703 through lumens 716 and 706 of elongate tubular members 715 and 708. In order to optimize cooling and minimize tissue damage, it may be desirable to continuously inflate and deflate flexible balloon 702. Additionally, a second assembly can also be inserted into the other nostril such that maximum cooling can be obtained. The cooling of the brain would occur by convection or heat exchange from the cold liquid in the balloon to the warm nasal cavity.

Figure 27:
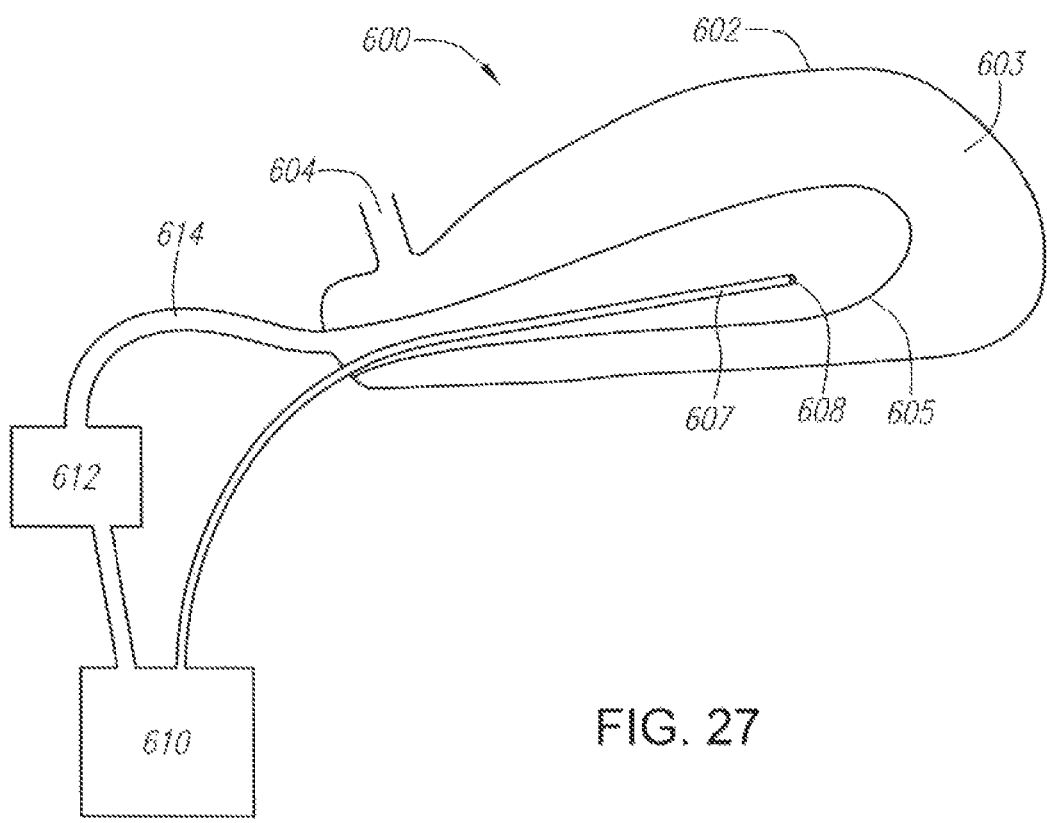
FIG. 27 illustrates an embodiment of a device having a flexible balloon and a cold probe for insertion into the nasal cavity.

In an alternative embodiment, a flexible balloon having a chamber filled with a cooling liquid and a cold finger inside of a second balloon can be used to cool the brain via the nasal cavity. As seen in FIG. 27, assembly 600 includes flexible balloon 602 that has chamber 603 that is in fluid communication with port 604. A cooling liquid, such as water or saline, can be infused into chamber 603 through port 604. A second balloon 605 containing a cold probe 607 is contained within chamber 603 to cool the liquid inside flexible balloon 602. A cooling agent, such as Freon or other PFC, that is approximately 0° C., alternatively approximately −1° C., alternatively approximately −2° C., alternatively approximately −3° C., alternatively between about −5° C. and 5° C., alternatively between about −5° C. and 0° C., will be flowed through cold probe 607. The flow rate of the cooling agent will depend on the type used. The flow rate will be chosen to produce between about 150 and about 300 watts. Additionally, cold probe 607 may be connected to cooler 610. Second balloon 605 may be in fluid communication with a port and allowed to vent to the atmosphere (not shown). Alternatively, second balloon 605 may be in fluid communication with a compressor 612 through elongate tubular member 614 to circulate the cooling liquid.

Cold probe 607 may also have fins surrounding the cold probe (not shown) to increase the surface area of the probe. Alternatively, a heat pipe could be used in place of the cold probe. The heat pipe could be filled with a gas such as Freon or ammonia, or alternatively, the heat pipe could be connected to a circulating cooling liquid reservoir or other cooling source (such as a block of ice).

In use, assembly 600 is inserted into the nasal cavity through the patient's nostril such that flexible balloon 602 is within the nasal cavity. A cooling fluid can then be used in inflate flexible balloon 602 to a sufficient pressure such that flexible balloon 602 expands and is in contact with a substantial portion of the nasal cavity. The cooling agent will then be circulated into second balloon 605 via port 608 at the distal end of cold probe 607 and elongate tubular member 614. Alternatively, the cooling agent may not be recirculated, but rather be vented out of a port in second balloon 605 (not shown). Additionally, the fluid in the balloon can be agitated to prevent freezing. This may be accomplished by moving cold probe 607 or pulsing the infusion of the cooling agent into second balloon 605. Additionally, a second assembly can also be inserted into the other nostril such that maximum cooling can be obtained. The cooling of the brain would occur by convection or heat exchange from the cold liquid in the balloon to the warm nasal cavity.

Figure 28A:
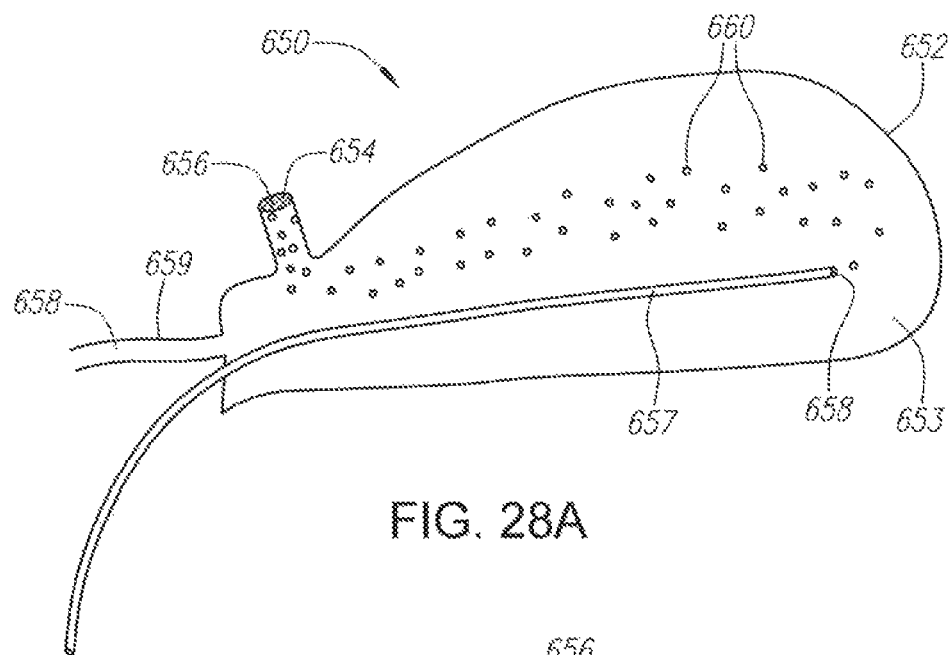
FIG. 28A illustrates an alternative embodiment of a device having a flexible balloon and a cold probe for insertion into the nasal cavity.
Figure 28B:
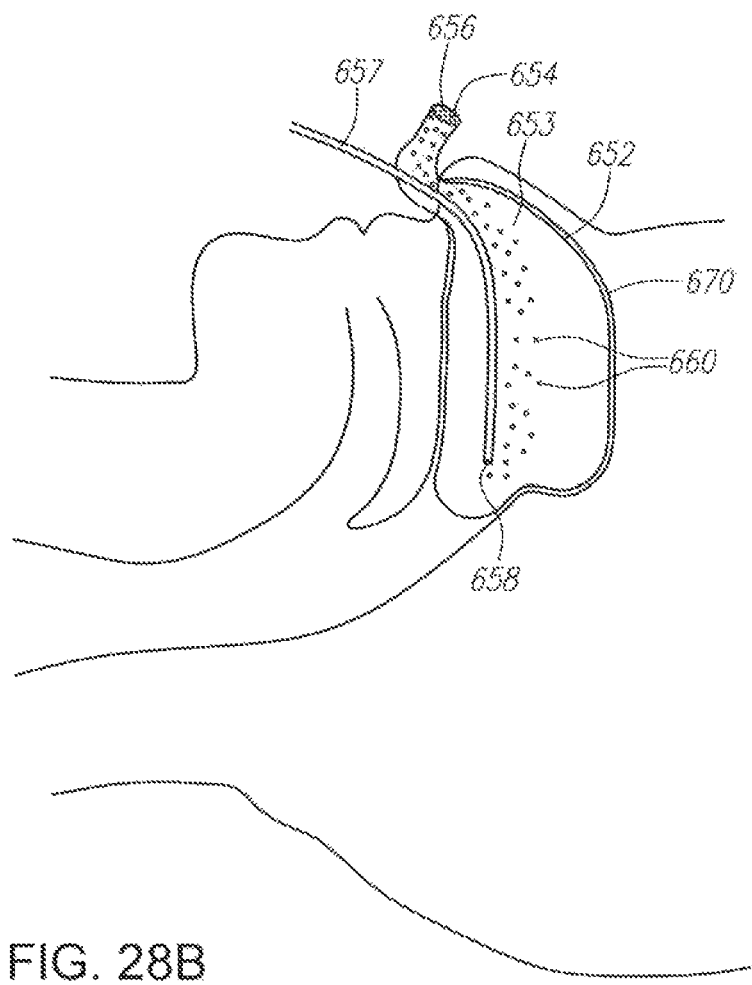
FIG. 28B illustrates the device of FIG. 28A inserted into a nasal cavity.

In an alternative embodiment, a flexible balloon having a chamber filled with a cooling liquid and a cold finger can be used to cool the brain via the nasal cavity. As seen in FIG. 28A, assembly 650 includes flexible balloon 652 that has chamber 653 that is in fluid communication with port 654 containing a filter 656. A cooling liquid, such as water or saline, can be infused into chamber 653 through lumen 658 of elongate tubular member 659. A cooling agent, such as Freon or other PFC, that is approximately 0° C., alternatively approximately −1° C., alternatively approximately −2° C., alternatively approximately −3° C., alternatively between about −5° C. and 5° C., alternatively between about −5° C. and 0° C., will be flowed through cold probe 657. Additionally, cold probe 657 may be connected to cooler (not shown). The cooling agent will flow out of port 658 of cold probe 657 and produce gas bubbles 660 in the cooling liquid in chamber 653, thereby cooling the liquid further and agitating the liquid to aid in mixing the liquid throughout chamber 653. The gas bubbles can exit chamber 653 through port 654 with air venting film 656, which allows for the release of gas and not liquid. Additionally, an additional elongate tubular member (not shown) can be inserted into flexible balloon 652 such that a lumen of the elongate tubular member is in fluid communication with chamber 653 of balloon 652. An additional gas, such as oxygen or nitrogen, can be delivered into the cooling liquid to aid in the mixing and agitation of the cooling liquid within the chamber.

In use, with the patient lying on his back, assembly 650 is inserted into the nasal cavity through the patient's nostril such that flexible balloon 652 is within nasal cavity 670. A cooling fluid can then be used to inflate flexible balloon 652 to a sufficient pressure such that flexible balloon 652 expands and is in contact with a substantial portion of nasal cavity 670. The cooling agent will flow out of port 658 of cold probe 657 and produce gas bubbles 660 in the cooling liquid in chamber 653, thereby cooling the liquid further and agitating the liquid to aid in mixing the liquid throughout chamber 653. The gas bubbles can exit chamber 653 through port 654 with air venting filter 656, which allows for the release of gas and not liquid. Additionally, the fluid in the balloon can be agitated to prevent freezing. This may be accomplished by moving cold probe 657 or pulsing the infusion of the cooling agent into chamber 653. Additionally, a second assembly can also be inserted into the other nostril such that maximum cooling can be obtained. The cooling of the brain would occur by convection or heat exchange from the cold liquid in the balloon to the warm nasal cavity.

Figure 30:
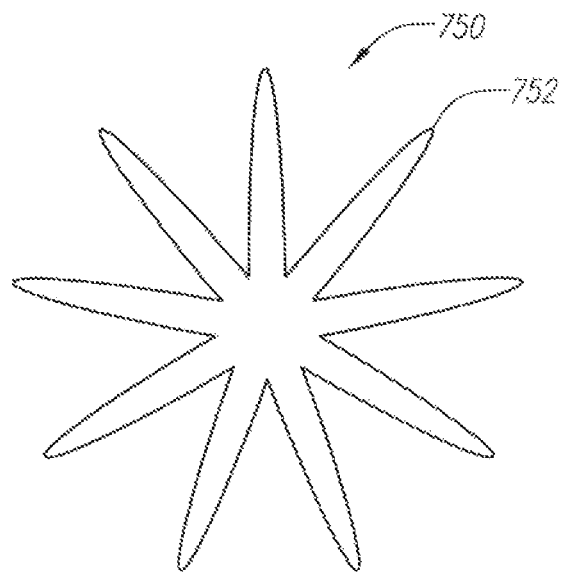
FIG. 30 illustrates an alternative balloon shape.

Flexible balloons for use in the nasal cavity are sized such that upon inflation, they are capable of making good contact with the surfaces of the nasal cavity, including the portion of the cavity that lies posterior to the cavernous sinus. In one embodiment, the length of the flexible balloon will depend upon the size of the nasal cavity and may be less than 15 cm long, alternatively less than 14 cm long, alternatively less than 13 cm long, alternatively less than 12 cm long, alternatively less than 11 cm long, alternatively less than 10 cm long, alternatively less than 0 cm long, alternatively less than 8 cm long. The flexible balloons may also have the shape of the nasal cavity. Alternatively, as seen in FIG. 30, flexible balloon 750 may have a shape containing multiple fingers such that, upon inflation, one or more fingers will have the opportunity to extend into and fill the meatus (superior, middle, and/or inferior) to maximize contact with the tissues in the nasal cavity. Alternatively, the flexible balloon may have multiple lobes to accomplish the same purpose of extending into and filling the meatus. The flexible balloons are also preferably oversized and made of a soft, conformable, elastomeric material to provide maximum surface contact with the nasal cavity. The assemblies may also include a cheek valve (not shown) that will release fluid, thereby reducing the pressure of the flexible baboons when they reach a certain pressure. Optionally, the flexible balloons may be made of a porous material that allows for the controlled release of drugs to the nasal cavity. Examples of materials for the elastomeric, flexible balloons include, but are not limited to, urethanes, vinyl (PVC), silicone. Examples of non-elastic materials include, but are not limited to, mylar, polyethylene, polypropylene, polystyrene, and polyvinylacetate.

In use, the pressure in these flexible balloons for use in the nasal cavity can oscillate between lower and higher pressures. In other words, the fluid can be infused to fill the chamber defined by the balloon either slowly or quickly. When expanded at higher pressures, presumably more heat transfer will occur due to increased contact with the nasal cavity. Extended periods at higher pressures, however, may not be desirable due to possible problems wish stopping blood flow in the surrounding tissue. Additionally, the act of pulsing the liquid would result in increased circulation of the liquid. Rapid pulsing, for the purposes of mixing the liquid within the balloon chamber, could range from about 0.5 to about 200 Hz, alternatively from about 1 to about 150 Hz, alternatively from about 1 to about 100 Hz, alternatively from about 10 to about 100 Hz, alternatively from about 25 to about 100 Hz. Slower pulsing could be used to effect physiologic responses, such as deflating the balloon to a allow blood flow to resume circulation in the cooled area. Slower pulsing could range from about one inflation per second to about one inflation per 10 minutes, alternatively from about one inflation per second to about one inflation per 5 minutes, alternatively from about one inflation per second to about one inflation per 3 minutes. Alternatively, the balloon could be inflated approximately once every 30 seconds, alternatively once every 1 minute, alternatively once every 2 minutes, alternatively once every 3 minutes, alternatively once every 4 minutes, alternatively once every 5 minutes, alternatively once every 6 minutes, alternatively once every 7 minutes, alternatively once every 8 minutes, alternatively once every 9 minutes, alternatively once every 10 minutes. During these slower cycling periods, the balloon could remain inflated for approximately 1% of the cycling period, alternatively approximately 5% of the cycling period, alternatively approximately 10% of the cycling period, alternatively approximately 20% of the cycling period, alternatively approximately 30% of the cycling period, alternatively approximately 40% of the cycling period, alternatively approximately 50% of the cycling period.

The cooling fluid used to fill the flexible balloons may include, but is not limited to, water, refrigerant, saline, PFC, anti-freeze solution, or a combination thereof.

In an alternative embodiment, the chambers of the flexible balloons may be filled with foam, e.g., open cell foam. Alternatively, the foam, e.g., open-cell foam may be surrounded by a membrane. In either embodiment, the open-cell foam will aid in conforming the balloon to the applicable cavity, for example, the nasal cavity, while also helping to distribute cooling. The foam may be made from urethane, latex, rubber, ethylene vinyl acetate (EVA), and other open-cell materials.

In use, before insertion into the body cavity, the foam that is contained either within the flexible balloon or the membrane will be compacted using a vacuum source. After the compacted foam has been inserted into the desired body cavity, e.g., the nasal cavity, the vacuum will be released and the balloon will be allowed to expand to contact the surrounding tissue. Saline, water, PFC, refrigerant, anti-freeze solution, other cooling fluid, or a combination thereof can then be circulated into the open-cell foam to cool the surrounding tissue.

Cooling Calculations

The following calculations estimate the maximum cooling that can be obtained when a chilled liquid is circulated through the nasal cavity, where the chilled fluid is either directly in contact with the nasal tissues or contained in a flexible membrane 'balloon' within the nose.

A cooling liquid is circulated into and out of the nasal cavity. The following calculations are done assuming that the chilled fluid will be an aqueous fluid. The following are properties of water:

Density: 1 gram/ml

Heat capacity: 1 cal/gram-° C.

The liquid will enter the nasal cavity at a temperature well below body temperature, and exit at a warmer temperature. The warming of the water will be equal to the cooling of the body, so the calculations for heat added to the water is the same as that for heat removed from the body.

$$Q'c*m*(T2-T1) \text{ or } Q'=cm\Delta T$$

$Q'$=the rate of heart transfer $m$=the mass flow rate of the liquid administered $c$=the heat capacity of the liquid $T1$=the temperature of the liquid at administration T2=the temperature to which the liquid is warmed If the flow rate is 500 ml/min, inlet temperature is 2° C., outlet temperature is 4° C.

Heat Transfer=500 ml/min*1 g/ml*1 cal/gm° C.*(4° C.−2° C.)=1000 cal/min

Conversion factors: 1 calorie/minute=0.069 78 watt 1000 cal/min*0.06978 Watt/cal/min=70 Watts The cooling of the whole body can be calculated using the same equation as above. The heat capacity of the human body is generally accepted to be 0.85 cal/gm° C. For this calculation, other sources of heat entering or leaving the body, and heat generated in the body are neglected, as it is likely those aspects balance out in a stable patient. Cooling therefore reduces to the equation below.

Whole body cooling($\Delta T$)=Heat removed/(mass*heat capacity)

Continuing the example above, for a 75 kg patient, the temperature change is calculated below to be 0.93° C. per hour, which is close to the target cooling rate for patients.

$$\text{Temperature change} = 100 \text{ cal/min}/(75{,}000 \text{ grams} * 0.85 \text{ cal/gram } °\text{C.}$$

$$= 0.0157° \text{ C./min}$$

$$= 0.93° \text{ C. per hour}$$

For the whole body cooling (WBC), the following formula can be developed from the above:

WBC (° C./hr)=$\Delta T$(liquid,° C.)*Flow rate(ml/min)/ (Patient wt (kg)*14.3)

or

WBC (° C./hr)=Cooling(watts)/Patient Weight (kg)

The surface of the balloon may be treated or modified to maximize thermal conductance. A gel may also be optionally applied to the exterior of flexible balloons 204, 254 before insertion into the nasal cavity. The gel would preferably have good thermal conduction properties and be a better conductor than air. Additionally, the gel could also act as a lubricant to assist in the insertion. The gel would help the flexible balloon make better contact with the mucous membrane and would also fill some of the air space in the nasal cavity, which should increase effective surface area. The gel may include, but is not limited to, any aqueous gel, a poloxamer-based gel, a cellulose gel (such as KY jelly), a nasal-packing jelly, a hydrogel (such as MecroGel or Gel-Film), or a thermal gel. Alternatively, sponges may be attached to the surface of the balloon. Sponges, such as PVA sponges, are commonly used as packing material in noses and will conform to the shapes of the nasal cavity when wet. Alternatively, a hydrophilic coating may also be applied to the outer surface of the balloon to prevent beading on the outside.

Advantages of this apparatus and method include rapid circulation of the cooling fluid, rapid transfer of heat from the flexible balloon to the membranes of the nasal cavity, and flexibility in choice of coolant because the fluid is contained. Heat is transferred through the mucosa from the pool of blood in the cavernous sinus to the cooling fluid in the flexible balloon, thereby cooling the pool of blood in the cavernous sinus. Consequently, the blood in the carotid arteries, which runs through the cavernous sinus, is also cooled as it travels to the brain. In particular, the maximal heat exchange will likely be with the ascending carotid arteries immediately before entry into the intracranial space and the terminal portion of the extracranial internal carotid artery.

Figure 49:
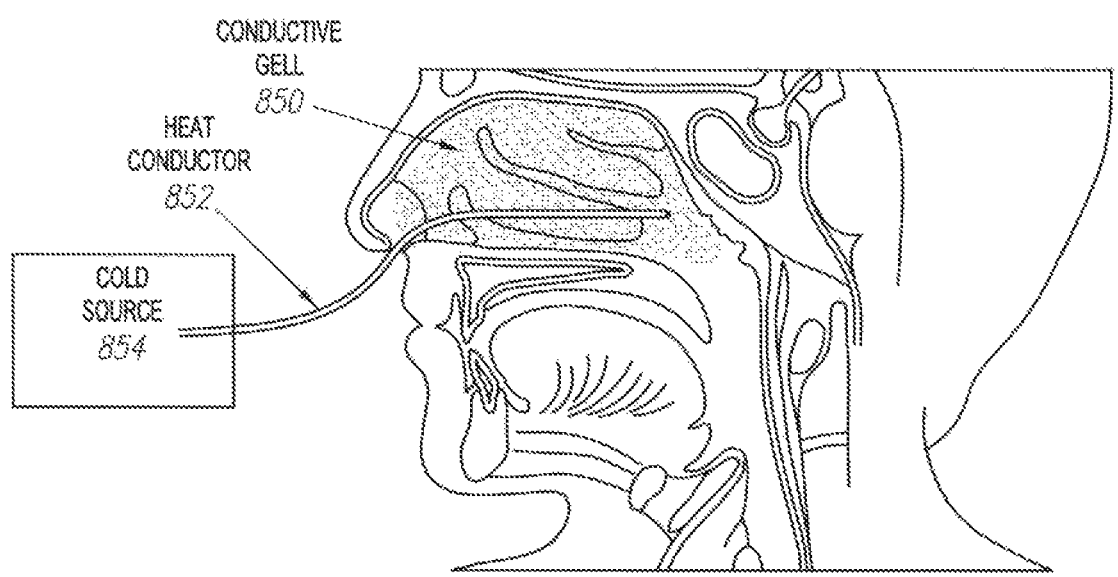
FIG. 49 illustrates the use of a conductive gel with a device having proximal and distal expandable members constructed according to the present invention for non-invasive cerebral and systemic cooling via the nasal cavity.
Figure 50:
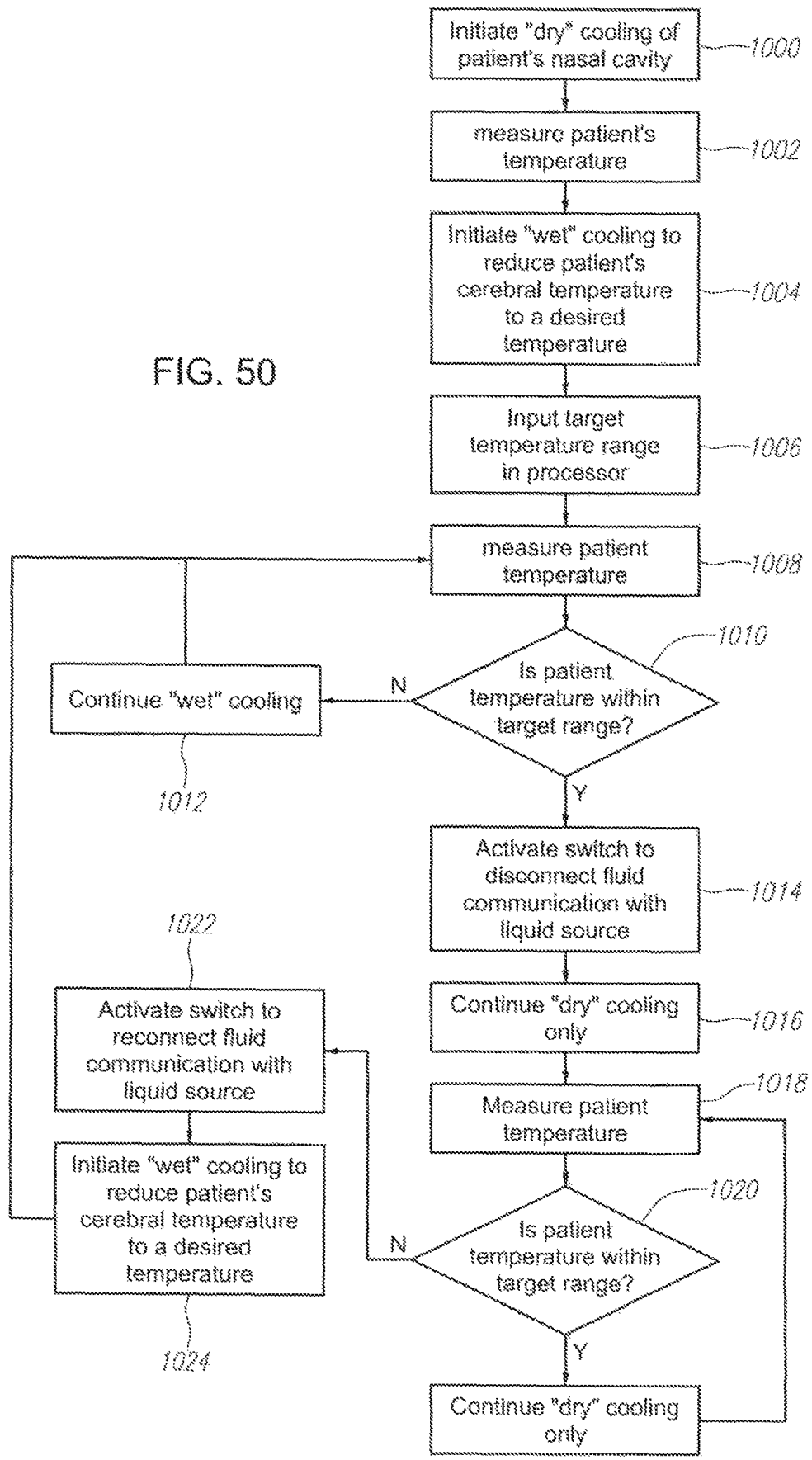
FIG. 50 a flow chart illustrating a computerized method for controlling a cooling device to maintain a patient's temperature at a desired level.

In another aspect of the invention, as seen in FIG. 49, thermoconducting gel 850 may be inserted into the nasal cavity of a patient to substantially fill the cavity. Cooling device 852, such as a cold probe or heat pipe, can then be directly inserted into gel 852 to cool gel 852, thereby cooling the nasal cavity. The conductive device could be a metal, such as copper. Alternatively, conductive device 852 may be a probe through which a chilled fluid is circulated, a probe in which a fluid undergoes a phase change, or a heat pipe, which is a sealed system utilizing an internal fluid that boils on one end and condenses on the other end in order to transmit heat. In the case of the probe with the fluid undergoing a phase change, the fluid may have a boiling point below body temperature, such as a perfluorocarbon or Freon. Additionally, external cooling source 854, such as a refrigeration system, thermoelectric heat pump, ice bath, or evaporative cooler, will be connected to the proximal end of the probe. Consequently, a cerebral temperature of the patient can be reduced by at least 1° C. in one hour, alternatively at least 2° C. in one hour, at least 3° C. in one hour.

In another aspect of the invention, a sponge may be inserted into the nasal cavity of a patient to substantially fill the cavity. As mentioned previously, the sponge could surround the outside of a balloon to help fill the nasal cavity. The sponges may help to fill the back of the mouth and come into intimate contact with the soft palate and upper pharynx. Alternatively, the sponge could be inserted into the nasal cavity alone. The sponge could be connected to an inlet and outlet tubular member to allow for circulation of fluids within the sponge. In contrast to the balloon, the increased surface area of the sponge would allow for better contact with the interior surfaces of the nasal cavity. Additionally, the sponges could be designed with finer or hair-like extrusions to increase the surface area, thereby increasing contact with the interior surfaces of the nasal cavity. A hollow tube could be inserted through the sponge and/or balloon to facilitate breathing.

Convective Cooling in Other Parts of the Body

Figure 24:
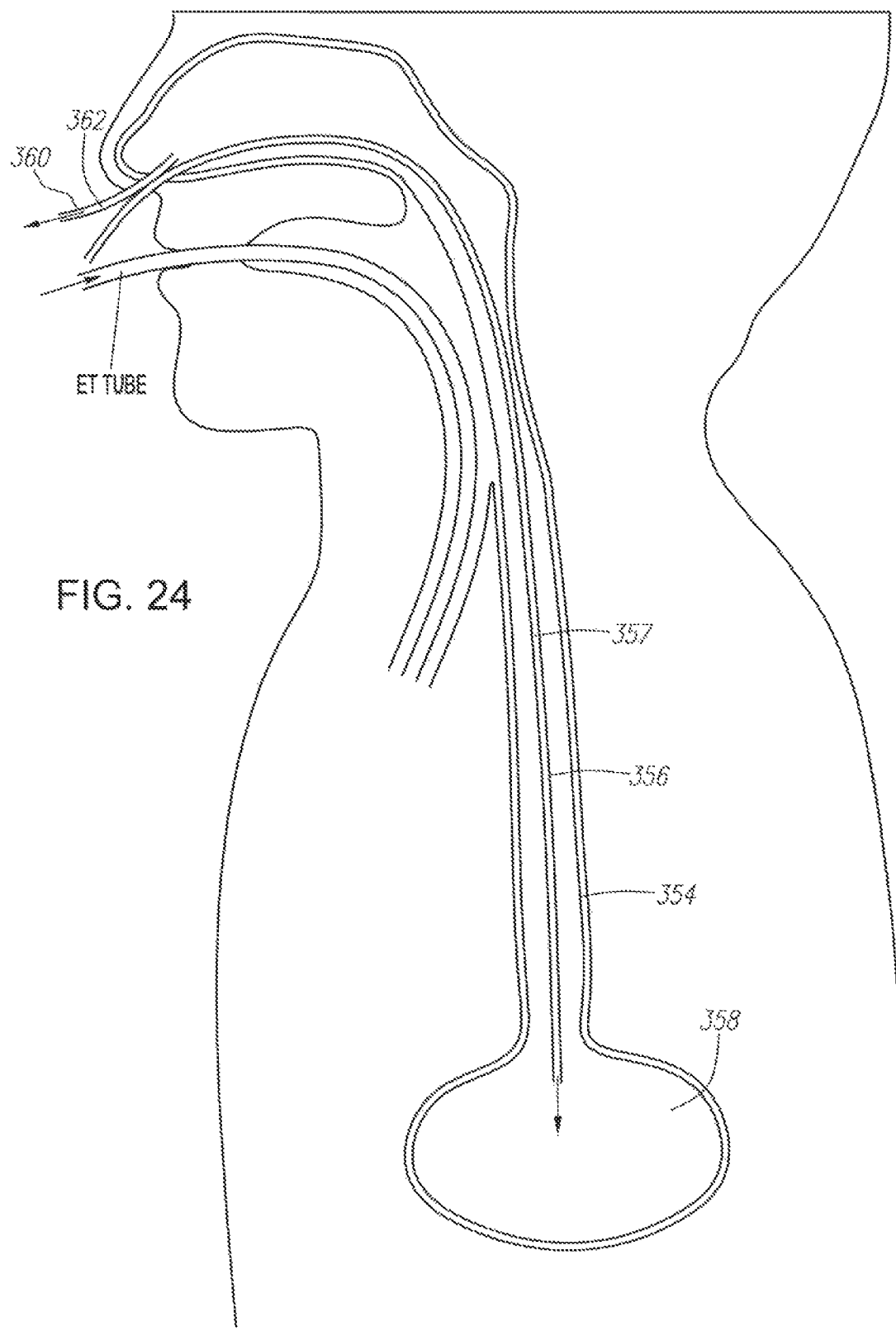
FIG. 24 illustrates an embodiment of a device having a flexible balloon mounted on an elongate tubular member inserted down the esophagus.

In another aspect of this invention, a modified nasogastric tube with a flexible balloon having a chamber filled with a cooling liquid may be used to cool the brain. As seen in FIG. 24, the assembly includes nasogastric tuber 356 having lumen 357, flexible balloon 354 that is mounted circumferentially around nasogastric tube 356 for the length of the esophagus, and elongate tubular member 360 having lumen 362. Nasogastric tube 356 is approximately 0.8 m in length, alternatively approximately 1 m in length, alternatively approximately 1.2 m in length, alternatively approximately 1.4 m in length, alternatively approximately 1.6 m in length, alternatively approximately 1.8 m in length, alternatively between 0.8 m and 1.8 m in length. An additional flexible balloon 358 may be attached at the distal end of the nasogastric tube 356. Flexible balloon 358 would be in fluid communication with lumen 357 of nasogastric tube 356 and a chamber of flexible balloon 354 and, upon expansion, would be sized to substantially fill the patient's stomach. Alternatively, at its distal end, flexible balloon 354 may be sized and shaped to substantially fill the patient's stomach upon expansion. At their proximal ends, elongate tubular member 360 and nasogastric tube 356 are connected to a pump and a cooler (not shown) or a refrigerated pump (not shown) that is capable of infusing and/or recycling a cooling fluid through flexible balloons 354, 358. Flexible balloons 354, 358 are sized that upon inflation, they are capable of making good contact with the surfaces of the adjacent anatomy, e.g., nasal cavity, esophagus, or stomach. Flexible balloons 354, 358 are also preferably oversized and made of a soft, conformable, elastomeric material to provide maximum surface contact with the anatomy in which they are positioned. Flexible balloons 354, 358 may also include a check valve (not shown) that will release fluid, thereby reducing pressure of flexible balloons 354, 358 when they reach a certain pressure. Optionally, all or a portion of flexible balloons 354, 358 may be made of a porous material that allows for the controlled release of drugs.

In use, the patient is intubated and the assembly is inserted through a patient's nostril, down the back of the throat, through the esophagus, and into the stomach. The assembly is positioned such that flexible balloon 354 is located in the nasal cavity and the esophagus and flexible balloon 358 is located in the stomach. A cooling fluid can then be infused into flexible balloons 354, 358 to expand the balloons such that they substantially fill and contact the nasal cavity, esophagus, and stomach, respectively. The cooling fluid could be pumped in through nasogastric tube 354 and suctioned out of elongate tubular member 360 at a rate sufficient to induce or maintain a desired pressure in the flexible balloons 354, 358 or a desired brain temperature. The cooling fluid may then be recirculated through flexible balloons 354, 358 via nasogastric tube 356, shaft 360, and a refrigerated pump (not shown).

Figure 25A:
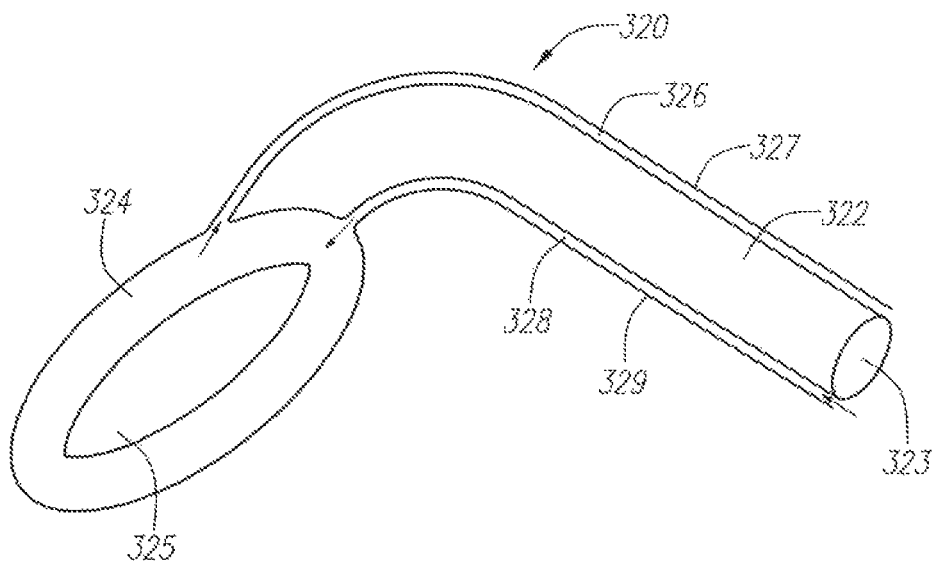
FIG. 25A illustrates a modified laryngeal mask.
Figure 25B:
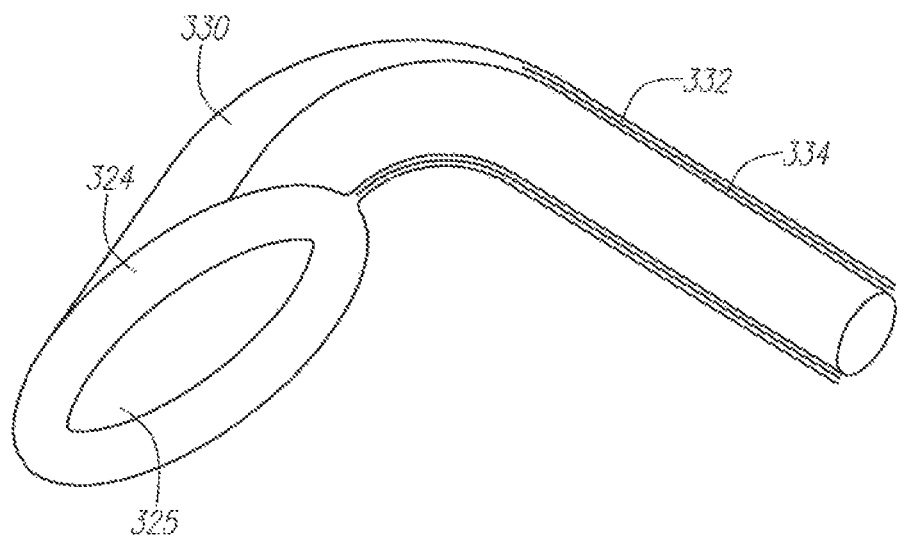
FIG. 25B illustrates an alternative embodiment of a modified laryngeal mask.

In another aspect of this invention, a modified laryngeal mask having a flexible balloon having a chamber filled with a cooling liquid can be used to cool the brain. As seen in FIG. 25A, the laryngeal mask 320 includes an elongate tubular member 322 having a proximal end, a distal end, and lumen 323 therebetween that communicates with ports at the proximal and distal ends. The elongate tubular member 322 is preferably curved to match the anatomy of the oropharynx. Toroidal balloon 324 has a chamber, and surrounds port 325 at the distal end of elongate tubular member 322, wherein the chamber is in fluid communication with lumens 326, 328 of elongate tubular members 327, 329. Alternatively, lumens 326, 328 may be part of elongate tubular member 322. Elongate tubular members 327, 329 are also connected to a pump and cooling unit (not shown) or a refrigerated pump (not shown) that is capable of infusing and/or recycling a cooling fluid through flexible toroidal balloon 324. The cooling fluid may include, but is not limited to, water, saline, PFC, anti-freeze solution, or a combination thereof. As seen in FIG. 25B, the modified laryngeal mask may also include an additional balloon 330 that is located on the distal region of the backside of elongate tubular member 322, wherein a chamber of additional balloon 330 is in fluid communication with lumens 332, 334. Lumens 332, 334 may be part of elongate tubular member 322 or part of separate elongate tubular members. Additionally, the chamber of additional balloon 330 may alternatively be in fluid communication with lumens 326, 328 (not shown). Lumens 332, 334 would also be connected to a pump and cooling unit (not shown) or a refrigerated pump (not shown) that is capable of recycling the cooling fluid through flexible balloon 330.

Figure 25C:
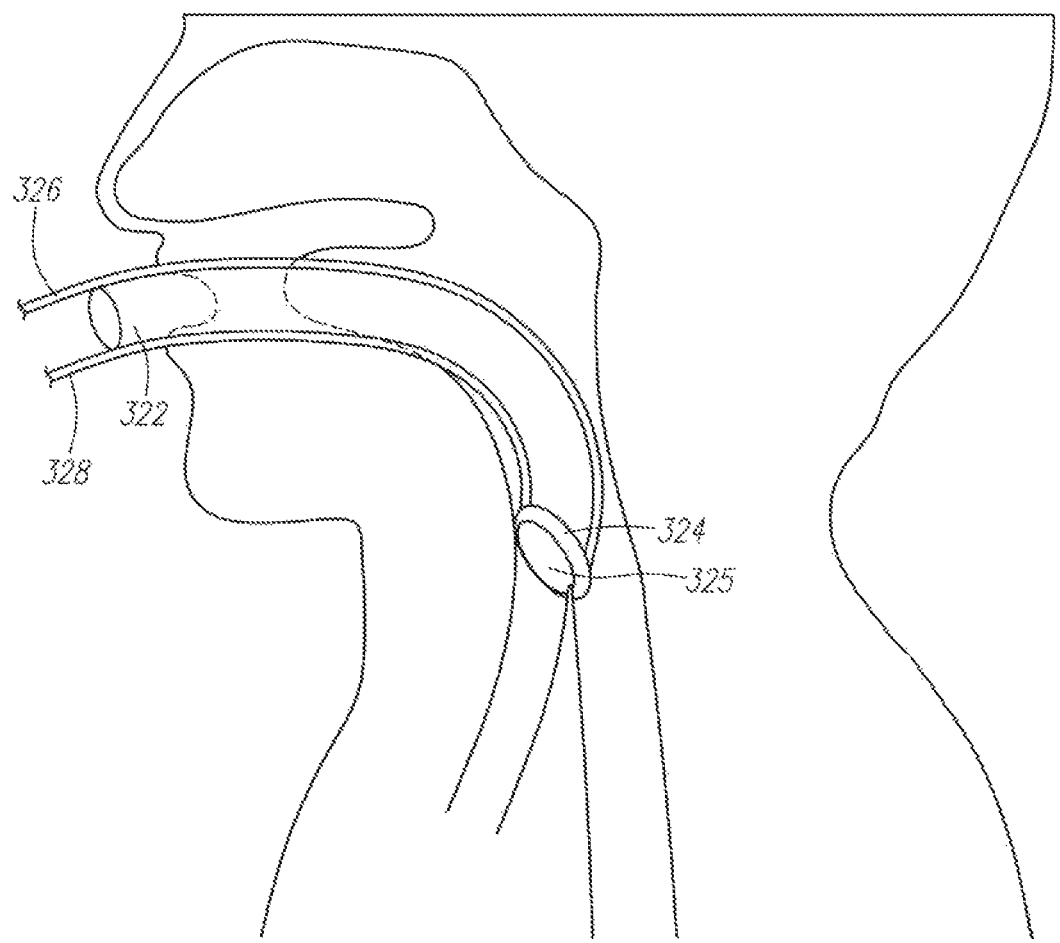
FIG. 25C illustrates use of the device of FIG. 25A.

In use, as seen in FIG. 25C, the modified laryngeal mask 320 is positioned in the patient to sit tightly over the larynx. Toroidal balloon 324 is emptied before insertion and lubricated with a gel. In addition to being a good lubricant, the gel would also preferably have good thermal conduction properties and be a better conductor than air. The gel may include, but is not limited to, a poloxomer-based gel (such as KY jelly) or a packing jelly. The neck of the patient is extended and the mouth is opened widely. The apex of the laryngeal mask 320, with the port or opening 325 pointing downwards toward the tongue, is pushed backwards toward the uvula. Elongate tubular member 322 follows the natural bend of the oropharynx and the mask comes to rest over the puriform fossa. A cooling fluid can then be used to infuse and/or inflate toroidal balloon 324 to a sufficient pressure such that toroidal balloon 324 sits tightly over the larynx and is in contact with the epiglottis. The cooling fluid may then be recirculated through toroidal balloon 324 via lumens 326, 328, cooler (not shown), and pump (not shown). Additionally, the cooling fluid can be withdrawn or suctioned out of toroidal balloon 324 at a rate sufficient to induce or maintain a desired balloon pressure or brain temperature. During the cooling process, the airway is protected by the elongate tubular member 322.

Figure 26:
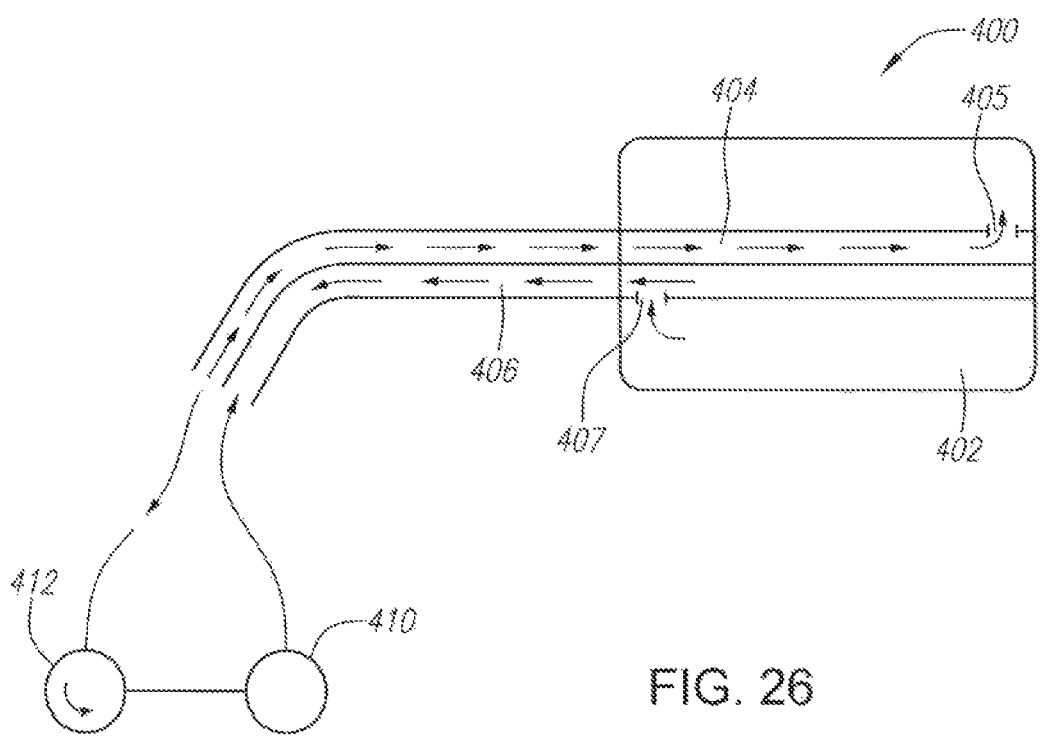
FIG. 26 illustrates an embodiment of a flexible balloon device for insertion into the oral cavity.

In another aspect of this invention, a cooling pad may be used to cool the brain via the oral cavity. As seen in FIG. 26, the assembly 400 includes a flexible balloon or pad 402 having a chamber, tubular member 403, 405 having lumens 404, 406 and ports 405, 407, wherein the chamber is in fluid communication with port 405, 407 and lumber 404, 406. At their proximal ends, tubular members 403, 405 are connected to cooler 410 and pump 412. Alternatively, tubular members 403, 405 may be connected to a refrigerated pump (not shown) that is capable of infusing and/or recirculating cooling fluid. The pad may be about 2.5 cm in length, alternatively about 3 cm in length, alternatively about 3.5 cm in length.

In use, the assembly 400 is inserted into the oral cavity through the mouth such that the flexible balloon or pad 402 covers the retromandibular area or peritonsillar region. A cooling fluid can then be infused into the chamber of flexible balloon or pad 402 to expand it to a sufficient pressure such that flexible balloon or pad 402 is substantially in contact with the retromandibular area or peritonsillar region. The cooling fluid may then be recirculated through flexible balloon 402 via lumens 404, 406, using pump 412 and cooler 410 or a refrigerated pump. The cooling fluid can also be withdrawn or suctioned out of the flexible balloon 402 at a rate sufficient to induce or maintain a desired balloon pressure or brain temperature. Cooling of the brain may be achieved through convection or heat transfer between flexible balloon or pad 402 and the extracranial carotid artery.

The cooling fluid used with these inventions may include, but is not limited to, water, saline, PFC, anti-freeze solution, or a combination thereof. The temperature of the cooling fluid will preferably be below body temperature. The temperature of the cooling fluid may be between about 37° C. to about −20° C., alternatively between about 30° C. to about −20° C., alternatively between about 20° C. to about −20° C., alternatively about 0° C., alternatively about 5° C., alternatively between about −5° C., alternatively between about −5° C. to about 10° C., alternatively between about −5° C., to about 5° C., alternatively between about 0° C. to about 5° C. When saline is used as the cooling fluid, the saline will preferably be about 0° C. The cooling fluid should recirculate at a fast enough rate to maintain the low temperatures within the balloon. The flow rate of the cooling liquid may be between about 5 and about 5 L/min, alternatively between about 100 and about 400 ml/min, alternatively between about 200 and about 300 ml/min, alternatively between about 150 to about 200 ml/min.

Optionally, a gel may also be optionally applied to the exterior of flexible balloons before insertion into the oral cavity. The gel would preferably have good thermal conduction properties and be a better conductor than air. Additionally, the gel could also act as a lubricant to assist in the insertion. The gel may include, but is not limited to, any aqueous gel, a poloxamer-based gel, a cellulose gel (such as KY jelly), a nasal-packing jelly, or a thermal gel. Alternatively, sponges may be attached to the surface of the balloon. Sponges, such as PVA sponges may be attached to the material and will conform to the shapes of the oral cavity when wet. The sponges could be designed with finger or hair-like extrusions to increase the surface area, thereby increasing contact with the interior surfaces of the oral cavity. The sponges may fill the back of the mouth and allow for maximal cooling at the soft palate and retropharynx. Alternatively, a hydrophilic coating may also be applied to the outer surface of the balloon to prevent beading on the outside. A tube may also be inserted to allow breathing.

Fluid/Gas Delivery Systems

Figure 31:
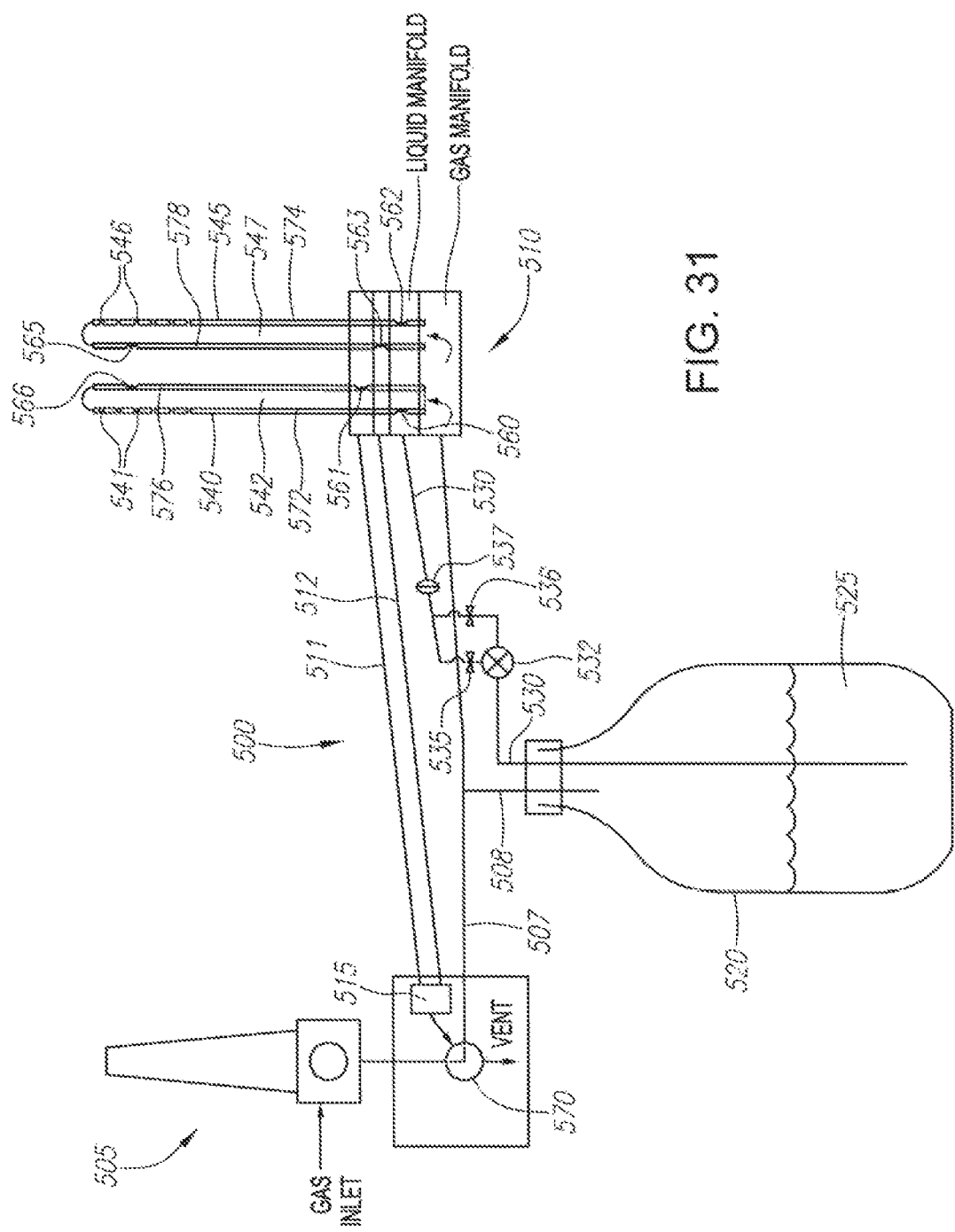
FIG. 31 illustrates a fluid and gas delivery system.
Figure 32A:
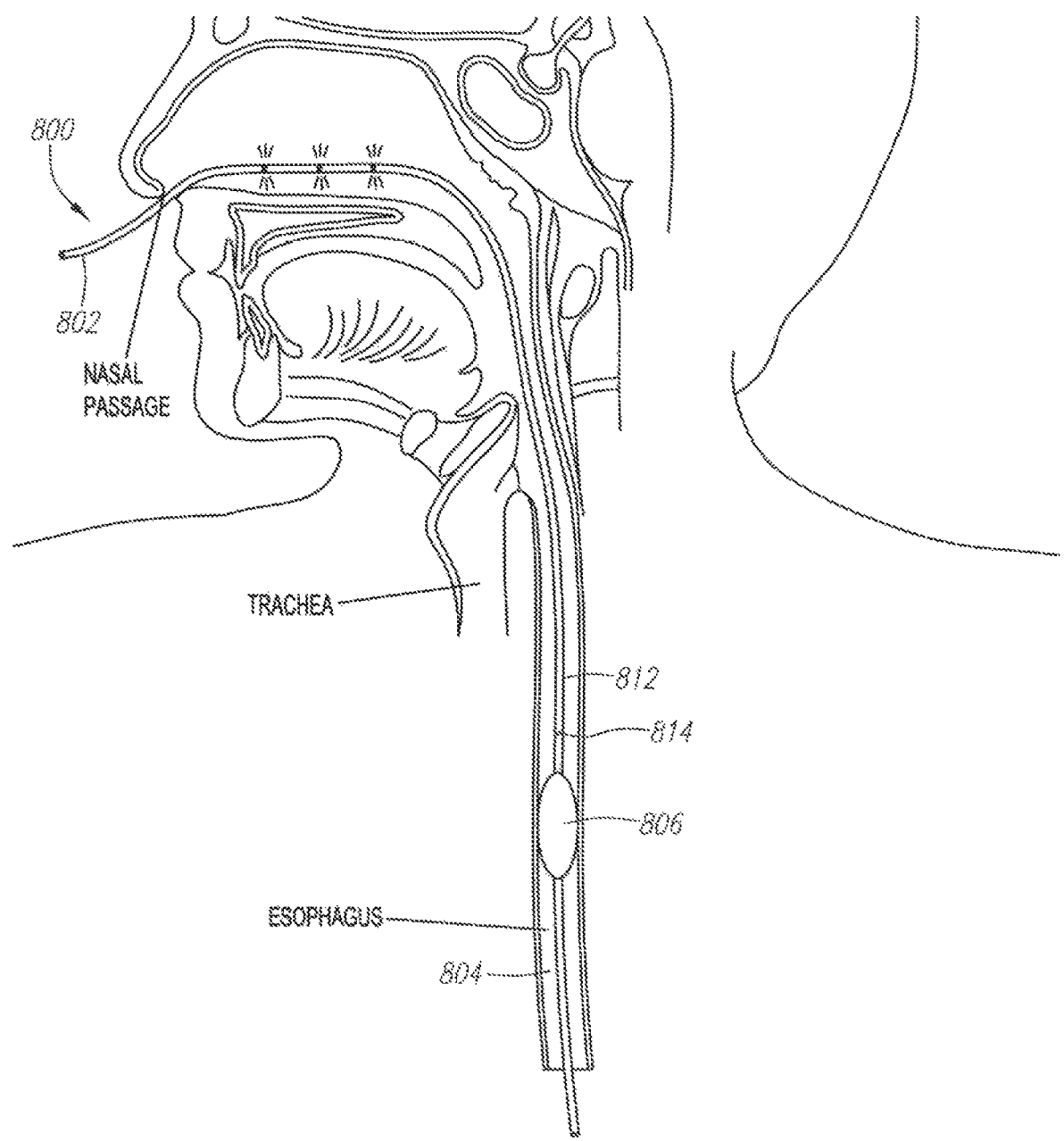
FIG. 32A illustrates an embodiment of a device having an expandable member constructed according to the present invention for non-invasive cerebral and systemic cooling.
Figure 32B:
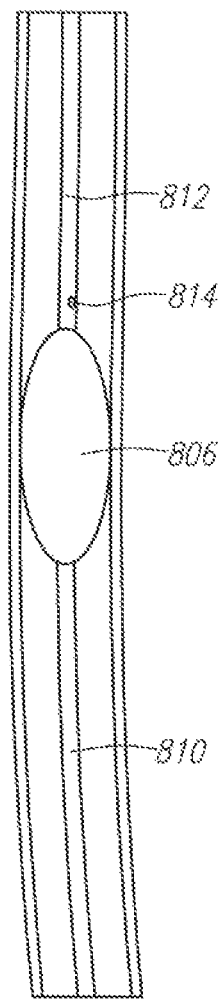
FIG. 32B illustrates an embodiment of a device having an esophageal suction tube constructed according to the present invention.
Figure 33:
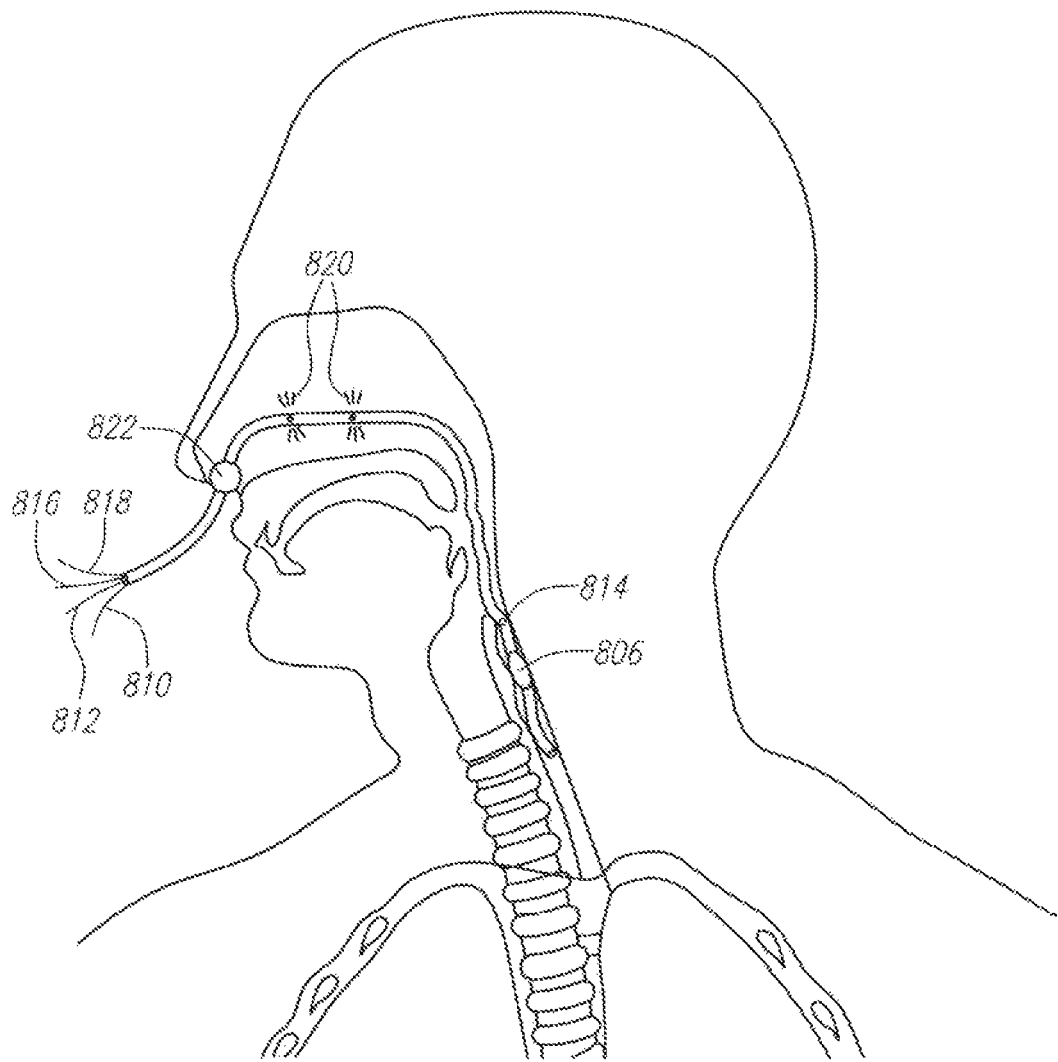
FIG. 33 illustrates an embodiment of a device having an esophageal suction tube and a gastric suction tube constructed according to the present invention.
Figure 34:
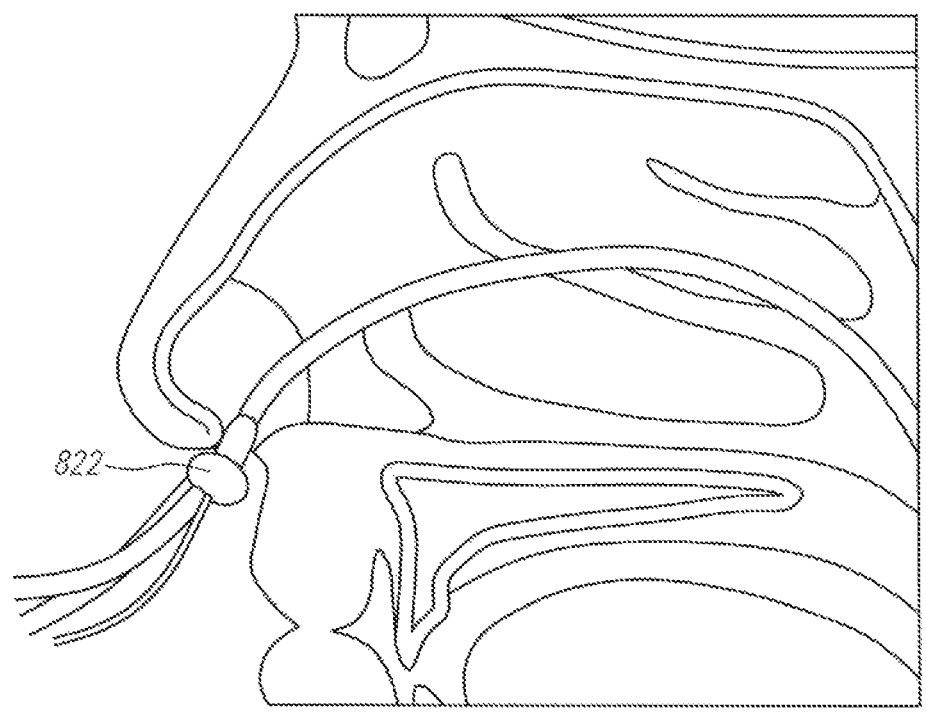
FIG. 34 illustrates an embodiment of a device having a nasal plug constructed according to the present invention.
Figure 35:
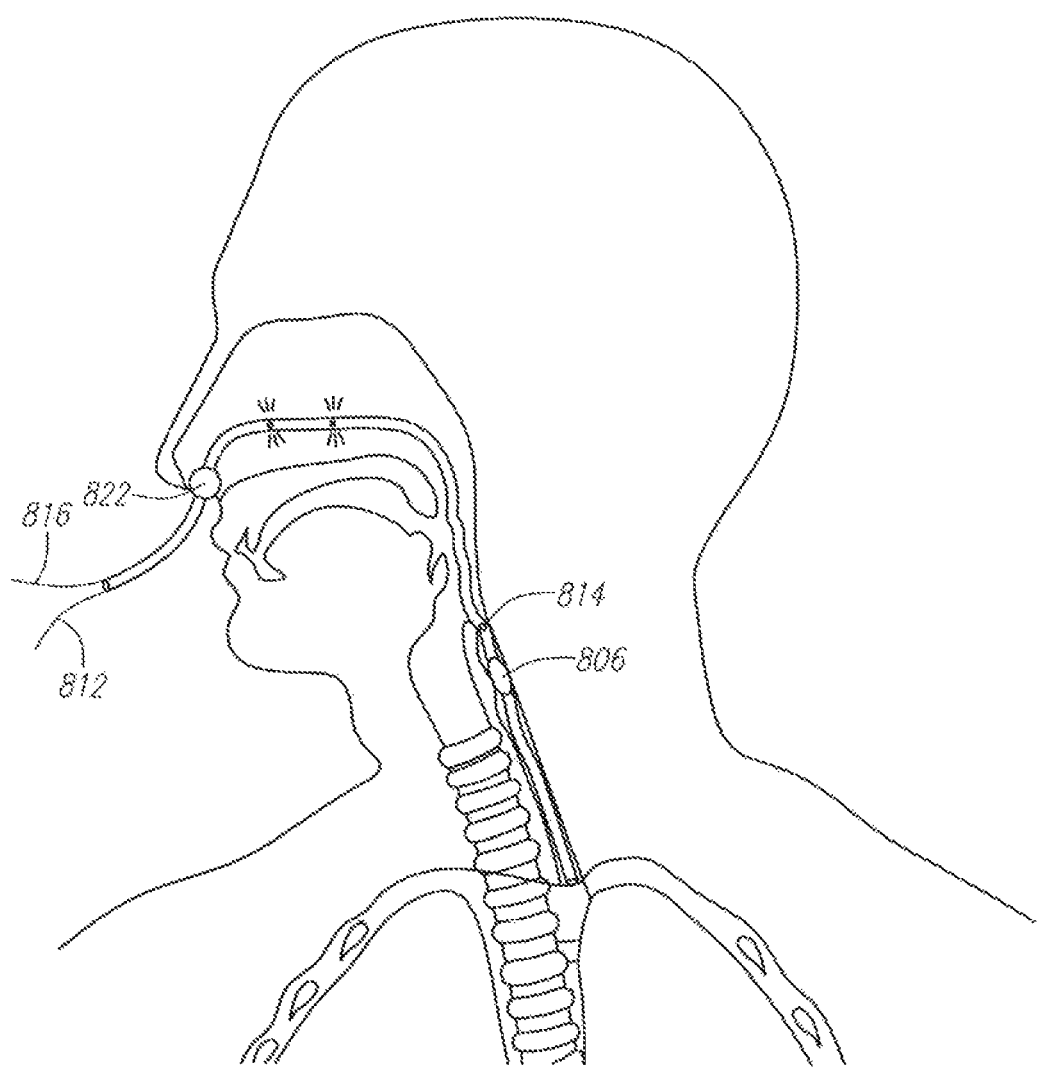
FIG. 35 illustrates an alternative embodiment of a device having an expandable member constructed according to the present invention for non-invasive cerebral and systemic cooling.

In another embodiment, the invention includes a liquid and gas delivery system for the delivery of a fixed, or substantially fixed, ratio of liquid and gas. As seen in FIG. 31, in delivery system 500, gas flow meter 505 can be set to deliver to set flow of gas to mixing hub or manifold 510 through gas line 507. As gas is delivered to manifold 510, gas will also flow to bottle 520 through gas line 508. Gas lines 507 and 508 may also comprise a single branched tube (not shown). As reservoir or bottle 520 becomes pressurized, liquid 525 in bottle 520 will flow through line 530 to manifold 510. The flow of the liquid will directly depend on the pressure of the gas being delivered from flow meter 505—i.e., higher gas pressure will result in a faster flow of liquid. Therefore, a fixed ration of liquid and gas can be delivered to the manifold. As the flow rate of the gas is increased, a proportional increase in the liquid flow rate occurs, such that the ratio of liquid to gas being delivered to mixing manifold 510 is maintained without having to independently adjust the flow of the liquid. Flow restrictors 535 and 536 can be set to each allow a specific flow of liquid for a specific pressure of gas. For example, flow restrictor 535 may allow a higher flow rate than flow restrictor 536 for a specific pressure of gas. Stopcock 532 can be connected to line 530. Stopcock 532 is used to direct flow either to restrictor 535 or 536 or can be used to stop liquid flow altogether. Filter 537 can also be placed in line 530 before mixing manifold 510. An overpressure safety device 515 within gas flow meter 505 can stop the flow of gas if a certain pressure is detected. Activation of the overpressure safety device 515 would switch valve 570 to stop gas flow and vent gas lines 507 and 508. Therefore, the pressure in gas lines 507 and 508 and bottle 520 will all be reduced to zero. Therefore, the flow of liquid will also be stopped by the activation of safety device 515. The gas could be air, oxygen, or a combination thereof. The liquid could include a perfluorocarbon such as perfluorohexane, perfluoropentane, or 2-methyl-perfluoropentane.

Mixing manifold 510 can be connected to catheters 540 and 545, each containing multiple delivery ports 541 and 546 for delivery of the gas and liquid mixture to, for instance, the nasal cavity. Liquid can flow from line 530 into liquid lumens 572 and 574 of catheters 540 and 545 through ports 560 and 562, respectively. Similarly, gas can flow from line 507 into lumens 542 and 547 of catheters 540 and 545 through ports in the distal ends of the respective catheters. The gas and liquid can later be mixed and delivered to the nasal cavity through the multiple ports 541 and 546 as a nebulized spray, as described above. Pressure in the nasal cavity can be measured through pressure lines 511 and 512, which are in communication with ports 565 and 566 located near the distal ends of catheters 540 and 545 through pressure lumens 576 and 578 and ports 561 and 563, respectively. Alternatively, a separate catheter could be inserted to measure the pressure in the nasal cavity (not shown). If a pressure measured in the nasal cavity in which the liquid and gas is being delivered is found to be too high, overpressure safety device 515 will stop the flow of gas, and consequently, the flow of liquid, to the nasal cavity. Additionally, the stopcock could be closed when it is desired to only deliver a gas, for instance, oxygen, rather than cool the patient.

Figure 45:
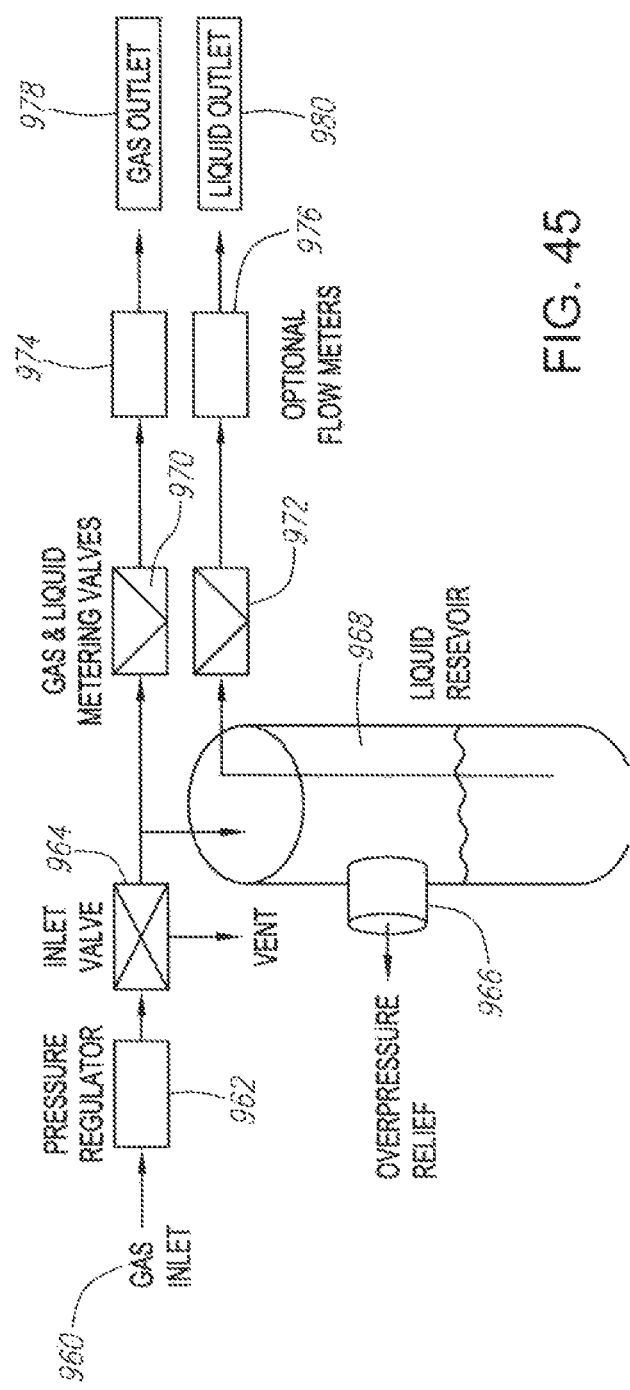
FIG. 45 illustrates a liquid delivery system for delivering the liquid to the point of administration constructed according to the present invention.

An alternative embodiment of the liquid and gas delivery system is depicted in FIG. 45. The mixing catheter may further include a liquid delivery system for using the pressure from the compressed gas source to deliver the liquid to the nasal catheter. In this device, both the gas and the liquid are delivered strictly using the pressure from the compressed gas source without the use of pumps or electronics. Here, inlet valve 964 is connected to compressed gas source 960, for example, oxygen or an oxygen and air mixture regulated to about 50 psi. Inlet valve 964 blocks or allows the pressurized gas into the rest of the system. When inlet valve 964 is in the "blocked" position, valve 964 also may vent pressure from the system. Pressure regulator 962 may also allow better control of the gas pressure delivered to the liquid delivery system and to the nasal catheter. When the inlet valve is in the "allow" position, the gas flow splits in two directions, i.e., flow is connected to the gas flow channel 978 of the dual lumen tubing (not shown) and flow is also directed to fluid reservoir container 968 that is designed to hold the desired dose of a liquid.

The fluid control reservoir 968 is rated to withstand the pressure of the compressed gas, for example the fluid control reservoir may be a poly ethylene terephalate (PET) container tested to pressures in excess of 150 psi. In addition, a burst disk or relief valve 966, set at a value exceeding the expected operating pressure, for example 60 psi, alternatively 70 psi, alternatively 80 psi, alternatively 90 psi, may be added to the fluid reservoir container as a safety means for venting gas in the event of over pressurization. When the pressurized gas flows into fluid reservoir 968, the fluid is routed through an outlet port in the reservoir that is in fluid communication with liquid channel 980 of the dual lumen tubing (not shown). The outlet port may include fluid flow controlling device 972, such as a needle type valve or a variable diameter aperture, to adjust the flow rate of fluid into liquid channel 980 of the dual lumen tubing. In addition, gas flow channel 978 of the dual lumen tubing may also include flow controlling device 970, such as a needle type valve or a variable diameter aperture, to adjust the flow rate of gas into the gas channel of the dual lumen tubing. The flow control valves 970 and 972 of the gas and liquid channels may be independently controlled by the operator to allow full flexibility in varying the gas and/or liquid flow to optimize the gas/liquid flow ration. The gas and liquid flow control valves 970 an 972 may have fixed orifices that produce a known constant flow for the gas and the liquid, or alternatively, the flow control valves 970 and 972 may include a selector (not shown) that would allow the operator to choose one of several sets of orifices in order to provide the operator with a number of choices for the flow, for example low flow, medium flow, high flow, induction, and maintenance flow rates. Here, each set point on the selector would use a predetermined orifice for the gas flow and a matched orifice for the liquid such that the gas/liquid flow rates and ratios would be optimized for each condition. In an alternative embodiment, the flow rate generated by the fixed orifices may be further altered while maintaining the constant gas/liquid ration, by using pressure regulator to regulate the input pressure of the gas source. In addition, liquid and gas flow meters 974 and 976 may be placed in the liquid and gas flow channels to further monitor and regulate the liquid and gas flow rates. Flow meters 974 and 976 may be any standard flow technology such as turbines, paddlewheels, variable area Rota meters or mass flow meters. In addition, in-line filters (not shown) may be placed in both the gas and liquid channels to prevent particulate matter from being introduced to the patient.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A medical device for cerebral cooling comprising:
   an elongate tubular member having proximal and distal ends, an outer wall having a plurality of delivery ports, and first and second lumens, the first and second lumens extending from a proximal region to the delivery ports and in communication with the plurality of delivery ports;
   a source of liquid coolant;
   a gas source in fluid communication with the first lumen; and
   a switch for alternately connecting the liquid coolant source to the second lumen,
   wherein the first lumen transports a compressed gas and wherein the second lumen transports the liquid coolant.

2. The device of claim 1, wherein the liquid coolant is a perfluorocarbon.

3. The device of claim 2, further comprising:
   a plurality of mixing channels extending between said plurality of delivery ports and said first lumen; and
   a plurality of connecting tubes extending between said plurality of mixing channels and said second lumen, the first and second lumens arranged such that in use the perfluorocarbon and compressed gas are separately transported from the proximal end to the plurality of delivery ports on the outer wall the of the elongate tubular member.

4. The device of claim 2, wherein the perfluorocarbon is selected from the group consisting of perfluorohexane, perfluoropentane, and 2-methyl-perfluoropentane.

5. A medical device for cerebral cooling comprising:
   a first elongate tubular member adapted for insertion into a nasal cavity of a patient through a patient's first nostril, the first elongate tubular member comprising a proximal end, a distal end, a lumen extending therebetween, and a plurality of ports in fluid communication with the lumen;
   a second elongate tubular member adapted for insertion into a nasal cavity of a patient through the patient's second nostril, the second elongate tubular member comprising a proximal end, a distal end, a lumen extending therebetween, and a plurality of ports on the distal end of the second elongate tubular member in communication with the lumen;
   a manifold in fluid communication with the lumens of the first and second elongate tubular members, the manifold further communicating with a third and a fourth elongate tubular member; and
   a reservoir containing gas and a pressurized fluid, the pressurized fluid having a boiling point of less than 37° C. in communication with the third elongate tubular member and the gas in communication with the fourth elongate tubular member.

6. The device of claim 5, wherein the pressurized fluid is a perfluorocarbon.

7. The device of claim 6, wherein the perfluorocarbon is selected from the group consisting of perfluorohexane, perfluoropentane, and 2-methyl-perfluoropentane.

8. The device of claim 5, wherein the gas is air, oxygen, or a combination thereof.

* * * * *